US009360421B2

(12) United States Patent
Lanan et al.

(10) Patent No.: US 9,360,421 B2
(45) Date of Patent: Jun. 7, 2016

(54) USE OF NUCLEAR MAGNETIC RESONANCE AND NEAR INFRARED TO ANALYZE BIOLOGICAL SAMPLES

(75) Inventors: Maureen Lanan, Newton, MA (US); Amr Ali, Medford, MA (US)

(73) Assignee: Biogen MA Inc., Cambridge, MA (US)

( * ) Notice: Subject to any disclaimer, the term of this patent is extended or adjusted under 35 U.S.C. 154(b) by 0 days.

(21) Appl. No.: 14/241,647

(22) PCT Filed: Aug. 31, 2012

(86) PCT No.: PCT/US2012/053528
§ 371 (c)(1),
(2), (4) Date: Aug. 18, 2014

(87) PCT Pub. No.: WO2013/033638
PCT Pub. Date: Mar. 7, 2013

(65) Prior Publication Data
US 2014/0353503 A1 Dec. 4, 2014

Related U.S. Application Data

(60) Provisional application No. 61/581,778, filed on Dec. 30, 2011, provisional application No. 61/530,163, filed on Sep. 1, 2011.

(51) Int. Cl.
G01J 5/02 (2006.01)
G01N 21/359 (2014.01)
G01R 33/465 (2006.01)
G06F 19/00 (2011.01)
G01N 24/08 (2006.01)
G01N 33/50 (2006.01)
G01R 33/48 (2006.01)
G01R 33/46 (2006.01)

(52) U.S. Cl.
CPC ............ *G01N 21/359* (2013.01); *G01N 24/087* (2013.01); *G01N 33/50* (2013.01); *G01R 33/465* (2013.01); *G01R 33/4808* (2013.01); *G06F 19/703* (2013.01); *G01N 2201/12* (2013.01); *G01N 2201/13* (2013.01); *G01R 33/4625* (2013.01); *G06F 19/707* (2013.01)

(58) Field of Classification Search
USPC ........................................ 250/339.01–339.15
See application file for complete search history.

(56) References Cited

PUBLICATIONS

Rodrigues et al., "Calibration of near infrared spectroscopy for solid fat content of fat blends analysis using nuclear magnetic resonace data," 2005, analytica Chimica Acta vol. 544, pp. 213-218.*
L. Cecillon, "Fusion de donnees spectroscopiques appliquee aux sols," 2010, Journee HelioSpir.*
D. Ruthledge, "Outer Product Analysis (OPA) as a method to study the relations between sets of variables measured on the same individuals," 2008, Winter Symposium on Chemometrics, Cazan.*

(Continued)

Primary Examiner — Kiho Kim
(74) Attorney, Agent, or Firm — Wolf, Greenfield & Sacks, P.C.

(57) ABSTRACT

In one aspect, the disclosure provides methods for using NMR and NIR to evaluate biological samples. In some embodiments, the methods include a step of performing a Nuclear Magnetic Resonance (NMR) analysis on a sample to obtain an NMR spectrum, a step of performing a Near Infrared Spectroscopy (NIR) analysis on the sample to obtain an NIR spectrum, and/or a step of performing a data fusion analysis to evaluate the NIR spectrum.

18 Claims, 53 Drawing Sheets

(56) References Cited

PUBLICATIONS

International Search Report and Written Opinion for International Application No. PCT/US2012/053528 mailed Aug. 6, 2013.

International Preliminary Report on Patentability for International Application No. PCT/US2012/053528 mailed Mar. 13, 2014.

Andrade et al., Characterization of Encapsulated Flavor Systems by NIR and Low-field TD-NMR: A Chemometric Approach. Food Biophysics. 2008;3:33-47.

Barros et al., Principal component transform—Outer product analysis in the PCA context. Chemometrics and Intelligent Laboratory Systems. Aug. 15, 2008;93(1):43-8.

Chen et al., Correlation between near-infrared spectroscopy and magnetic resonance imaging of rat brain oxygenation modulation. Phys Med Biol. Feb. 21, 2003;48(4):417-27.

Cloarec et al., Statistical total correlation spectroscopy: an exploratory approach for latent biomarker identification from metabolic 1H NMR data sets. Anal Chem. Mar. 1, 2005;77(5):1282-9.

Crockford et al., Statistical heterospectroscopy, an approach to the integrated analysis of NMR and UPLC-MS data sets: application in metabonomic toxicology studies. Anal Chem. Jan. 15, 2005;78(2):363-71.

Duarte et al., High-resolution nuclear magnetic resonance spectroscopy and multivariate analysis for the characterization of beer. J Agric Food Chem. Apr. 24, 2002;50(9):2475-81.

Duarte et al., Multivariate analysis of NMR and FTIR data as a potential tool for the quality control of beer. J Agric Food Chem. Mar. 10, 2004;52(5):1031-8.

Giangiacomo et al., Characterization of Encapsulated Flavor Systems by NIR and Low-field TD-NMR: A Chemometric Approach. J Near Infrared Spectroscopy. 2009;17:329-35.

Gujral et al., On multivariate calibration with unlabeled data. J Chemometrics. 2011;25:456-65.

Jorgensen et al., On-line batch fermentation process monitoring (NIR)—introducing 'biological process time'. J Chemometrics. 2004;18:81-91.

Kemps et al., Albumen freshness assessment by combining visible near-infrared transmission and low-resolution proton nuclear magnetic resonance spectroscopy. Poult Sci. Apr. 2007;86(4):752-9.

Rutledge et al., Interpreting near infrared spectra of solutions by outer product analysis with time domain—NMR. In: Webb et al., Magnetic Resonance in Food Science: A View to the Future. The Royal Society of Chemistry. 2001;262:179-92.

Teofilo et al., Sorting variables by using informative vectors as a strategy for feature selection in multivariate regression. J Chemometrics. 2008;23:32-48.

Veselá et al., Infrared spectroscopy and outer product analysis for quantification of fat, nitrogen, and moisture of cocoa powder. Anal Chim Acta. Oct. 3, 2007;601(1):77-86. Epub Aug. 26, 2007.

Wiklund et al., Visualization of GC/TOF-MS-based metabolomics data for identification of biochemically interesting compounds using OPLS class models. Anal Chem. Jan. 1, 2008;80(1):115-22. Epub Nov. 21, 2007.

* cited by examiner

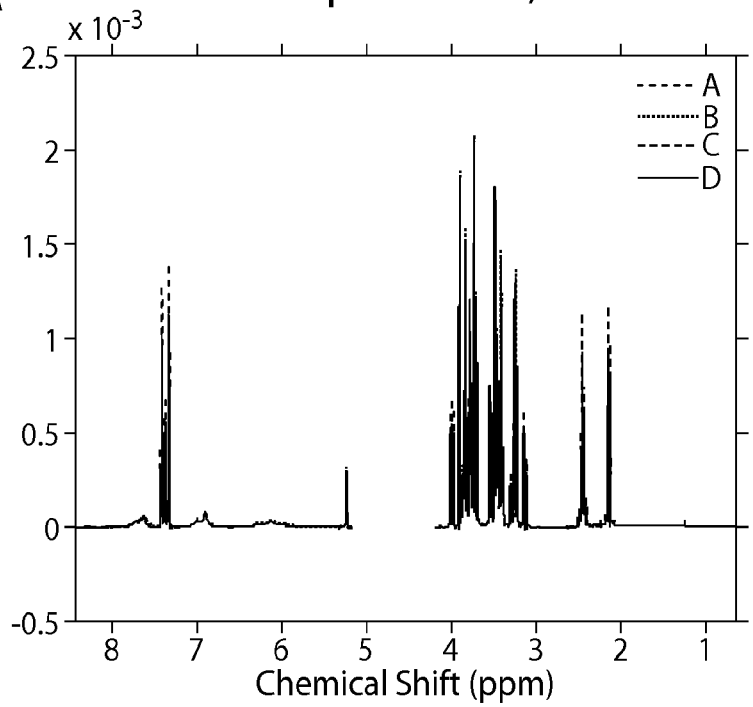
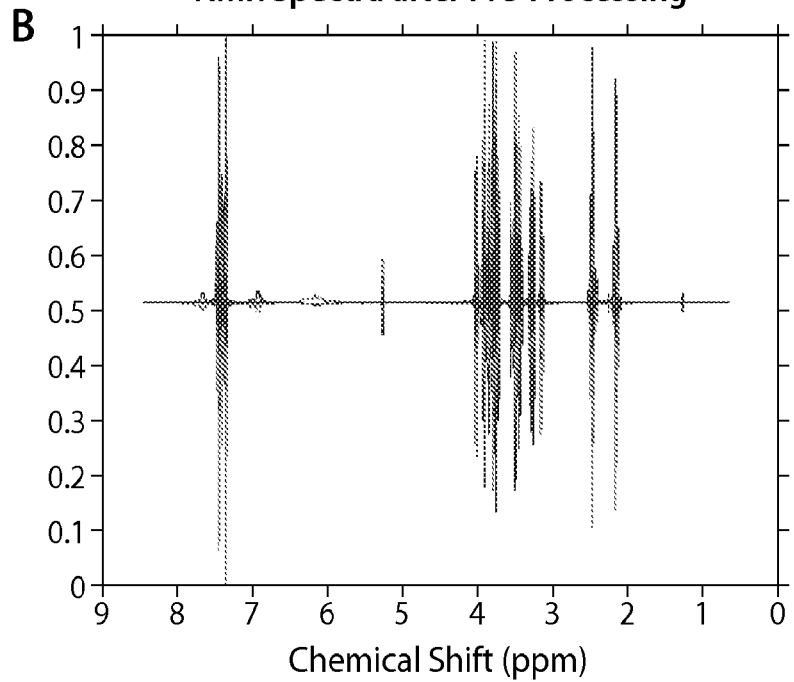
Fig. 1

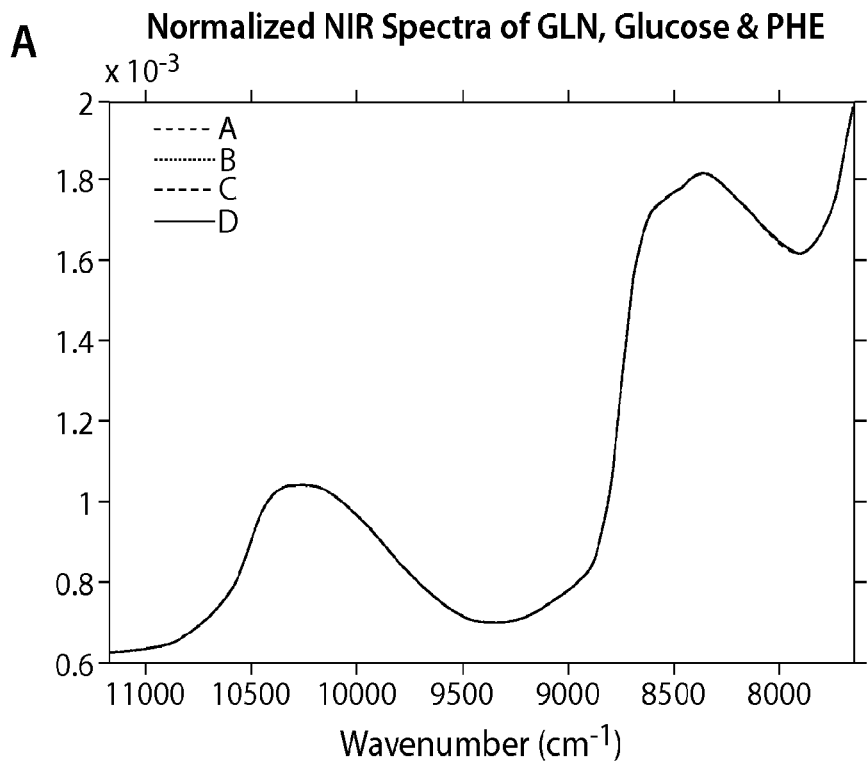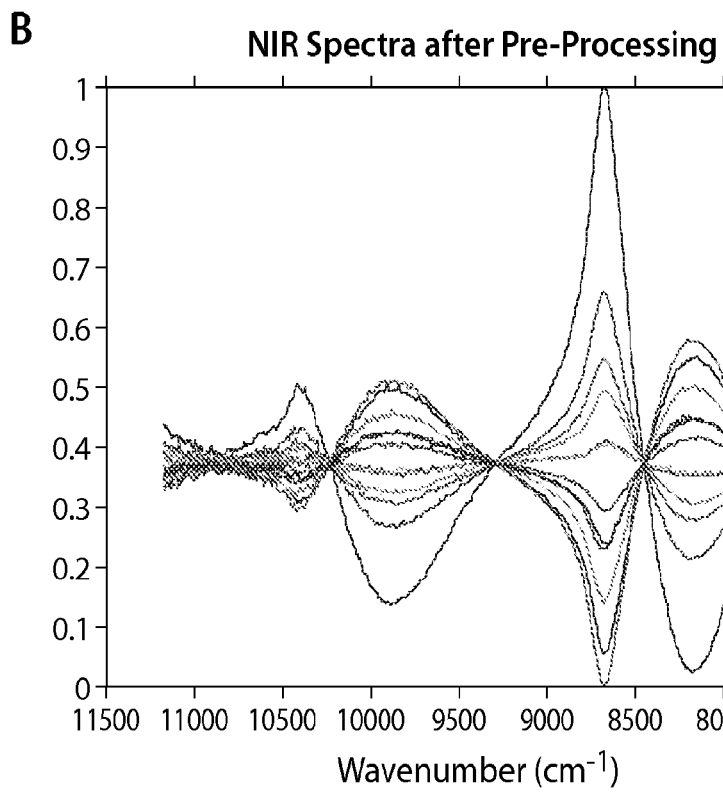
Fig. 2

*Outer Product pre-processing code*

```
[r c] = size(Data);

min1 = min((Data));

for i = 1:r
    for j = 1:c
        Data_adj(i,j) = Data(i,j) + abs(min1);
    end
end max1 = max(max(Data_adj));

for i = 1:r
    for j = 1:c
        Pre_Data(i,j) = Data_adj(i,j) / max1;
    end
end
```

Fig. 12

*Outer Product Analysis Calculation*

```
[n1 r] = size(NMR);
[n2 c] = size(NIR);

if( n1 ~= n2)
    fprintf('The number of samples in NMR and NIR is NOT the same')
    return
end Omatrix = zeros(n1, r, c);
unfolded = zeros(n1, r*c);

for i = 1:n1
    matrix_NMR = NMR(i,:);
    matrix_NIR = NIR(i,:);
    Omatrix(i,:,:) = matrix_NMR' * matrix_NIR;
    clear matrix_NMR matrix_NIR i
end for i = 1:n1
    unfolded(i,:) = reshape(squeeze(Omatrix(i,:,:)), 1, (r*c));
end unfolded_data = dataset(unfolded);

clear n1 n2 r c i unfolded
```

Fig. 13

*Regression Vector and VIP Combination*

```
VIP = vip(plsmodel)
Reg = plsmodel.reg;

for i = 1:length(VIP)
    Combine(i) = Reg(i) * VIP(i);
end

Combine_FOLDED = reshape(Combine, length(NMR), length(NIR));
```

Fig. 14

Sequential PLS Algorithm

```
function [ssq_1,regV,vip_scores,load_z,scores_z,predictions] =
seq_pls_ver1_Amr2( x,y,number_LV )
% This function calculates a series of one LV PLS models for two datasets:
%   x is NMR
%   y is NIR
%   number_LV is the number of latent variables to keep in each model_t.
%Changed by Amr
%Both datasets should already be pre-processed.
options=pls('options');
options.plots='none';
vip_scores=zeros(length(x),length(y));
regV = zeros(length(y),length(x));

for i=1:number_LV
    load_z{i}=zeros(length(y),length(x));
end predictions=zeros(length(y),size(y,1));

h = waitbar(0,'Please Wait');   %Initialize Progress Bar
for i=1:length(y)

model_t=pls(x,y(:,i),number_LV,options);
    for j=1:number_LV
        load_z{1,j}(i,:)=model_t.loads{2,1}(:,j);
        scores_z{1,j}(i,:) = model_t.loads{1,1}(:,j);
    end ssq_1(i,:,:) = model_t.detail.ssq;
    regV(i,:) = model_t.reg;
    predictions(i,:)=model_t.pred{1,2};
    vip_scores(:,i)=vip(model_t);

waitbar(i/(length(y)),h) %Place Progress
end vip_scores=vip_scores';

end
```

Fig. 15

| Name | H2O (%) | Glucose (%) |
|---|---|---|
| A1 | 5 | 0 |
| A2 | 10 | 0 |
| B1 | 5 | 5 |
| B2 | 10 | 5 |
| C1 | 5 | 10 |
| C2 | 10 | 10 |

- Vary Glucose and Water in $D_2O$
  - $D_2O$ shifts NIR absorbance
  - Use NMR tube as NIR cuvette
- NIR uses band-pass filter to allow only the combination band (4000-5000 $cm^{-1}$)
  - Better S/N but no overtones
- $^1$H-NMR
  - With no water suppression

Fig. 16

Sequential PLS: perform PLS repeatedly with intensities of each wavenumber as the Y-block

| GLN | Glucose | Pro |
|------|---------|------|
| High | Low | High |
| High | High | Low |
| Low | Low | Low |
| Low | High | High |

HEPES level the same in all

- NIR of Powder
  - Shake sample before each acquisition
  - Acquire 5 spectra
- NMR of Liquid
  - Dissolve in entire sample in water
  - Make 50% $D_2O$
  - Use water suppression on 500 MHz NMR

Fig. 22

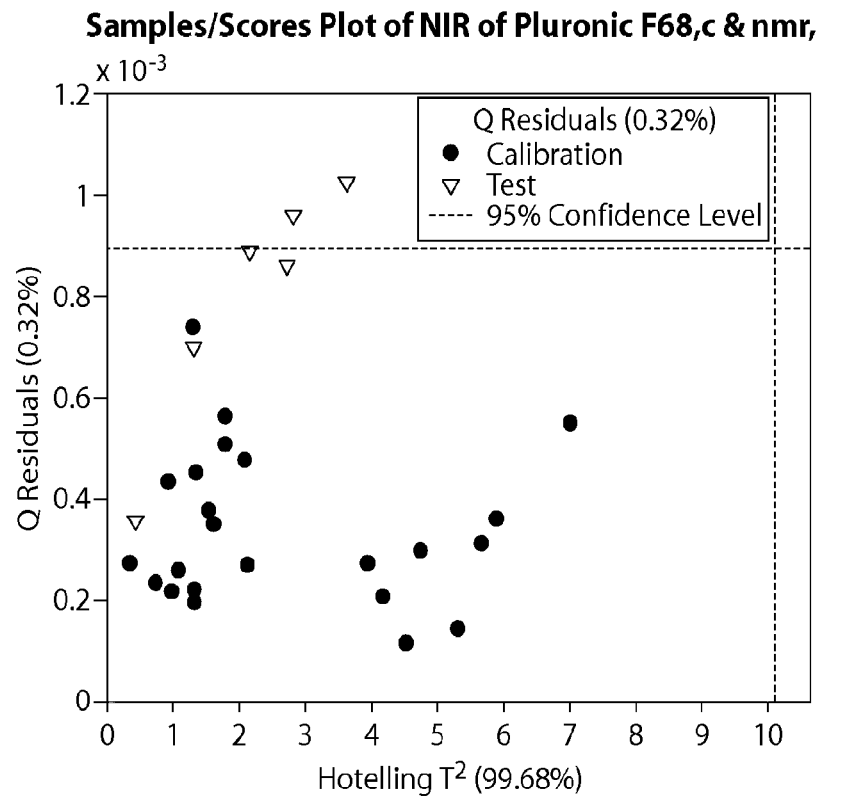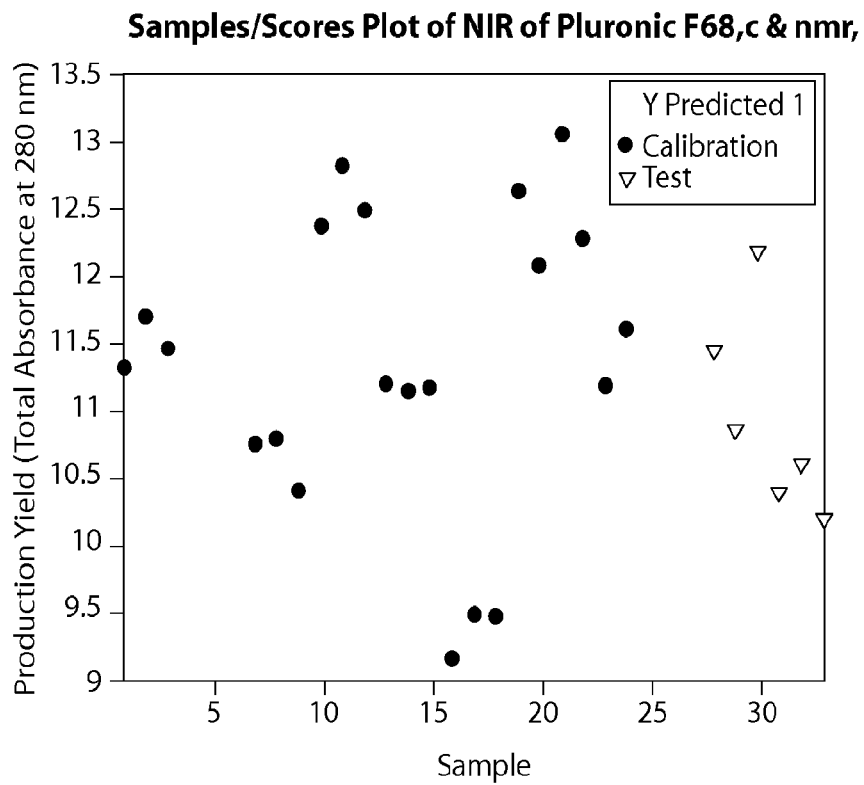
Fig. 43

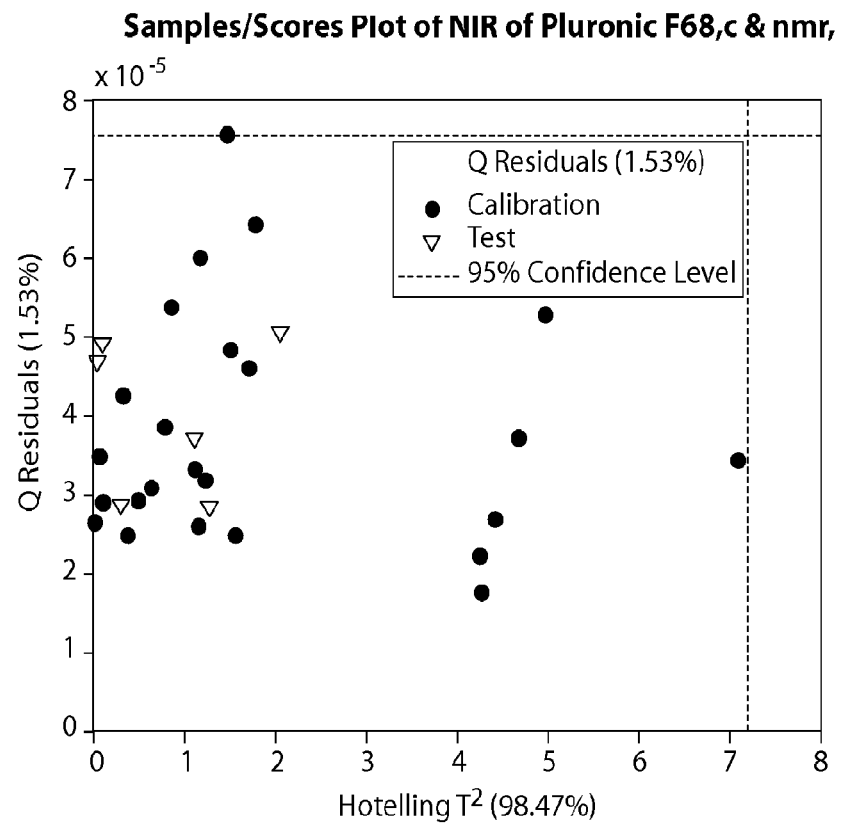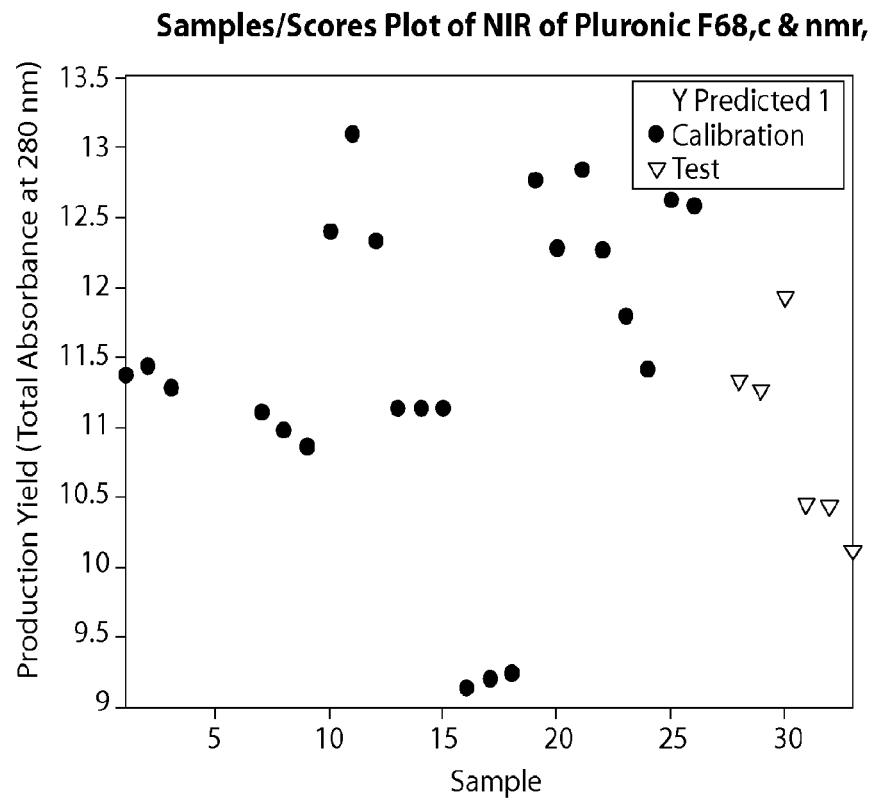
Fig. 44

US 9,360,421 B2

USE OF NUCLEAR MAGNETIC RESONANCE AND NEAR INFRARED TO ANALYZE BIOLOGICAL SAMPLES

RELATED APPLICATIONS

This application is a national stage filing under 35 U.S.C. §371 of International Application No. PCT/US2012/053528, filed Aug. 31, 2012, which claims the benefit under 35 U.S.C. §119(e) of U.S. provisional application No. 61/530,163, filed Sep. 1, 2011 and U.S. provisional application No. 61/581,778, filed Dec. 30, 2011, the content of which is hereby incorporated by reference in their entirety.

FIELD OF THE INVENTION

The invention is in the field of spectroscopic analysis of biological samples.

BACKGROUND

The production of biological materials in biological productions processes often involves expensive starting material and complex time-consuming synthesis and purification steps. The production process can fail at any stage due to low quality material and/or poor yields in one or more steps. However, failure often is not detected until late in the production process when final yields are evaluated. This can result in an expensive waste of time and material.

SUMMARY OF THE INVENTION

In one aspect, the disclosure relates to the use of Near Infra-Red (NIR) and $^1$H-Nuclear Magnetic Resonance (NMR) to improve the analysis of starting materials and/or intermediate synthesis/growth and purification steps in order to evaluate the production process of a biological molecule.

In some embodiments, the disclosure provides methods of evaluating a biological sample that include a data fusion analysis. In some embodiments, the data fusion analysis uses data obtained in an NMR spectrum to analyze an NIR spectrum of the same sample.

In one aspect, the disclosure provides a method of evaluating a biological sample, the method comprising performing a Nuclear Magnetic Resonance (NMR) analysis on a sample to obtain an NMR spectrum, performing a Near Infrared Spectroscopy (NIR) analysis on the sample to obtain an NIR spectrum, and performing a data fusion analysis to evaluate the NIR spectrum.

In one aspect, the disclosure provides a method of evaluating a biological sample, the method comprising performing a Near Infrared Spectroscopy (NIR) analysis on a sample to obtain an NIR spectrum, and performing a data fusion analysis of the NIR spectrum with a reference NMR spectrum.

In one aspect, the disclosure provides a method of evaluating a biological sample, the method comprising performing a Near Infrared Spectroscopy (NIR) analysis on a sample to obtain an NIR spectrum, and analyzing a portion of the NIR spectrum that was identified in a data fusion analysis with an NMR spectrum.

In one aspect, the disclosure provides a method of evaluating a biological sample, the method comprising performing a Near Infrared Spectroscopy (NIR) analysis on a sample to obtain an NIR spectrum for a subset of NIR wavelengths, wherein the subset was identified in a data fusion analysis with an NMR spectrum.

In some embodiments of methods provided herein, the data fusion analysis comprises an Outer Product Analysis (OPA). In some embodiments, the OPA comprises multiplying the NMR spectrum with the NIR spectrum. In some embodiments, the OPA comprises multiplying Regression vectors and Variable Importance in Projection (VIP) vectors.

In some embodiments of methods provided herein, the data fusion analysis comprises a partial least square (PLS) analysis. In some embodiments, the PLS analysis comprises an x-block of NIR and NMR data and a y-block of one or more components of the biological sample. In some embodiments, the results are displayed using a combination vector. In some embodiments of methods provided herein, the data fusion analysis is a computer-implemented step.

In some embodiments, one or more spectra (e.g., NIR and/or NMR spectra) are pre-processed (e.g., for data fusion analysis). In some embodiments, the data are normalized (e.g., normalized to 1). In some embodiments, the data are scaled (e.g., scaled such that the intensity ranges from 0-1).

In one aspect, the disclosure provides a method of evaluating a biological sample, the method comprising performing an NMR experiment on a component of the biological sample to obtain an NMR spectrum, performing an NIR experiment on the component of the biological sample to obtain an NIR spectrum, performing a data fusion analysis of the NIR spectrum with the NMR spectrum to generate an assigned NIR spectrum, performing an NIR experiment on the biological sample to obtain an NIR spectrum, and determining the presence in the biological sample of the component of the biological sample by comparing the NIR spectrum of the biological sample to the assigned NIR spectrum. In some embodiments, the data fusion analysis is a computer-implemented step. In some embodiments, the determining step is a computer-implemented step.

In one aspect, the disclosure provides a method for evaluating a biological sample, the method comprising performing a first NIR experiment on a desired sample to obtain an NIR spectrum that correlates with a desired sample, performing a second NIR experiment on a non-desired sample to obtain an NIR spectrum that correlates with a non-desired sample, performing an NIR experiment on a biological sample to obtain an NIR spectrum, and determining if the NIR spectrum of the biological sample correlates with the NIR spectrum of the desired sample or the NIR spectrum of the non-desired sample. In some embodiments, the determining step is a computer-implemented step. In some embodiments, the method further comprises performing a data fusion analysis of one or more of the NIR spectra with an NMR spectrum of the same sample. In some embodiments, the data fusion analysis is a computer-implemented step.

In one aspect, the disclosure provides a method for evaluating a biological sample, the method comprising performing an NIR experiment on a biological sample to obtain an NIR spectrum, and comparing the NIR spectrum to a reference NIR spectrum that has undergone data fusion analysis with an NMR spectrum. In some embodiments, the comparing step is a computer-implemented step.

In one aspect, the disclosure provides a method for evaluating a biological sample, the method comprising performing an NIR experiment on one or more components in a biological sample to obtain an NIR spectrum of the one or more components of the biological sample, performing a data fusion analysis to generate a predicted NIR spectrum, performing an NIR experiment on a biological sample to obtain an NIR spectrum, and analyzing the NIR spectrum of the biological sample based on the predicted NIR spectrum.

BRIEF DESCRIPTION OF THE DRAWINGS

The figures are illustrative only and are not required for enablement of the invention disclosed herein.

FIG. 1 shows the NMR spectra of GLN, Glucose and PHE after normalization to the total area (A) and after preprocessing (B).

FIG. 2 shows the NIR spectra of GLN, glucose and PHE solutions after normalization to the total area (A) and after preprocessing (B).

FIG. 12 shows outer product pre-processing code.

FIG. 13 shows outer product analysis calculation.

FIG. 14 shows regression vector and VIP combination

FIG. 15 shows sequential PLS algorithm.

FIG. 16 provides an overview of a proof of concept experiment with water and glucose.

FIG. 22 provides an overview of a proof of concept experiment with a factorial mix of DMEM components.

FIG. 33 shows the NMR spectra of gln, glucose and phe after normalization to the total area (FIG. 33A) while

FIG. 34 shows the combination band NIR spectra of gln, glucose and phe solutions after normalization to the total area (FIG. 34A) while

FIG. 43 shows the validation of the NIR only model with new pluronic F68 lot performance prediction using the NIR without wavelength selection.

FIG. 44 shows the validation of the NIR only model using new pluronic F68 performance prediction using the NIR only model with wavelength selection.

DETAILED DESCRIPTION OF THE INVENTION

Figure 3:
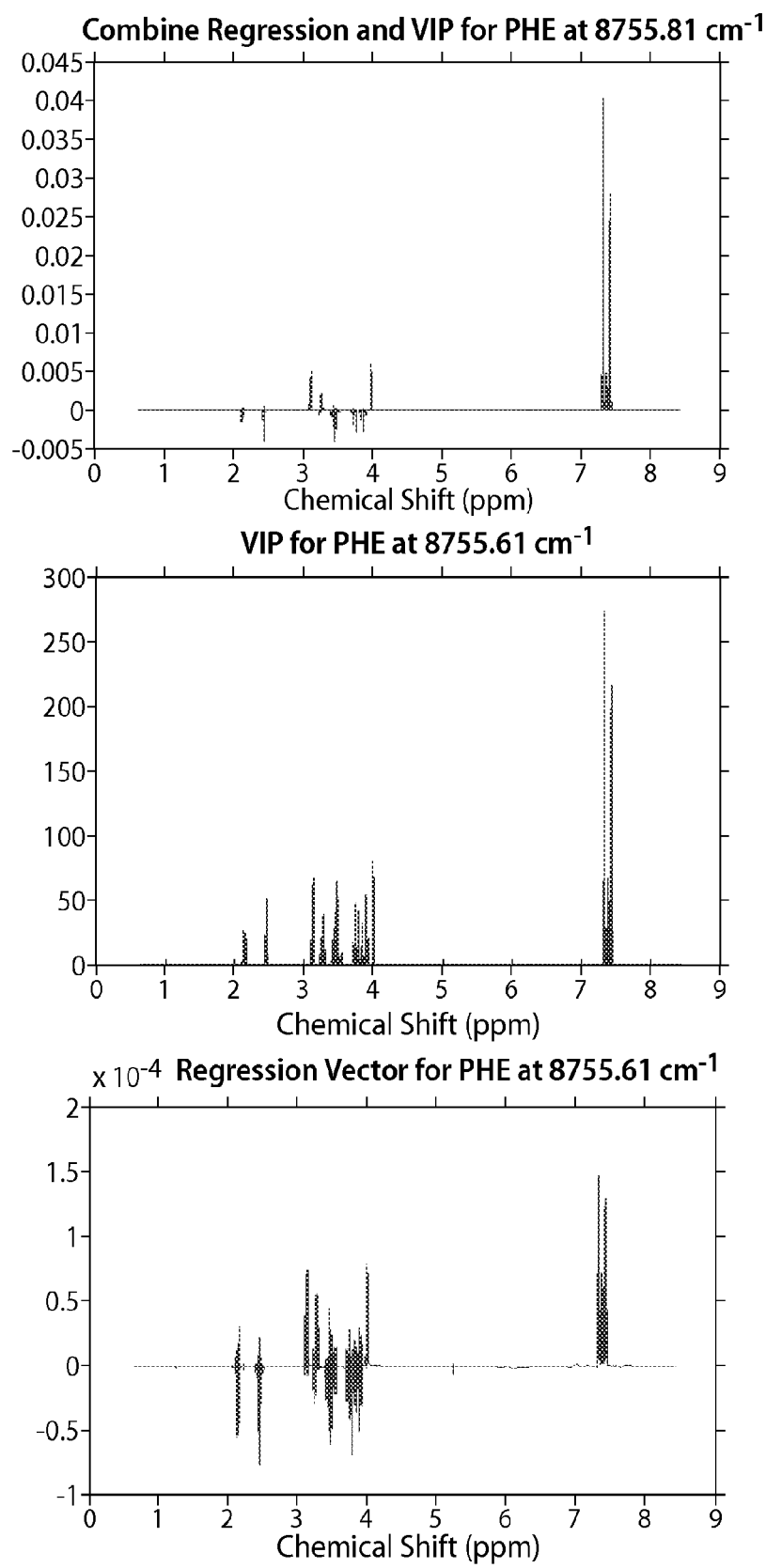
FIG. 3 shows a comparison of (A) combined, (B) regression, and (C) VIP vectors for qualitative interpretation of NIR and NMR spectra.

In one aspect, the disclosure relates to analytical techniques for evaluating material at one or more steps during a biological production process.

Near infra-red (NIR) spectroscopy is widely used in the pharmaceutical industry to identify raw materials[11, 12] and to monitor upstream steps for biopharmaceutical[13-21] manufacturing. There are also numerous process control applications of NIR in the chemistry and pharmaceutical industries[20, 22, 23]. Despite the acceptance of NIR as a specific, rugged spectroscopic technique, there remain hurdles to more widespread adoption in biologics manufacturing and research. The primary limitation from the point of view of a chemist or chemical engineer is the challenge to interpret a spectrum using chemical intuition. It is often not enough to know that a process is not performing as desired; the reason needs to be identified.

In one aspect, the disclosure provides techniques for using proton NMR to interpret NIR spectra in a way to address the intuitive failing of NIR. In some embodiments, factor analysis is followed with a technique for combining NIR and NMR using external variables or against each other in order to select NIR wavelengths to include in NIR-only model raw material models.

Cell-culture based production can be sensitive to the level and quality of key nutrients in media and feed stocks. Recent publications describe the use of high resolution NMR and LC-MS to pinpoint key components in complex nutrient mixtures that account for significant product variation for biopharmaceuticals[24, 25]. Similar techniques have been reported for analysis of the quality of beer[26, 27]. Despite having detailed information about which compounds in a mixture are primarily impacting production, there is still challenge converting this knowledge into a rugged analytical test method that can be used on a routine basis. In particular, to meet an interpretation of current regulatory guidance documents each shipment of raw material must be identified before it can be used. For a cell-culture process, there can be hundreds of different chemicals, chromatography resins, and product contact items for each manufacturing run each requiring testing. To manage the volume of testing, simple instrument operation and minimal sample handling are needed. The analytical method should also be robust to match the demanding timelines in a production environment. Techniques such as high-resolution NMR are too delicate to support routine operations since they require periodic maintenance.

In one aspect, the disclosure provides methods for translating process knowledge about raw materials into an effective operational approach. In some embodiments, the similar information content in NMR and NIR spectra of powder raw materials and solutions are used to predict the wavelengths needed to have a robust, meaningful NIR-only test method. The need to reduce false negative rates and at the same time to improve vigilance on raw material quality demand newer strategies to support a NIR-only raw material screening approach for raw materials.

Chemically defined biopharmaceutical cell-culture nutrient powders typically consist of 10 to 40 materials. Catching faulty raw material batches that could impact manufacturing provides information early enough in the production chain that adjustments may be possible. First, it may be possible to work with the supplier to reduce the incidence of known issues. Second, design space adjustments may be possible which will compensate for the known raw material issue. Lastly, a particular lot of raw material may be avoided. Each of these actions adds value since the end result will be better product quality and control. In addition, the technology provides a key link to creating a more flexible manufacturing process, better suited to adjust to supply-chain disruptions arising from climate change.

Although the problem of raw material control becomes easier with chemically defined raw materials, there is still often a need to perform ID testing on each new raw material lot received based on current GMP CFR requirements. However, in addition to a narrow identity test criteria proscribed by law, there is also a desire to have test methods that are capable of anticipating the impact of raw material variation on product quality and process consistency. By developing test methods that can meet the demands of an identity test and that directly or indirectly measure differences in otherwise conforming incoming raw material lots, the likelihood of detecting non-conforming raw materials improves as does the ability to ensure product quality.

In some embodiments, an ID test refers to a GO/NO GO test. In order to expand an ID test into something more informative, a challenge is to find out the critical attribute(s) to which the material should be deeded good or bad. In order to find such criteria and/or which part of a spectrum reflects the important aspect of the material, correlation methods can be performed to identify the important aspects/compounds of the raw material and which parts of the spectra show a signature that reflects the trend. In the case of outer product analysis or sequential PLS, they are both used to identify the important sections of the spectra (wavelength selection). With this knowledge, an analytical method can be implemented to help provide a GO/NO GO determination based on the predicted performance. In some embodiments, this information can also support the ID test criteria required to conform with best practices.

Near Infra-Red Analysis

NIR (Near-Infra Red) can be an attractive ID test for manufacturing processes since it is selective and requires no sample preparation. Once a regression model is developed that relates multiple wavelengths to the property of interest—either qualitative or quantitative—an operator can acquire new spectra without a high degree of training. Models are often developed using partial least squares (PLS) against some variable of interest and predict an ID or calculate a value.

NIR absorbance spectra typically contain signals from multiple sample components at each wavelength. Signals arise from organic compounds, factors affecting hydrogen bonding such as temperature or ionic strength, and light scattering if powder samples are measured. In addition to dramatic differences in molar absorptivity between the combination bands and overtones, NIR spectrometers have limited and varying source intensity across the spectral range of interest. Accordingly, the signal to noise ratio can vary significantly across the spectrum. It is widely reported that more robust NIR models result when wavelengths dominated by noise are omitted. A variety of strategies to select wavelengths have been described including manual, knowledge-based approaches, regression techniques, automated wavelength region selectors such as genetic algorithms and interval selection methods[28]. Of these, genetic algorithms perform best, but do not lend themselves to ready interpretation based on chemical knowledge. Of even more concern for a raw material application is the balance between a need for a robust quantitation and low false negative rates. Standard techniques remain constrained by the inherent lack of samples for raw material applications. It can take years to accumulate enough experience with raw material vendor lots to establish strong process understanding. It is not possible to anticipate all the types of raw material changes that may occur over such long time spans.

There remain significant risks for errors where a sample is different from any seen previously, yet still be acceptable because the levels of individual components are acceptable. In either case, operational concerns are clearly connected to the enhanced vigilance from use of a spectroscopic technique like NIR for raw material ID and characterization.

Despite availability of tools and chemical intuition relating NIR and NMR (Nuclear Magnetic Resonance) information content, data fusion has not been reported for high resolution NMR and NIR. This disclosure provides unique data processing strategies needed and benefits derived from the combination of NIR and NMR using designed experimental mixtures and spectra of a real complex nutrient used as a raw material in biopharmaceutical manufacturing. In some embodiments, by combining information in the VIP plot (Variable Importance in Projection) and regression vector obtained from an OPA (Outer Product Analysis) or sequential PLS (Partial Least Squares) model, NIR wavelengths are clearly related to positive or negative correlation to product yield and linked to particular components in the mixture using NMR. This disclosure also provides enhanced NIR-only wavelength selection based on the combined NIR and NMR spectra.

In one aspect, the disclosure provides methods of combining NIR and NMR spectroscopy techniques to analyze (biological) samples. NMR is a powerful technology that can help determine the qualitative and quantitative composition of a sample (e.g., a biological sample or a product synthesis sample). However, because of the sophisticated equipment needed and the extensive training of the operators, NMR is an expensive technology that cannot readily be implemented in routine analysis of materials prior to, or during, a biological production process. In contrast to NMR, NIR is an inexpensive technique that allows for the rapid analysis of the presence of one or more components in a sample and thus the evaluation of the sample. For example, NIR spectra can be obtained almost continuously by adding an optical fiber to a sample. However, the ability to analyze complex samples (e.g., with more than two or three components) with NIR alone was limited prior to the present disclosure.

NMR and NIR Data Fusion Analysis

In one aspect, the disclosure provides methods for data fusion analysis. In some embodiments, the disclosure provides methods for fusing data obtained in an NMR experiment with data obtained in an NIR experiment. In some embodiments, methods allow for improvement of the resolution of the data obtained in an NMR experiment. In some embodiments, methods allow for improvement of the resolution of the data obtained in an NIR experiment. In some embodiments, methods allow for improvement of the resolution of the data obtained in both an NMR and an NIR experiment.

NIR and NMR share spectroscopic characteristics that make them well suited for data fusion. Both techniques probe the physical and chemical environment of protons with similar analytical sensitivity. Even though the time-scale for vibrations in NIR is significantly faster than the magnetic interactions induced during NMR, the common physical basis of the two techniques (the relative location of atoms in a molecule) allows for the combination of the two techniques. In some embodiments, the disclosure provides methods that employ the relationship between proton NMR nuclear spin transitions and the electro-magnetic-spectrum-dependent vibrational motions of a molecule. When a molecule is illuminated with a specific vibrational frequency during the simultaneous acquisition of NMR spectra a change in either chemical shift and/or line broadening of those specific bonds associates with that vibrational frequency can be observed in the proton NMR signal. By stimulating these molecule-specific vibrational modes while acquiring NMR spectra a method of providing additional molecular specificity in the NMR is obtained.

In some embodiments, the disclosure provides a method of analysis where proton NMR is used to interpret NIR. The analysis is based on a multi-faceted analogy between the strengths, limitations, sensitivity, and selectivity of the two types of spectroscopy. In some embodiments, the disclosure provides methods wherein NIR is used to improve NMR spectra and vice-versa. In some embodiments, the improvements afforded by methods provided herein include improved signal-to-noise, enhanced selective quantitative NIR models, and/or intuitive NIR spectral interpretation. In one aspect, the disclosure provides methods for using the relationship between NIR and NMR to remove instrument noise variation from NMR spectra.

In one aspect, the disclosure provides a method of evaluating a biological sample, the method comprising performing a Nuclear Magnetic Resonance (NMR) analysis on a sample to obtain an NMR spectrum, performing a Near Infrared Spectroscopy (NIR) analysis on the sample to obtain an NIR spectrum, and performing a data fusion analysis to evaluate the NIR spectrum.

In one aspect, the disclosure provides a method of evaluating a biological sample, the method comprising performing a Near Infrared Spectroscopy (NIR) analysis on a sample to obtain an NIR spectrum, and performing a data fusion analysis of the NIR spectrum with a reference NMR spectrum.

In one aspect, the disclosure provides a method of evaluating a biological sample, the method comprising performing a Near Infrared Spectroscopy (NIR) analysis on a sample to obtain an NIR spectrum, and analyzing a portion of the NIR spectrum that was identified in a data fusion analysis with an NMR spectrum.

In one aspect, the disclosure provides a method of evaluating a biological sample, the method comprising performing a Near Infrared Spectroscopy (NIR) analysis on a sample to obtain an NIR spectrum for a subset of NIR wavelengths, wherein the subset was identified in a data fusion analysis with an NMR spectrum.

In some embodiments of the methods provided herein, data fusion analysis comprises an Outer Product Analysis (OPA). In some embodiments, OPA comprises multiplying the NMR spectrum with the NIR spectrum.

In one aspect, OPA is used by analyzing the results as the product of Variable Importance in Projection (VIP) and regression vectors. By multiplying the regression and VIP vectors together, a more easily understood spectral assessment is provided. In some embodiments a combination vector is used. It should be appreciated that the product of Variable Importance in Projection (VIP) and regression vectors may be analyzed by displaying the product data and/or results, comparing the product data and/or results including the use of algorithms. However, other analysis techniques may be used.

In one aspect, OPA, as used herein, allows for the comparison of metabolites that are critical to cell growth, product yield, or product quality. For example, outer-product analysis between NMR spectra and/or NIR spectra acquired from media samples from different bioreactor expansion stages along a manufacturing train allow for the identification (e.g., by visualization) of key biochemical processes that may correlate to determine final yield during a particular step of the process.

In some embodiments, data fusion analysis comprises a partial least square (PLS). In some embodiments, the PLS analysis comprises an x-block of NIR and NMR data and a y-block of one or more components of the biological sample.

In any of the methods disclosed herein, the data fusion analysis, or a component thereof (e.g., OPA or PLS), or a pre-processing step, can be a computer-implemented step.

In one aspect, the disclosure provides methods for assigning peaks in an NIR spectrum. In some embodiments, the peaks in the NIR spectrum are assigned by correlating the peaks in an NIR spectrum with peaks in an NMR spectrum.

In one aspect, the disclosure provides methods for identifying regions of interest in an NIR spectrum. In some embodiments, the regions of interest in the NIR spectrum are assigned by correlating the peaks in an NIR spectrum with peaks in an NMR spectrum. In some embodiments, the region of interest in the NIR spectrum allows for the identification of biologically relevant molecule.

In one aspect, the disclosure provides methods for improving the data obtained by NIR spectra by performing a data fusion analysis with data obtained in an NMR spectrum. In some embodiments, methods include an outer product analysis (OPA) of the NMR and NIR spectra of a sample. In some embodiments, methods disclosed herein allow for the assignment of a specific vibrational signal in NIR by correlating the signal with a chemical shift in an NMR spectrum.

In one aspect, PLS is used sequentially to a set of NIR and NMR spectra. The predicted result—either NIR or NMR spectra—provides better correlation to the 'labeled' result such as process yield than either original spectrum. While not being limited to a specific mechanism, the improvement is likely due to the relative suppression of instrument or chemical noise present in NMR and NIR, respectively.

In one aspect, methods presented herein allow for the use of combined VIP and regression vectors as a strategy to perform NIR wavelength assignment and selection.

In some embodiments, methods include a step of obtaining an NMR spectrum of a sample, obtaining an NIR spectrum of the same sample and multiplying each NMR and NIR spectral point to obtain an outer product dataset. In some embodiments, the data set is used as an X block input for Partial Least Square (PLS) Analysis and PLS is performed using one of the known components of the sample as the Y block (in the PLS analysis) resulting in a regression vector and a variable importance in projection (VIP). In some embodiments, the PLS is performed using venetian blind cross-validation. In some embodiments, the regression vector and the VIP are multiplied to obtain a combined array. In some embodiments, the combined arrays allows for the parsing of a specific vibrational signal in NIR with a chemical shift in an NMR spectrum.

In one aspect, the disclosure provides a method including one or more of the steps of obtaining NIR and NMR spectra of sample, pre-processing the NIR and/or NMR spectra wherein the whole spectra or certain regions of the spectra are pre-processed (e.g., are normalized and/or scaled), multiplying the pre-processed NMR and NIR spectra, using PLS or OPA to obtain a regression vector and VIP, multiplying the regression vector and VIP to obtain correlation between NIR and NMR spectra, identifying regions of interest in NIR spectra based on the correlation, and optionally, using the regions of interest as a reference to assess new samples.

In one aspect, the disclosure provides a method including the steps of obtaining NIR and NMR spectra of sample, pre-processing the NIR and/or NMR spectra wherein the whole spectra or certain regions of the spectra are pre-processed, multiplying the pre-processed NMR and NIR spectra, using PLS to obtain regression and VIP vectors, multiplying the regression and VIP vectors to combine the information, identifying regions of interest in the NIR spectra based on the combined vector, and optionally, creating new NIR method based on the selected wavelength region In one aspect, the disclosure provides a method including the steps of obtaining NIR and NMR spectra of sample, pre-processing the NIR and/or NMR spectra wherein the whole spectra or certain regions of the spectra are pre-processed, performing PLS with NMR points as y block and NIR spectra as x block or vice versa, analyzing a map of regression vector multiplied by the VIP to highlight correlations between NIR and NMR, identifying regions of interest in the NIR spectra based on the combined vector, and optionally, creating new NIR method based on the selected wavelength region.

In some embodiments, the data for one or more spectra being analyzed are pre-processed (e.g., prior to or as part of a data fusion analysis). In some embodiments, the data are normalized (e.g., normalized to 1) and/or are scaled (e.g., scaled such that the intensity ranges from 0-1). In some embodiments, spectra (e.g., NMR spectra) can be normalized (e.g., normalized to the total area), and/or baseline corrected (e.g., using Weighted Least Squares (WLS)), and/or, mean-centered. In some embodiments, spectra (e.g., NIR spectra) are corrected (e.g., using Extended Multiplicative Scatter Correction (EMSC)), and/or normalized (e.g., normalized to total area) and/or mean centered. In some embodiments, data is prepared for Outer Product Analysis (OPA) by shifting and normalizing the spectra so that the minimum is 0 and the maximum is 1. However, it should be appreciated that other pre-processing steps (e.g., other correction, normalization, scaling, and/or centering) techniques may be used in some embodiments. In some embodiments, processing the data prior to the multiplication of the dimensions is useful as described herein.

NMR results have been used to quantitate a component and that result has been used as the reference data for an NIR model (L. Andreade, I. A. Farhat, K. Aeberhardt, S. B. Engelsen, Food Biophysics 3, 33, 2008). Magnetic resonance imaging is related to imaging by NIR and it has been shown that both methods provide similar results for blood oxygen distribution in biological samples (Y. Chen, D. R. Tailor, X. Intes, B. Chance, Physics in Medicine & Biology 48, 2003, 417). Time-domain NMR (TDN) has been compared to NIR and the outer-product between the two techniques was shown to correlate (D. N. Rutledge, A. S. Barros, R. Giangiacomo, Spec. Publ.—R. Soc. Chem. Special Publication—Royal Society of Chemistry 262, 179, 2001).

Ab-initio calculations have shown that vibrational and NMR results can be combined to improve NMR spectra prediction calculations (K. Ruud, P.-O. Astrand, P. R. Taylor, Journal of the American Chemical Society 123, 4826, 2001). Solid-state mid-IR and solid-state NMR have been used to correlate the vibrational frequency and NMR chemical shift for different compounds with surface hydroxyl bonds (E. Brunner, H. G. Karge, H. Pfeifer, Z. Phys. Chem. (Munich): Zeitschrift fuer Physikalische Chemie (Muenchen, Germany) 176, 173, 1992).

However, data fusion techniques have not been used to process NIR or NMR spectra in order to analyze and evaluate more complex biological samples such as starting materials for biological growth and expression systems, or samples of the growth and expression systems themselves.

Predicting NIR Spectra

In one aspect, the disclosure provides methods for predicting NIR spectra. In some embodiments, methods for predicting an NIR spectrum comprise obtaining an NMR spectrum of a sample, obtaining an NIR spectrum of the same sample, and pre-processing the spectra according to methods provided herein. In some embodiments, the pre-processed NMR spectrum is used as an x-block in sequential PLS while the pre-processed NIR spectrum is used as the y-block in PLS. In some embodiments, in a next step a latent variable PLS model is calculated for each NIR wavelength to obtain a set of predicted NIR spectra. In some embodiments, the predicted NIR spectra are used as the x-block in a sequential PLS, using concentrations of known components in the sample as y-blocks in the sequential PLS. In some embodiments, the Predicted NIR spectra obtained by PLS allow for better interpretation of biological samples.

Analyzing Biological Samples

In one aspect, the disclosure provides methods for the analysis of biological samples. In some embodiments, the disclosure provides methods for evaluating a biological production process. In some embodiments, the analysis of a biological sample or a biological production process comprises determining the presence of one or more components in a biological sample. In some embodiments, the analysis of a biological sample comprises determining the quantity of one or more components in the biological sample. It should be appreciated that certain methods provided herein allow for the analysis of a wide variety of biological samples. Biological samples, as used herein, refer to samples that include one or more components of a biological production process. For example, a biological process may be the production of one or more biological molecules in a cell production system (e.g., using any suitable bacterial, yeast, mammalian, insect, or other cell line). Biological molecules may be antibodies or other molecules (e.g., recombinant polypeptides). Components of a biological production process include sugars, amino acids, peptides, proteins, nucleic acids, etc. In some embodiments, the biological sample includes a surfactant. In some embodiments, the surfactant is Pluronic F68.

In some embodiments, a sample being analyzed includes or consists of (e.g., consists essentially of) one or more components used in a biological synthesis. Components can be raw materials useful for cell growth, e.g., amino acids, peptides, sugars, carbohydrates, vitamins, growth factors, salts, synthetic material, antibiotics, surfactants, buffers, or other material or any combination thereof. In some embodiments a sample can be in dry form. In some embodiments, a sample can be in liquid form (e.g., an aqueous solution or suspension). In some embodiments, a sample can be processed (e.g., with the addition of additional components or by concentration or by dilution, by the addition of an appropriate buffer or liquid phase, etc.) prior to NMR and/or NIR analysis.

Lot-to-lot variation in raw material lots used in biological manufacturing processes presents an ongoing manufacturing risk in biotechnology and related industries. Several analytical methods have been used to acquire information about the materials—almost entirely aqueous solutions—but most of these methods are not robust enough to provide a practical, routine test to help understand and control these variations.

NIR is well known and widely used to identify dry powder materials and concentrated organic raw materials. NIR spectrometers are rugged, simple to operate and easy to maintain. However, NIR is not typically applied to aqueous solutions because in NIR analysis water interacts with the compounds and components to be analyzed, and strongly reduces the sensitivity of the NIR.

In contrast to NIR, NMR involves much more delicate analytical instrumentation and NMR has generally not been used for routine raw material analysis (in biological productions processes).

In some embodiments, methods provided herein include a step of acquiring both NMR and NIR spectra on the same liquid preparation of a raw material over a period of time, thereby projecting the NMR loadings plot based on the score obtained from NIR spectra. Thus, the increased level of a particular component in an unknown lot of raw material can be identified based on the NMR results, saving time on any additional follow-up analytical testing needed to verify whether the new lot of raw material could be used in a manufacturing plant.

The primary limitation for using NIR as a quality control and process monitoring tool is that the spectra from different components of a mixture are overlapping so that effectively no information about chemical composition differences between samples can be deduced by inspecting NIR spectra. NIR spectra show that something is different—but they cannot indicate what causes the difference without prior knowledge. By relating the NIR spectra differences to NMR spectra, according to methods provided herein, the underlying chemical change that accounts for the NIR difference was determined without additional analysis.

In some embodiments, evaluating a biological sample includes determining the presence of one or more components in a biological sample. In some embodiments, the presence of one or more components can be correlated to the quality of the sample and/or the progress of a particular biological manufacturing process. Components that can be analyzed according to the methods provides herein include, sugars, amino acids, nucleic acid, etc. For instance, for an optimal biological production process it may be desired to have a specific amount of glucose present at the beginning of the biological production process. Determining the presence and/or the amount of glucose than allows for evaluating a biological sample. For instance, if less than the desired amount of glucose is present the batch of starting material may be rejected before the biological manufacturing takes place.

In some embodiments, the quantity of a component during the biological production process can be used to monitor the progress of the biological production process. Thus, for instance, if glucose is consumed during a biological production process, the presence of the same amount of glucose during the progression of the biological production process as at the beginning of the biological production process is a sign that the bioprocess is not proceeding as desired. In addition, the presence of a new component can be a sign that the biological production process is proceeding or not proceeding as planned. Thus, a biological production process may be monitored for the occurrence of desired product or indicator that biological production process is progressing as desired. On the other hand, the presence of a particular metabolite may be a sign that cells in the biological production process are not generating the desired product but, for instance, are merely proliferating. Thus, determining the presence of one or more components in a biological sample is a way of evaluating the sample and predicting the successfulness (e.g., yield) of a biological production process.

It should be appreciated that the component analysis can also be expanded to multiple components. Thus, for instance, a biological production process may require the presence of both glucose and phenylalanine in a ratio of 3:1 to proceed optimally. A sample may be monitored prior to or throughout the reaction for this relationship and the conditions may be adjusted if the observed ratio deviates from the desired 3:1 ratio.

In one aspect, the disclosure provides a method of evaluating a biological sample, including the steps of performing an NMR experiment on a component of the biological sample to obtain an NMR spectrum, performing an NIR experiment on the component of the biological sample to obtain an NIR spectrum, (the NMR and NIR experiment can be performed in any order) performing a data fusion analysis of the NIR spectrum with the NMR spectrum to generate an assigned NIR spectrum, performing an NIR experiment on the biological sample to obtain an NIR spectrum and determining the presence in the biological sample of the component of the biological sample by analyzing the NIR spectrum of the biological sample against the assigned NIR spectrum. The data fusion analysis used in the methods for evaluating a biological sample may include any of the data fusion analysis methods provided herein including OPA and SPLS. In any of the methods provided herein the data fusion analysis can be a computer-implemented step. It should also be appreciated that in any of the methods herein the determining step can also be a computer-implemented step. It should further be appreciated that the steps of obtaining the NMR and NIR spectra of the components and the data fusion analysis need not be performed in the same time frame or even at the same site as the analysis of the biological sample. For instance, the component analysis can be performed for a number of components thereby generating a library of component reference spectra that can be used to analyze NIR spectra of biological samples for the presence of the components.

In one aspect, the disclosure provides methods for evaluating a biological sample by generating a reference library of spectra that are associated with a sample with a particular outcome. For instance, spectra can be collected from samples that are known to result in a biological production process with a good yield and reference spectra can be taken from samples that are associated with a low yield. A spectrum can subsequently be taken from an unknown sample and be parsed with the library of reference spectra.

In some embodiments, a library of NIR spectra is generated by data fusion of NMR and NIR spectra of biological samples with a known outcome. NIR spectra of new samples can subsequently be compared to spectra in the library of NIR spectra to predict the outcome of a biological production process with the new sample. Thus, in some embodiments, the disclosure provides a method for evaluating a biological sample, the method comprising performing a first NIR experiment on a desired sample to obtain an NIR spectrum that correlates with a desired sample, performing a second NIR experiment on a non-desired sample to an NIR spectrum that correlates with a non-desired sample, performing an NIR experiment on the biological sample to obtain an NIR spectrum, and determining if the NIR spectrum of the biological sample correlates with the NIR spectrum of the desired sample or the NIR spectrum of the non-desired sample. In some embodiments, the determining step is a computer-implemented step. In some embodiments, the method further comprises performing a data fusion analysis of one or more of the NIR spectra with an NMR spectrum of the same sample. In some embodiments, the data fusion analysis is a computer-implemented step. It should be appreciated that the generation of the NIR reference spectra (correlating with desired and undesired samples), and the subsequent data fusion analysis with an NMR spectrum, does not necessarily need to be done at the same time/place as the generating of the NIR spectra of the biological sample. In addition, in some embodiments, the biological samples can be compared only to desired samples or only to undesired samples.

In one aspect, the disclosure provides a method for evaluating a biological sample, the method comprising performing an NIR experiment on a biological sample to obtain an NIR spectrum and comparing the NIR spectrum to a reference NIR spectrum that has undergone data fusion analysis with an NMR spectrum. In some embodiments, the comparing step is a computer-implemented step.

It should be appreciated that methods provided herein for generating the predicted NIR spectra can also be used for evaluating biological samples. In one aspect, the disclosure provides a method for evaluating a biological sample, the method comprising performing an NIR experiment on one or more components in a biological sample to obtain an NIR spectrum of the one or more components of the biological sample, performing a data fusion analysis to generate a predicted NIR spectrum, performing an NIR experiment on a biological sample to obtain an NIR spectrum, and using the predicted NIR spectrum to evaluate the NIR spectrum of the biological sample.

In one aspect, the disclosure includes a step of obtaining an NMR spectrum. NMR, as used herein, refers to a spectroscopic technique that exploits the magnetic properties of certain atomic nuclei to determine physical and chemical properties of atoms or the molecules in which they are contained. The technology relies on the phenomenon of nuclear magnetic resonance and can provide detailed information about the structure, dynamics, reaction state, and chemical environment of molecules. Typically, in NMR a tube with a solution comprising the sample to be analyzed is placed in a magnet. Radio frequency radiation of appropriate energy is broadcast into the sample. A receiver coil surrounding the sample tube monitors the radio frequency absorbed. An NMR spectrum is acquired by varying or sweeping the magnetic field over a small range while observing the radio frequency signal from the sample, or by varying the frequency of the radio frequency radiation while holding the external field constant. In some embodiments, the whole frequency range of NMR, i.e., encompassing all (proton) chemical shifts is investigated. In some embodiments, only a subset of the frequency range is investigated.

In one aspect, the disclosure includes a step of obtaining an NIR spectrum. Near-infrared spectroscopy (NIR) is a spectroscopic method that uses the near-infrared region of the electromagnetic spectrum (from about 800 nm to 2500 nm). Near-infrared spectroscopy is based on molecular overtone and combination vibrations. Typically, an NIR spectrometer includes a source, a detector, and a dispersive element (such as a prism, or more a diffraction grating) to allow the intensity at different wavelengths to be recorded. In some embodiments, the whole frequency range of NIR, i.e., encompassing all potential molecular vibrations is investigated. In some embodiments, only a subset of the frequency range is investigated.

For example, an informative subset of the NIR and/or NMR frequency range may be identified as described herein and subsequently analyzed to evaluate new samples.

It should be appreciated that methods described herein may be used for NIR and/or NMR spectra of any suitable liquid or dry (e.g., powder) samples. In some embodiments, samples may contain material for biological cultures. In some embodiments, samples may contain cells or cellular material. In some embodiments, samples may contain biological products (e.g., peptides, proteins, nucleic acids, etc., or any combination thereof). In some embodiments, samples may contain synthetic compounds. In some embodiments, samples may contain other material being evaluated. Accordingly, methods described or exemplified herein in the context of certain material or samples may be used to analyze data from other sources and/or relating to other materials or molecules.

In one aspect, certain methods comprise one or more computer-implemented steps. In some embodiments, a method for analyzing NMR and/or NIR information is provided. NMR and/or NIR data for a composition or preparation of interest can be processed on a computer that implements one or more of the analytical techniques described herein. In some embodiments, data can be stored on a computer, but data also can be retrieved from a different source. In some embodiments, one or more outputs can be displayed. However, outputs are not necessarily displayed. For example, in some embodiments an output may be used to generate a signal or message (e.g., a warning message, or a positive message)

based on the characteristics of the material being analyzed (e.g., acceptable or not acceptable for manufacture).

Figure 53:
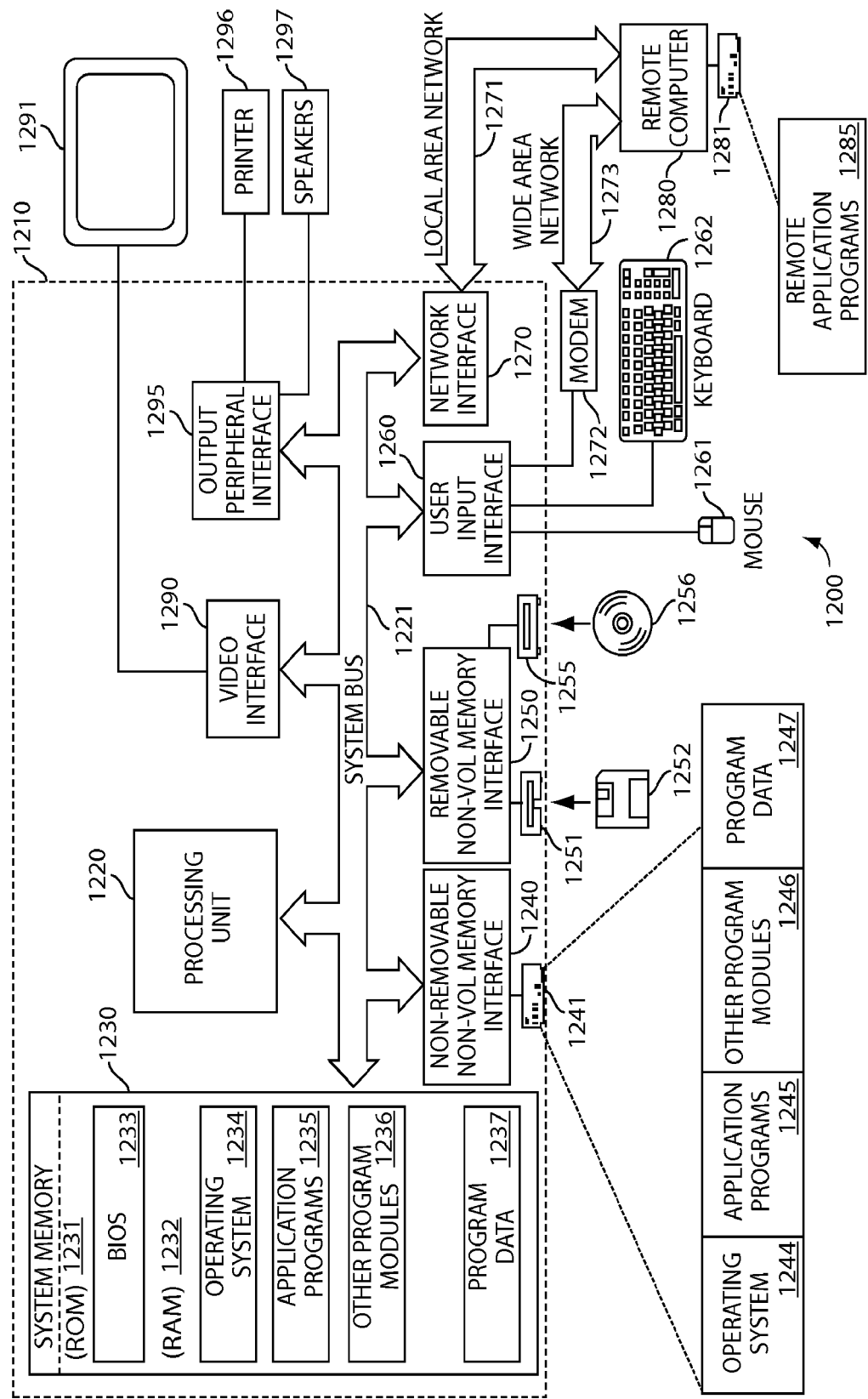
FIG. 53 shows an embodiment of a computer for use in certain methods disclosed herein.

With reference to FIG. 53, an exemplary system for implementing one or more aspects of the invention includes a general purpose computing device in the form of a computer 1210. Components of computer 1210 may include, but are not limited to, a processing unit 1220, a system memory 1230, and a system bus 1221 that couples various system components including the system memory to the processing unit 1220. The system bus 1221 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 1210 typically includes a variety of computer readable media. Computer readable media can be any available media that can be accessed by computer 1210 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 1210. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 1230 includes computer storage media in the form of volatile and/or nonvolatile memory such as read only memory (ROM) 1231 and random access memory (RAM) 1232. A basic input/output system 1233 (BIOS), containing the basic routines that help to transfer information between elements within computer 1210, such as during start-up, is typically stored in ROM 1231. RAM 1232 typically contains data and/or program modules that are immediately accessible to and/or presently being operated on by processing unit 1220. By way of example, and not limitation, FIG. 53 illustrates operating system 1234, application programs 1235, other program modules 1236, and program data 1237.

The computer 1210 may also include other removable/non-removable, volatile/nonvolatile computer storage media. By way of example only, FIG. 53 illustrates a hard disk drive 1241 that reads from or writes to non-removable, nonvolatile magnetic media, a magnetic disk drive 1251 that reads from or writes to a removable, nonvolatile magnetic disk 1252, and an optical disk drive 1255 that reads from or writes to a removable, nonvolatile optical disk 1256 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 1241 is typically connected to the system bus 1221 through an non-removable memory interface such as interface 1240, and magnetic disk drive 1251 and optical disk drive 1255 are typically connected to the system bus 1221 by a removable memory interface, such as interface 1250.

The drives and their associated computer storage media discussed above and illustrated in FIG. 53, provide storage of computer readable instructions, data structures, program modules and other data for the computer 1210. In FIG. 53, for example, hard disk drive 1241 is illustrated as storing operating system 1244, application programs 1245, other program modules 1246, and program data 1247. Note that these components can either be the same as or different from operating system 1234, application programs 1235, other program modules 1236, and program data 1237. Operating system 1244, application programs 1245, other program modules 1246, and program data 1247 are given different numbers here to illustrate that, at a minimum, they are different copies. A user may enter commands and information into the computer 1210 through input devices such as a keyboard 1262 and pointing device 1261, commonly referred to as a mouse, trackball or touch pad. Other input devices (not shown) may include a microphone, joystick, game pad, satellite dish, scanner, or the like. These and other input devices are often connected to the processing unit 1220 through a user input interface 1260 that is coupled to the system bus, but may be connected by other interface and bus structures, such as a parallel port, game port or a universal serial bus (USB). A monitor 1291 or other type of display device is also connected to the system bus 1221 via an interface, such as a video interface 1290. In addition to the monitor, computers may also include other peripheral output devices such as speakers 1297 and printer 1296, which may be connected through a output peripheral interface 1295.

The computer 1210 may operate in a networked environment using logical connections to one or more remote computers, such as a remote computer 1280. The remote computer 1280 may be a personal computer, a server, a router, a network PC, a peer device or other common network node, and typically includes many or all of the elements described above relative to the computer 1210, although only a memory storage device 1281 has been illustrated in FIG. 53. The logical connections depicted in FIG. 53 include a local area network (LAN) 1271 and a wide area network (WAN) 1273, but may also include other networks. Such networking environments are commonplace in offices, enterprise-wide computer networks, intranets and the Internet.

When used in a LAN networking environment, the computer 1210 is connected to the LAN 1271 through a network interface or adapter 1270. When used in a WAN networking environment, the computer 1210 typically includes a modem 1272 or other means for establishing communications over the WAN 1273, such as the Internet. The modem 1272, which may be internal or external, may be connected to the system bus 1221 via the user input interface 1260, or other appropriate mechanism. In a networked environment, program modules depicted relative to the computer 1210, or portions thereof, may be stored in the remote memory storage device. By way of example, and not limitation, FIG. 53 illustrates remote application programs 1285 as residing on memory device 1281. It will be appreciated that the network connections shown are exemplary and other means of establishing a communications link between the computers may be used.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove.

EXAMPLES

Example 1

Materials and Methods

Samples and Controls

Glutamine (gln), glucose, and phenylalanine (phe) were all ACS reagent grade obtained from Sigma Aldrich. d4-Trimethyl-silyl propionate was obtained from Sigma Aldrich. $D_2O$ was obtained from Cambridge Isotopes Lab. Samples of gln, glucose, and phe were combined following the factorial design shown in Table 1.

TABLE 1

Composition of samples used to demonstrate the principal of OPA and sequential PLS for biopharmaceutical applications

| Class | Gln (mM) | Glucose (mM) | Phe (mM) |
|---|---|---|---|
| A | 10 | 0 | 0 |
| B | 0 | 10 | 0 |
| C | 0 | 0 | 10 |
| D | 5 | 5 | 0 |
| E | 5 | 0 | 5 |
| F | 0 | 5 | 5 |
| G | 6.67 | 1.67 | 1.67 |
| H | 1.67 | 6.67 | 1.67 |
| I | 1.67 | 1.67 | 6.67 |
| J | 3.33 | 3.33 | 3.33 |

Dulbecco modified eagle medium (DMEM) samples were acquired from Sigma-Aldrich or Hyclone. Exposure to atmosphere was minimized to reduce water adsorption. Moisture levels were measured using Karl Fischer titration (Mettler Toledo) with 105° C. sample heating.

NIR Acquisition Parameters

NIR spectra were obtained using a Bruker MPA spectrometer equipped with an integrating sphere and lead-sulfide detector for powder samples. Spectra were acquired by co-adding 128 spectra at 2 $cm^{-1}$ resolution with a reference spectrum obtained using 256 spectra. Reference spectra were re-acquired every hour to reduce drift. Liquid samples were measured in a transmission cell with 5 mm path length cuvette and an InGaAs detector. Samples were equilibrated in the instrument 6 minutes prior to acquisition to stabilize temperature. For liquid samples, 256 scans were added with a phase resolution of 32 $cm^{-1}$. All spectra were acquired using OPUS software version 6.5 (Bruker Optics, Billerica, Mass.).

NMR Acquisition Parameters

NMR spectra were obtained using a 500 MHz Avance II Spectrometer (Bruker BioSpin, Billerica, Mass.) equipped with a cryogenic probe. Samples contained 10% $D_2O$ with 1 mM TSP.

TABLE 2

NMR acquisition settings

| Parameter | Setting |
|---|---|
| D1 | 3 sec |
| Sample Tubes | 5 mm outer diameter Bruker tubes |
| Number of Scans | 128 |
| Shim | Topshim |
| Size of FID | 32768, 65536 |
| Experiment | ;zgesgp; avance-version (09/04/17); 1D sequence; water suppression using excitation sculpting with gradients T.-L. Hwang & A. J. Shaka, J. Magn. Reson. Series A 112 275-279 (1995) zg30; avance-version (10/02/09); 1D sequence; using 30 degree flip angle |

Yield Data

Process yield and other product quality attributes were obtained based on protein concentration and volume measurements. Each DMEM vendor lot was used to make between one to nine product batches in unique combination with other raw materials.

Data Processing

Software

NMR acquisition was controlled using TopSpin version 3.0 (Bruker). Spectra were transformed and processed using a real spectrum of 65536 points, line broadening of 0.3, auto phase and baseline correction. Spectra were transferred to MatLab version 7 (Mathworks, Natick, Mass.) for preprocessing, partial-least squares and principal component analysis with PLSToolbox ver 3.5 (Eigenvector Research, Wenatchee, Wash.).

Data Fusion Techniques

Preprocessing

NMR spectra were first normalized to the total area, baseline corrected using Weighted Least Squares (WLS), and, finally, mean-centered. NIR spectra were corrected using Extended Multiplicative Scatter Correction (EMSC), normalized to total area and then mean centered. The data was prepared for the Outer Product Analysis (OPA) by shifting and normalizing the spectra so that the minimum is 0 and the maximum is 1 (Code is shown in FIGS. 12-15).

Combination of Regression and VIP Plot

The regression vector and variable importance in projection (VIP) provide two different types of information. The regression vector shows which variables positively and negatively correlate with the Y block while the VIP array shows the degree of importance of such variable. In order to combine both types of information in one plot, the two arrays were multiplied to preserve the sign of the regression vector while emphasizing the magnitude information of the VIP array. In the case of data fusion, a two dimensional plot was displayed as an image using the imagesc graphing function of Matlab.

Outer-Product Analysis

Figure 10:
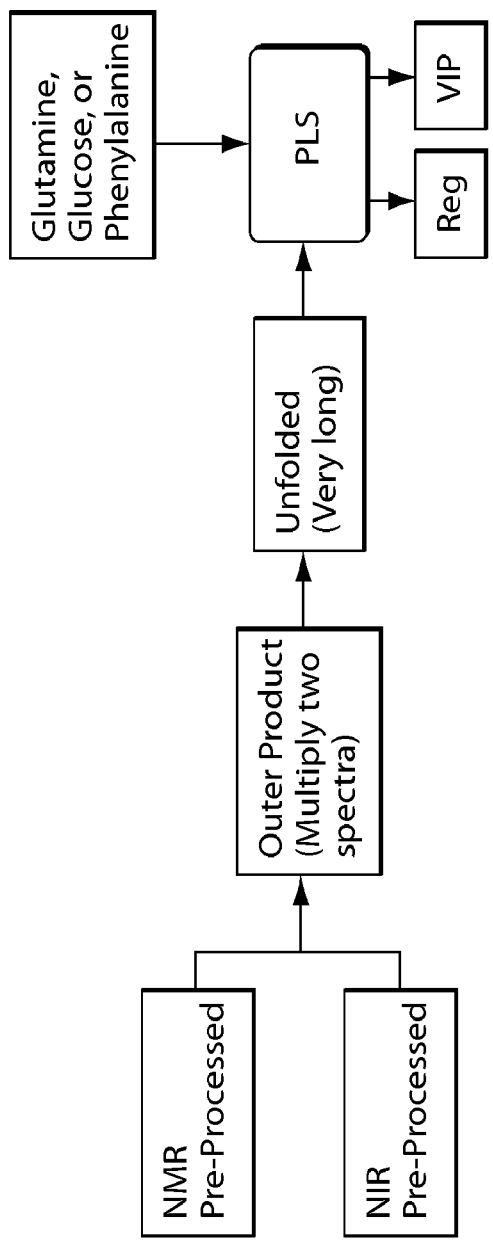
FIG. 10 shows an outer-product flow diagram.

FIG. 10 shows an outer-product flow diagram. Outer-product analysis was performed as described (Rutledge, D. N.; Barros, A. S.; Giangiacomo, *R. Spec. Publ.—R. Soc. Chem. Special Publication—Royal Society of Chemistry* 2001, 262, 179-192). The outer product of the NMR and NIR spectra was calculated by multiplying each NMR and NIR spectral point together (code shown in FIGS. 12-13). The dataset was then used as the X block of the PLS along with the concentration of GLN, glucose or PHE as the Y block. The model was then calculated with venetian blind cross-validation. The regression vector and variable importance in projection (VIP) were multiplied to produce a combined array. The code is shown in FIG. 14. Furthermore, the resulting array was then reshaped from a one dimensional array to a two dimensional matrix for visualization and interpretation.

Sequential PLS

For sequential PLS, the pre-processed NMR spectra were used as the x-block in the sequential PLS, while the pre-processed NIR spectra were used as the y-block (FIG. 11A). The sequential PLS model was calculated using 3 latent variables (LV). The regression vector, variable importance in projection plot (VIP) and predictions were extracted from the calculated model. The regression vector was unfolded then multiplied by the unfolded VIP to produce a combination vector. This vector was then folded back to produces a combination image that shows the correlation between the NMR and NIR spectra.

Figure 11:
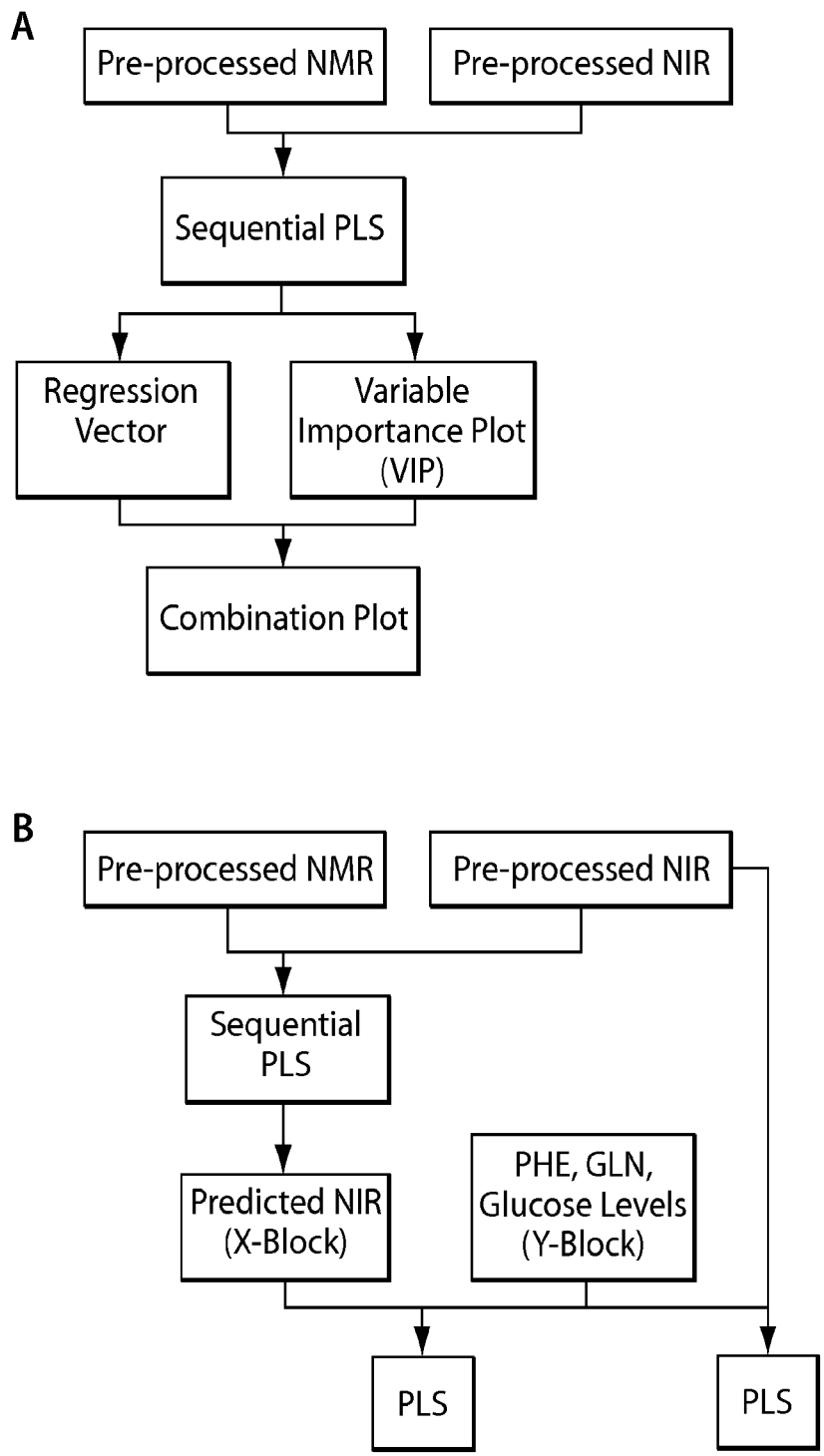
FIG. 11 shows a flow diagram illustrating the difference between sequential PLS and standard PLS.
Figure 17:
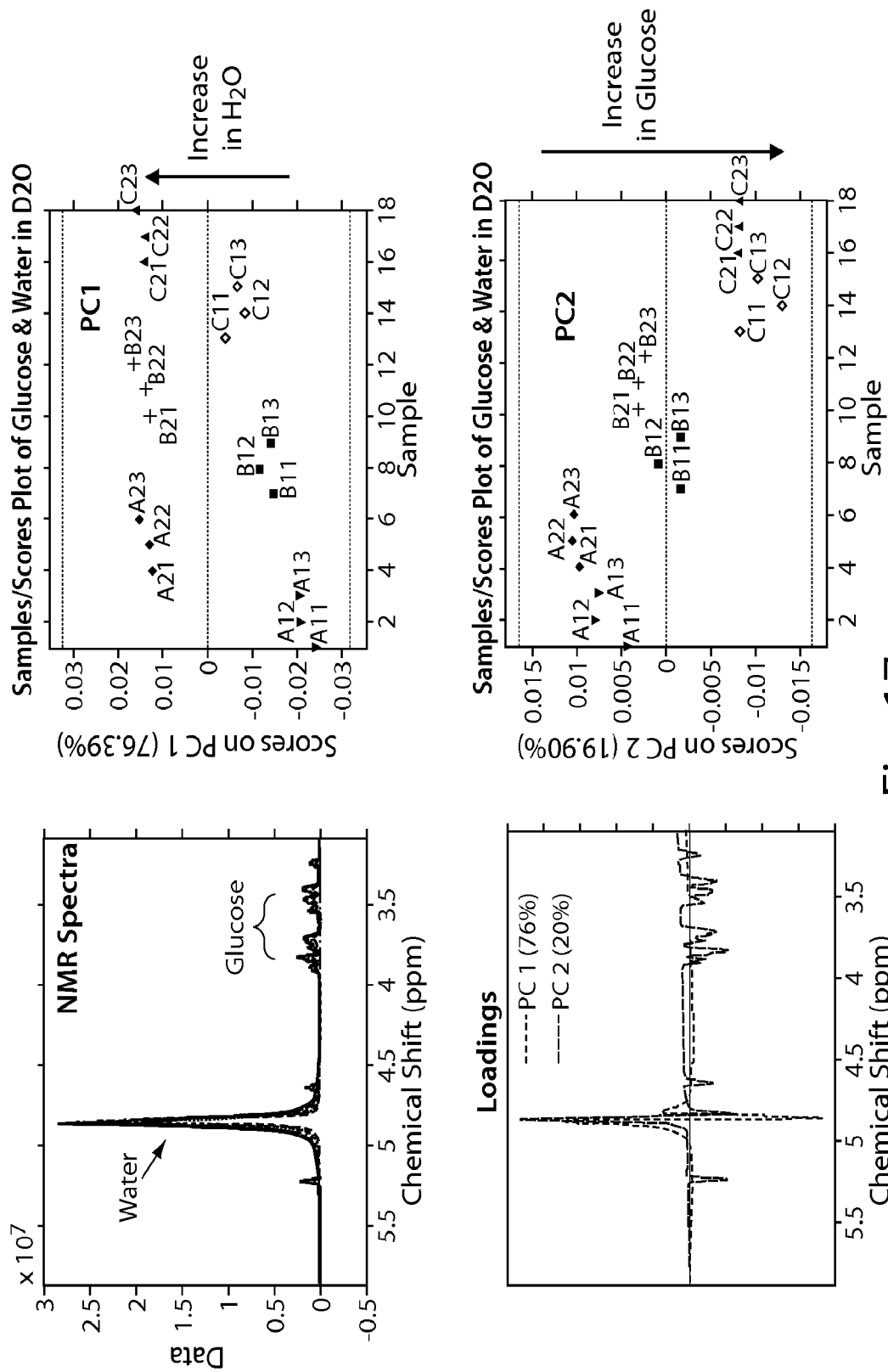
FIG. 17 shows an NMR of glucose/water samples.
Figure 18:
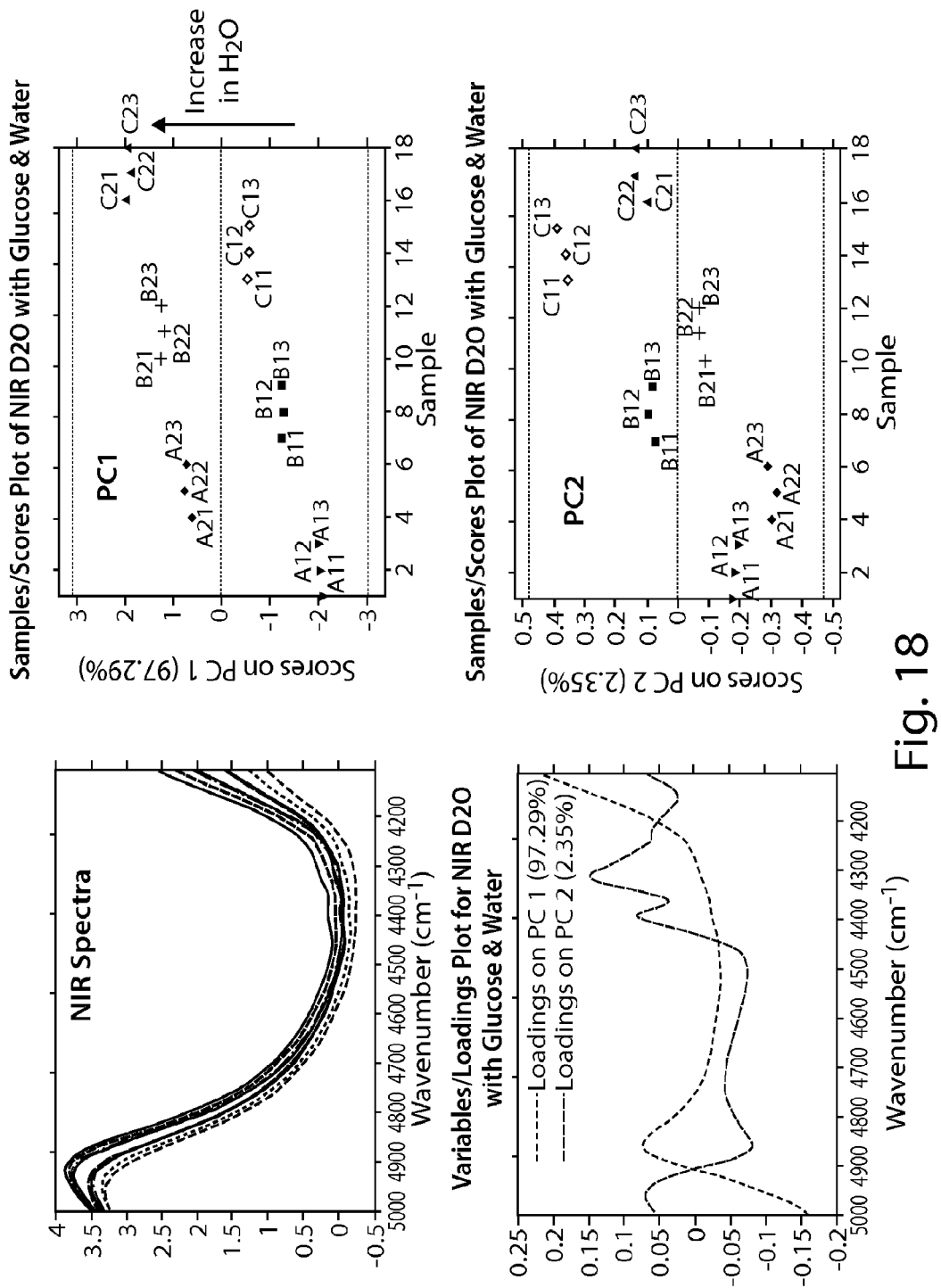
FIG. 18 shows liquid NIR spectra and a Principal Component Analysis (PCA) of glucose and water.
Figure 19:
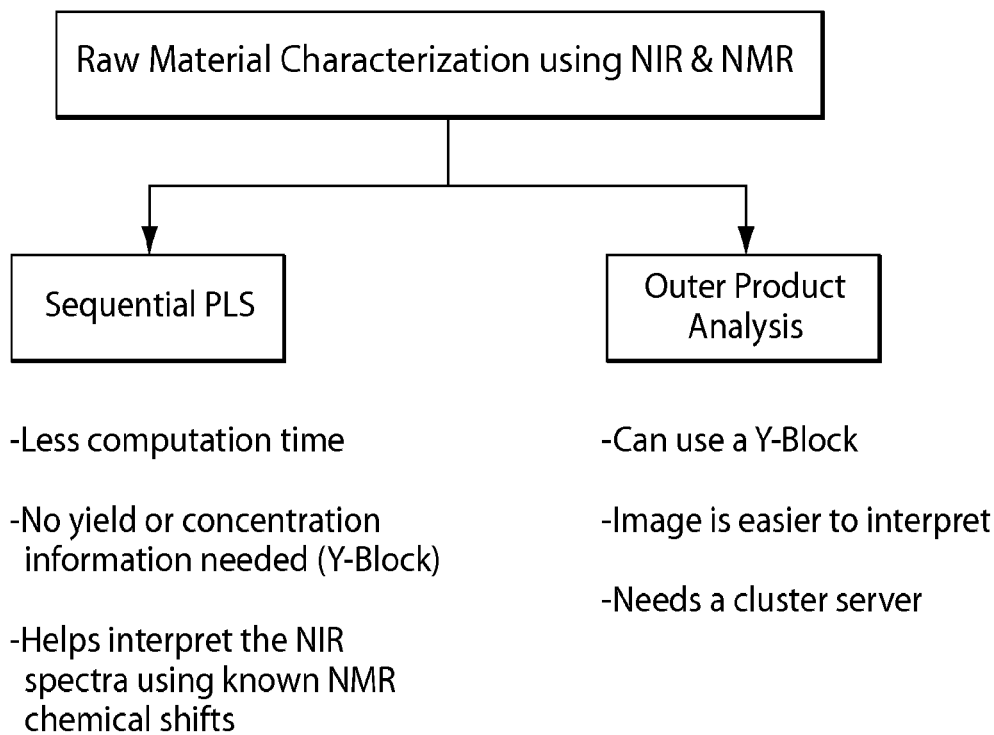
FIG. 19 provides an overview of a strategy to combine NMR and NIR spectral analysis.
Figure 20:
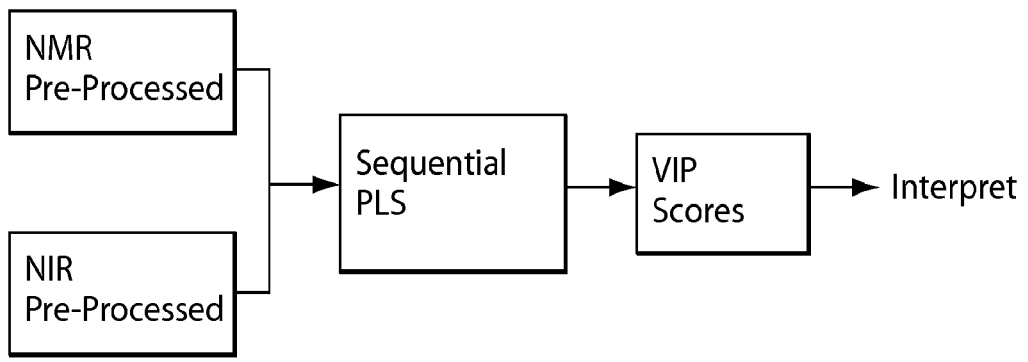
FIG. 20 provides an overview of a Sequential Partial Least Squares (SPLS) analysis.
Figure 21:
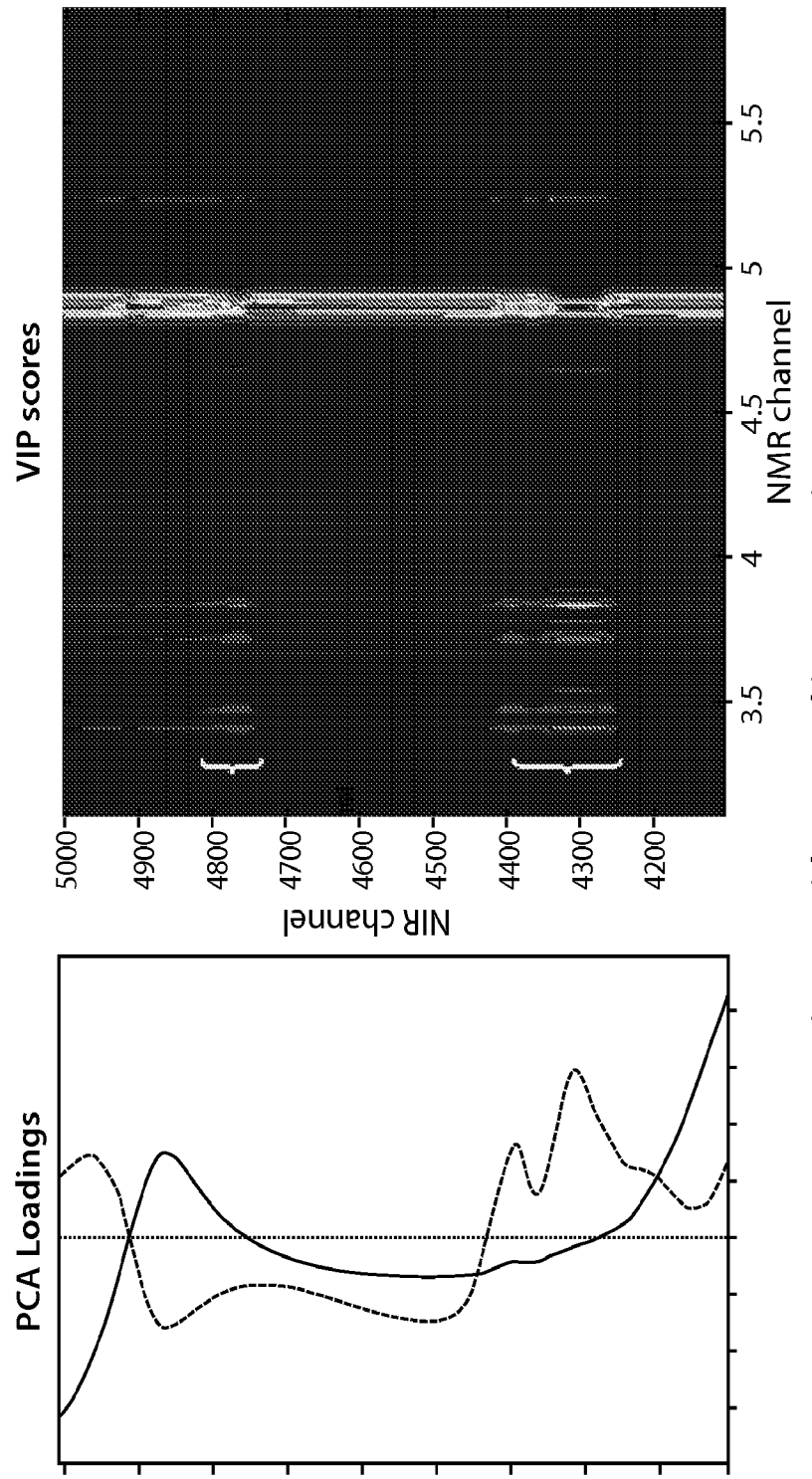
FIG. 21 provides an overview of a Sequential Partial Least Squares analysis of glucose and water.
Figure 23:
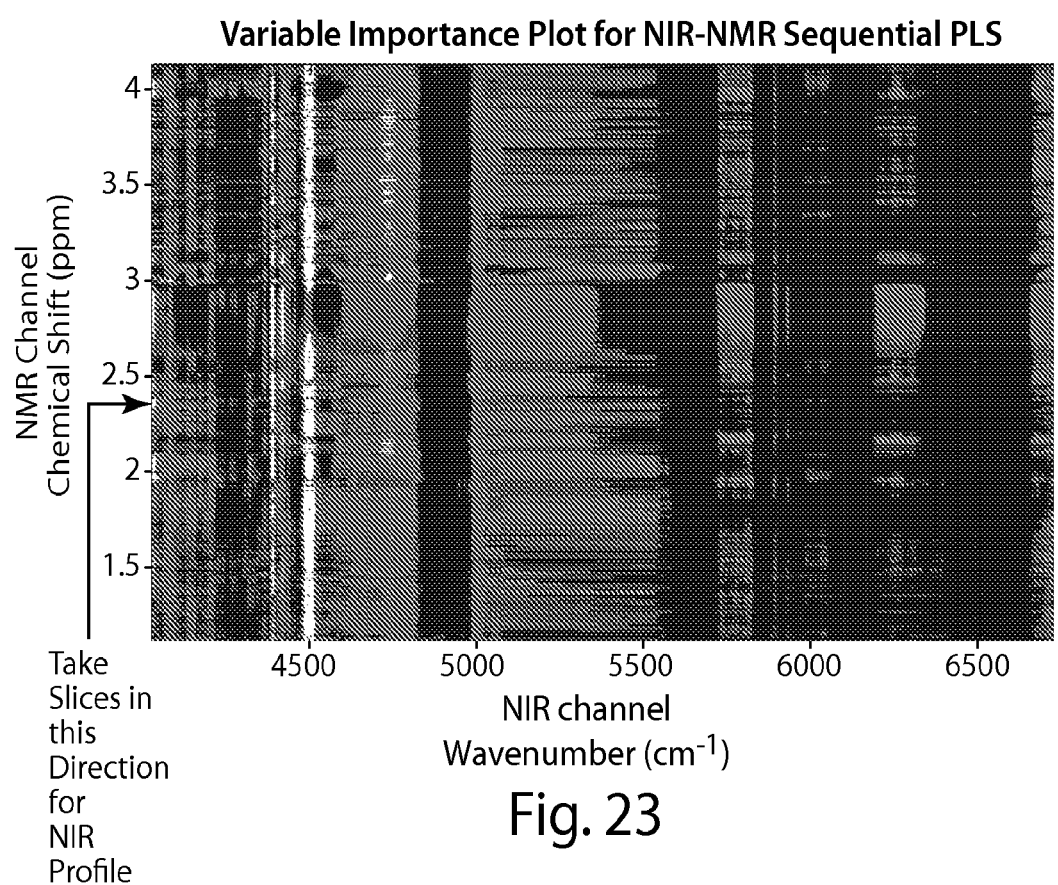
FIG. 23 provides a factorial mix of DMEM components with a VIP image using Partial Least Squares analysis.
Figure 24:
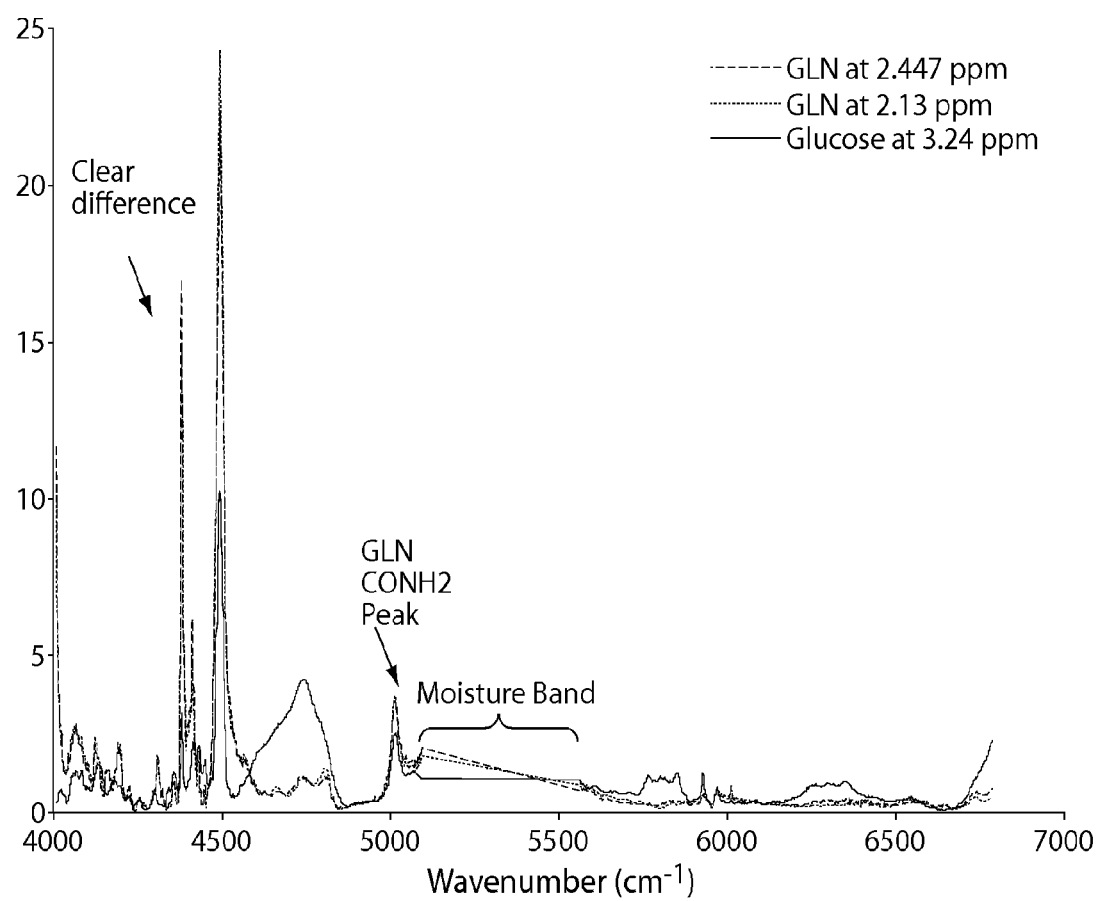
FIG. 24 provides NIR profiles from the Sequential Partial Least Squares variable importance plot for mix of DMEM components.
Figure 25:
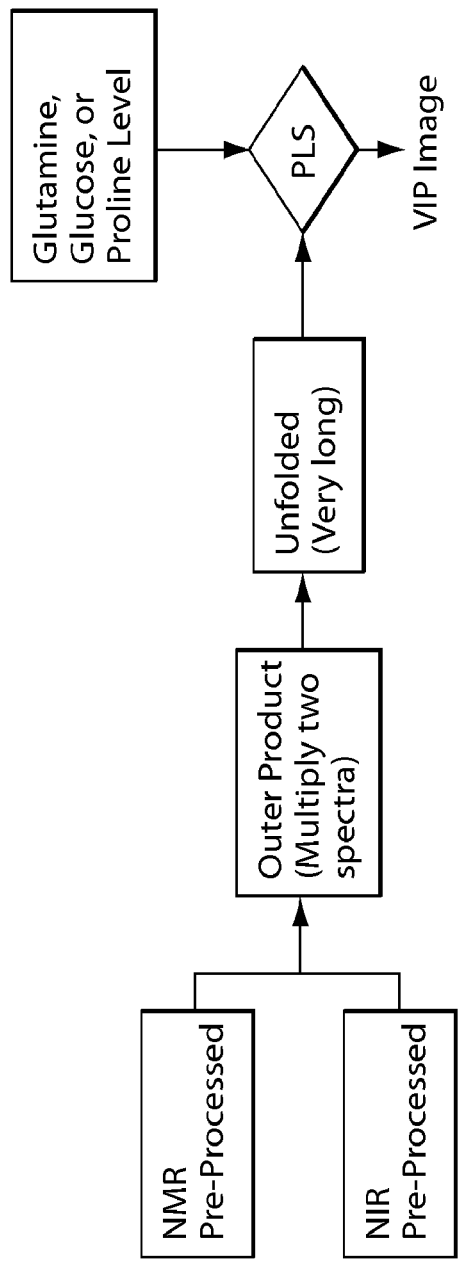
FIG. 25 provides an overview of Outer Product Analysis.
Figure 26:
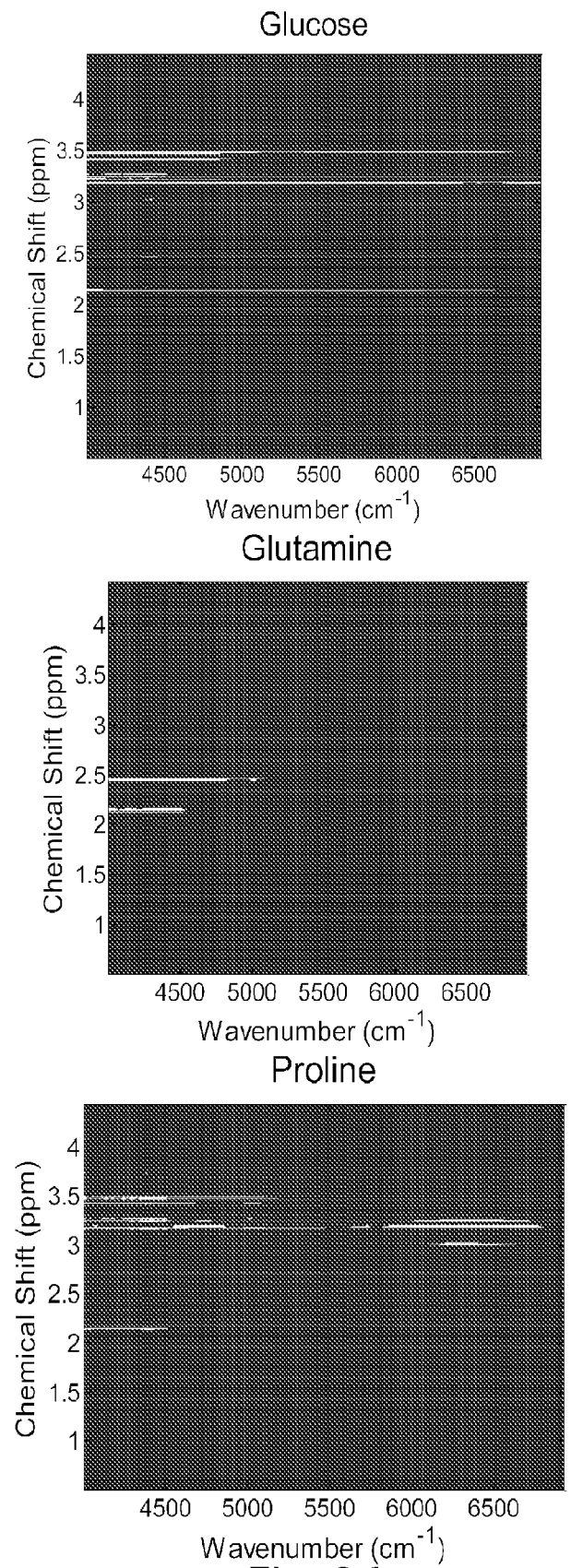
FIG. 26 provides Outer Product VIP Images for a mix of DMEM components.
Figure 27:
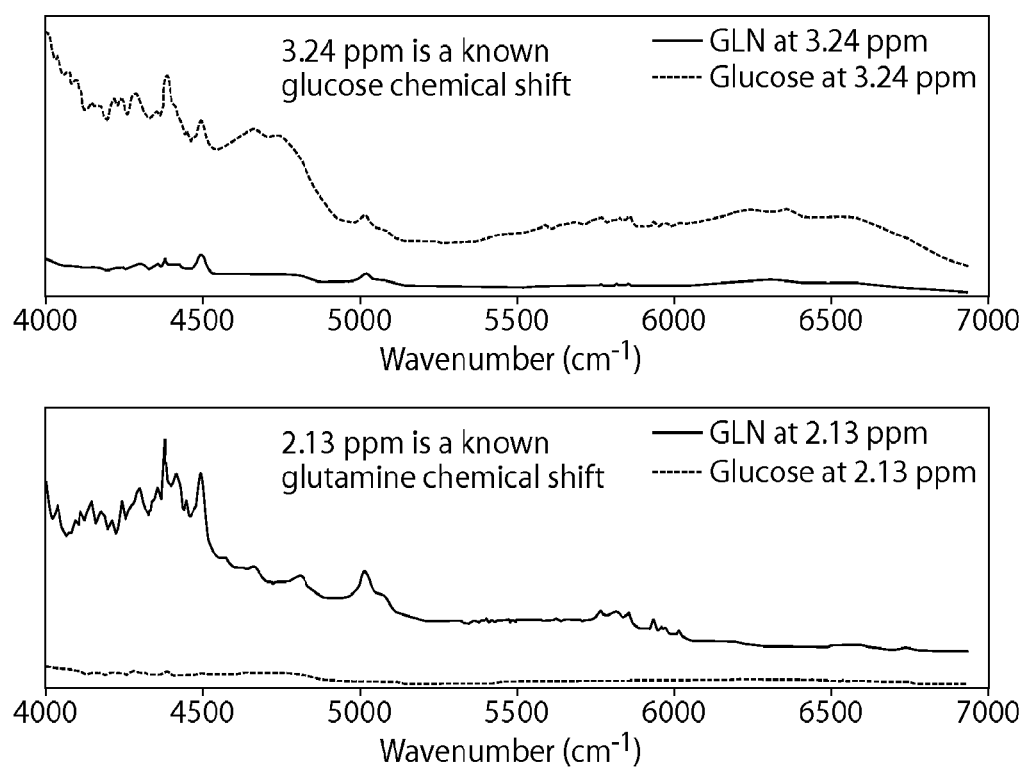
FIG. 27 provides NIR profiles for a DMEM component mix.

FIG. 11 shows a flow diagram illustrating the use of sequential PLS to characterize the NIR spectra using the NMR spectra. The NIR predictions from the 3 LV PLS model were calculated for each NIR wavelength from which a set of predicted NIR spectra were obtained (See FIG. 11B). These predictions were used in turn as the x-block of a subsequent PLS where the concentrations of PHE, GLN and glucose in each sample were used in turn as the y-blocks. The pre-processed NIR spectra were also used directly as the x-block in PLS models to use as a comparison. The code is depicted in FIG. 15.

Results and Discussion

Glutamine, Glucose, Phenylalanine NMR and NIR Spectra

Original and pre-processed NMR and NIR spectra are shown in FIGS. 1 and 2. Regions of the NMR spectra associated with water are excluded. Only $2^{nd}$ and $3^{rd}$ overtone regions of the NIR spectra are included.

Figure 33A:
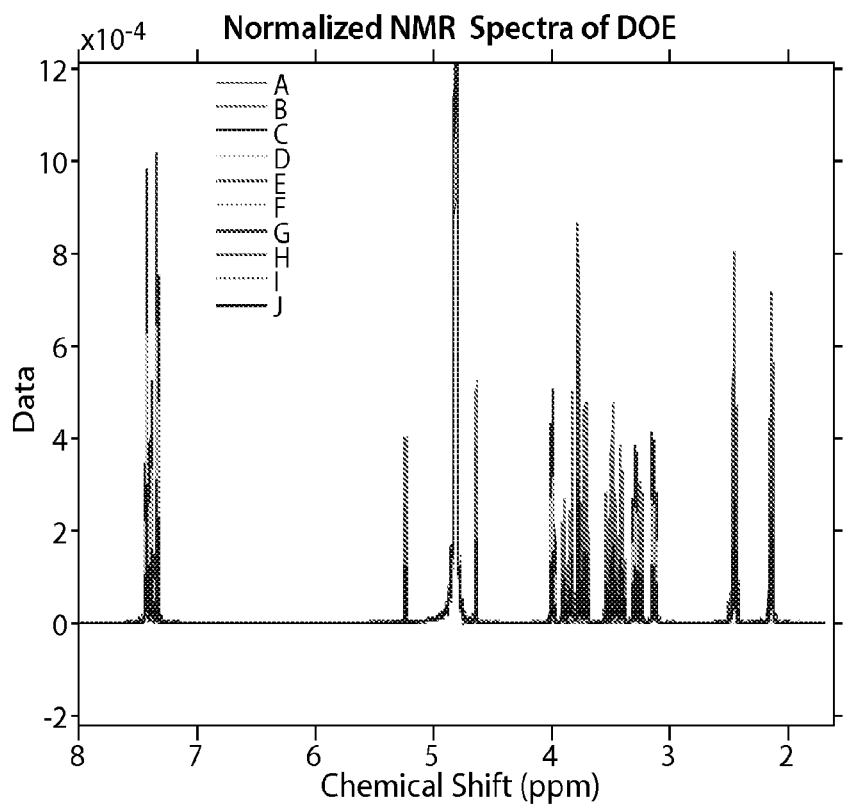
Figure 33B:
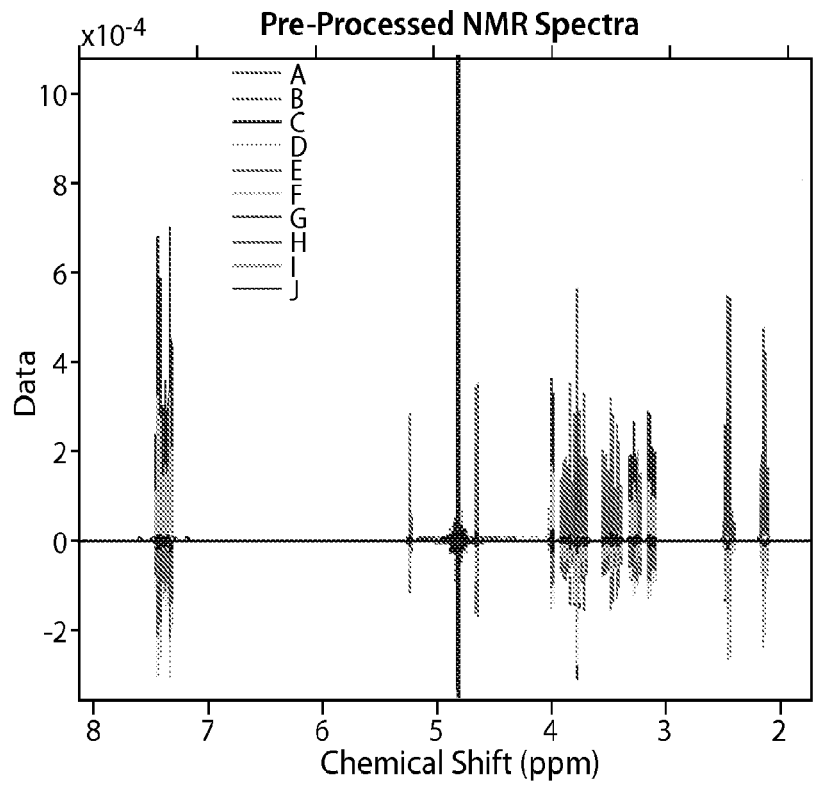
FIG. 33B shows the NMR spectra after preprocessing. Regions of the NMR spectra associated with water are excluded. Only combination band region of the NIR spectra are included.
Figure 34A:
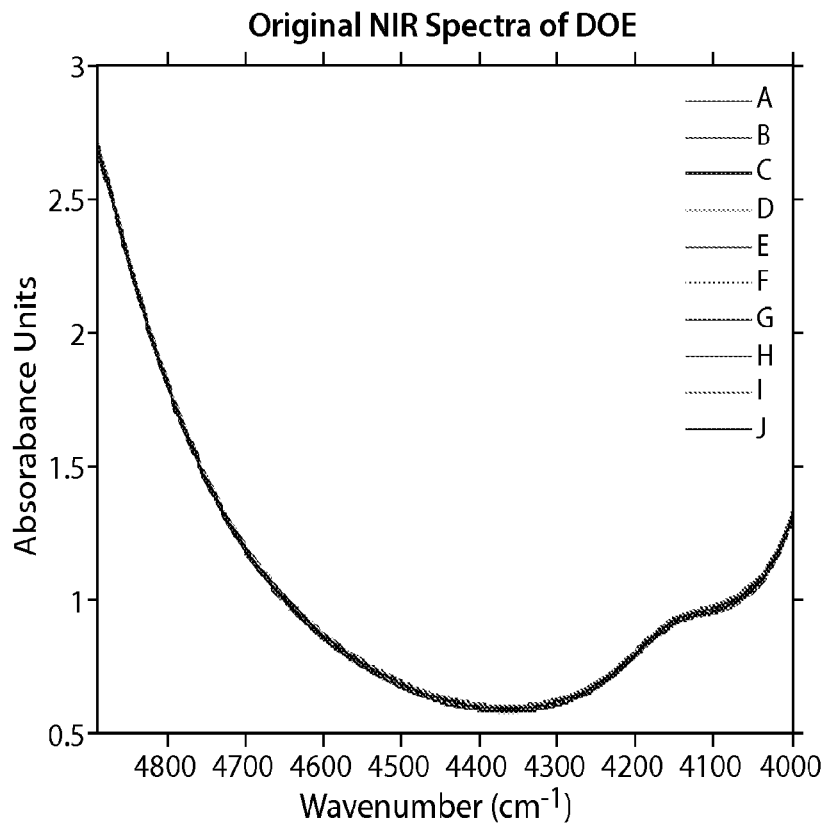
Figure 34B:
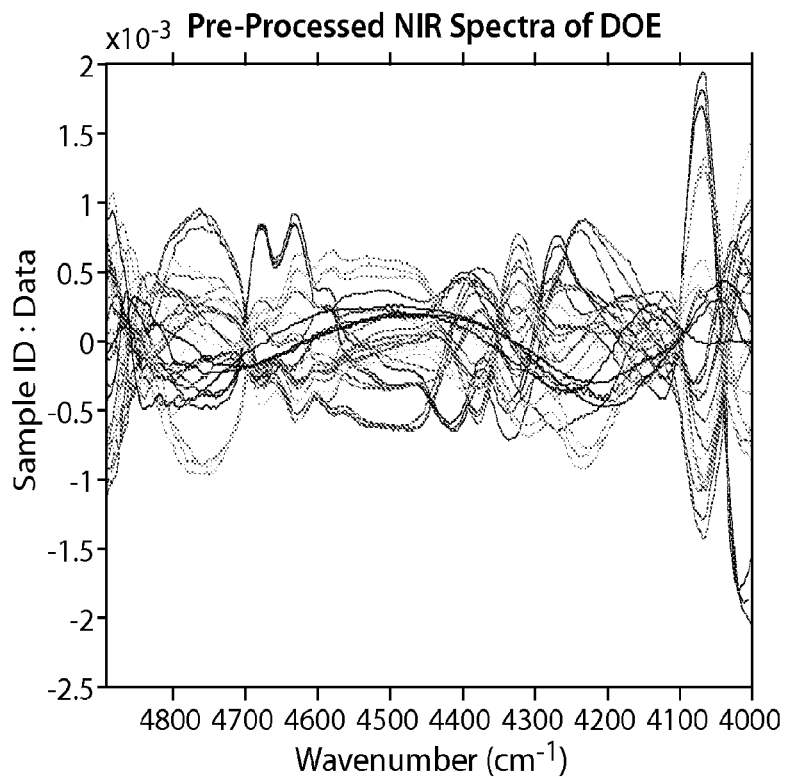
FIG. 34B shows the NIR spectra after preprocessing. The pre-processed NIR spectra were smoothed using a Savitzky-Golay filter with 15 point smoothing.

Original and pre-processed NMR and NIR spectra are also shown in FIGS. 33 and 34. Regions of the NMR spectra associated with water are excluded. Only combination band region of the NIR spectra are included. The pre-processed NIR spectra were smoothed using a Savitzky-Golay filter with 15 point smoothing.

Combination of Regression and VIP Plot Results

Outer product analysis indicated which NMR chemical shifts correspond with specific vibrational signals in the NIR for each component of the mixture. In separate models, one for each component in the three-component mixture, a clear qualitative picture was obtained. To access this information, three types of graphical strategies were compared in FIG. 3. By multiplying the regression vector and the VIP values, clearer assignment of the NIR and NMR peak relationships was possible than by using either vector independently. To illustrate this concept, NMR profile slices at 8755 $cm^{-1}$ from the PHE model results were displayed in three ways: the combined regression vector multiplied by VIP plot, regression vector only and VIP vector only. FIG. 3A shows the combined plot for PHE. The PHE chemical shifts can be clearly distinguished because of the positive sign and high magnitude of the peaks. FIG. 3B shows the VIP plot only for PHE. Only the magnitude of the peaks can be seen and thus, it is harder to distinguish the PHE peaks from the glucose and GLN chemical shifts. FIG. 3C shows the regression vector for PHE. Similarly, it is difficult to determine the correlation of PHE with this display because the VIP magnitude information is missing from the plot. This can be seen especially in the region from 3 to 4 ppm where the peaks of glucose, GLN and PHE overlap and are close together. Inspection shows that a plot that combines the regression vector and the VIP improves the interpretability of the NMR and NIR profiles.

Result Visualization

Figure 4:
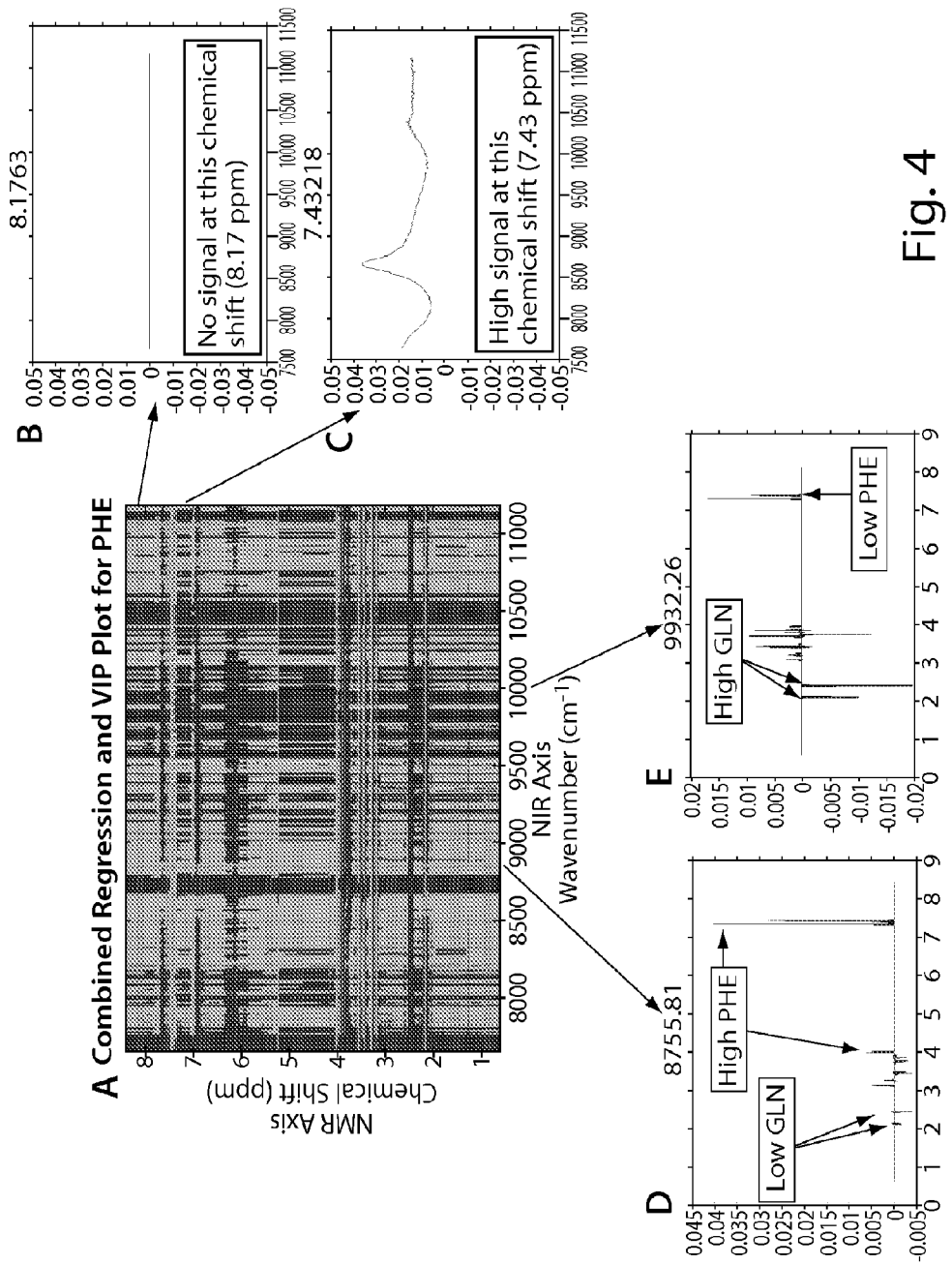
FIG. 4 shows the result from the OPA PLS with PHE level as the Y Block.
Figure 5:
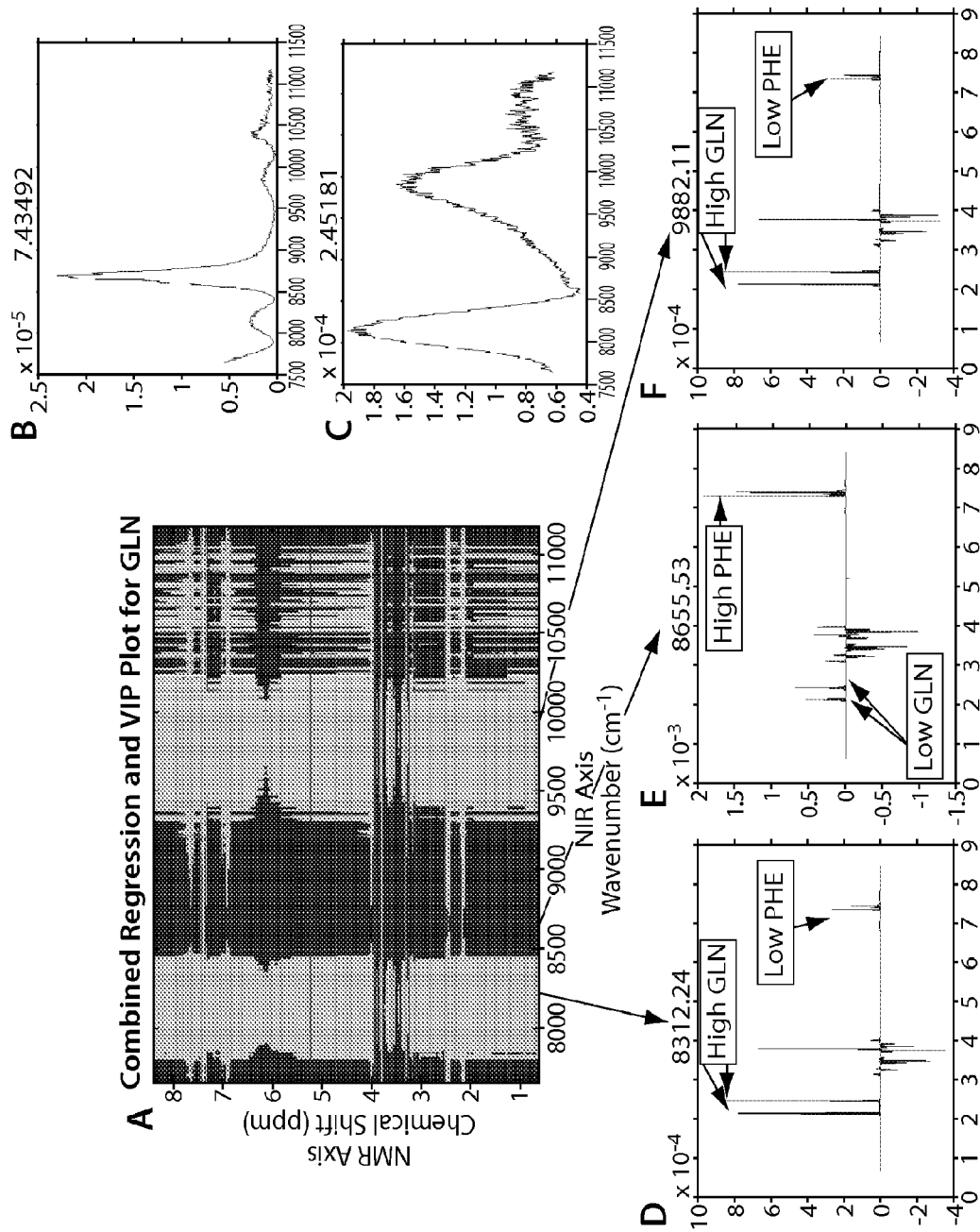
FIG. 5 shows the result from the OPA PLS with GLN level as the Y Block.
Figure 6:
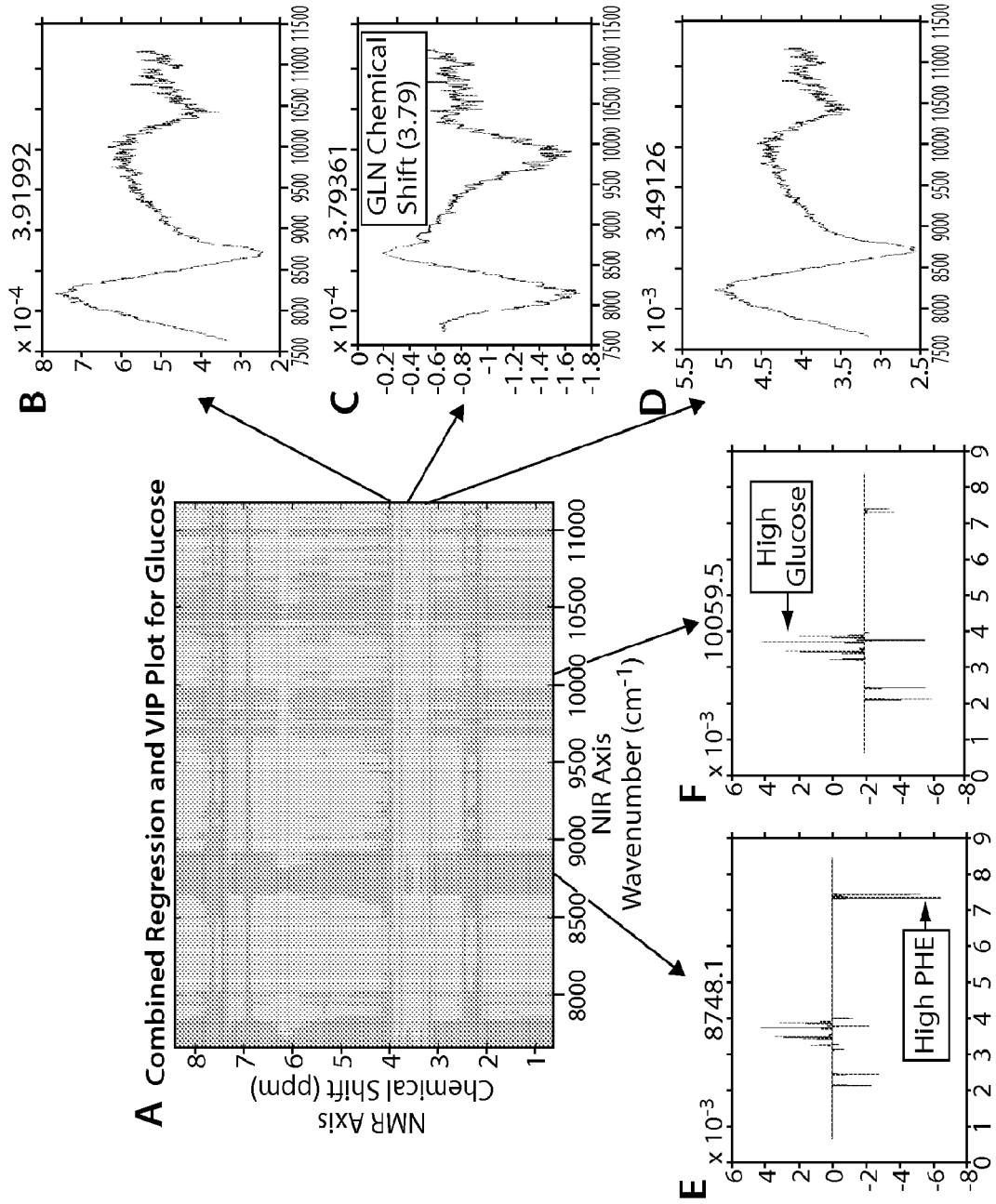
FIG. 6 shows the result from the OPA PLS with glucose level as the Y Block.

When the combined regression vector-VIP matrix was considered as an image, even more information became accessible. FIGS. 4-6 illustrate this for OPA-PLS models for PHE, GLN and glucose. OPA enables intuitive understanding of disparate data sets.

FIG. 4A shows an image of the combined VIP and regression matrix obtained from multiplying the regression and the variable importance images from a PLS of the outer-product. The image shows the changes in intensity and signs associated with the total contribution to the OPA-PLS model. To understand how a combined VIP-regression image can be used, FIGS. 4B-E show specific NIR wavelength and NMR chemical shift channels in FIG. 4A. For example, FIG. 4B, shows that no NIR peaks are associated with 8.17 ppm because there are no NMR peaks at that chemical shift. However, FIG. 4C which corresponds to 7.43 ppm in the NMR spectra, has a distinct peak in the NIR between 8500 and 9000 $cm^{-1}$. The chemical shift at 7.43 is related to the NIR peak from aromatic protons in PHE. Looking along the NIR axes, different NMR chemical shifts are emphasized at different NIR wavelengths. In FIG. 4D, which corresponds to the NIR wavenumber 8755.81 $cm^{-1}$, the NMR peaks pertaining to PHE are high in magnitude and positively correlated to the Y-block of the PLS. The region of 8700's $cm^{-1}$ is also known to be a region with strong aromatic absorption which reaffirms the validity of this method (Workman Jr., J.; Weyer, L. *Practical Guide to Interpretive Near-Infrared Spectroscopy*, $1^{st}$ ed.; CRC Press: Boca Raton, Fla., 2008). In contrast, FIG. 4E shows a NIR wavenumber that does not have a strong correlation with PHE; however, it has a correlation with GLN with chemical shifts at 2.1, 2.4 and 3.7 ppm.

FIGS. 5B-F show slices along NMR and NIR axes of the combined GLN matrix, FIG. 5A. FIG. 5B shows that the slice of the NMR at 7.43 ppm, which is a known PHE chemical shift, reaffirms the findings from the combined matrix of PHE. The wavenumbers 8500 to 9000 $cm^{-1}$ are still important for PHE. FIG. 5C also shows the NIR slice for a known GLN chemical shift (2.45 ppm) which shows that the peaks near 8000 $cm^{-1}$ and 9700 $cm^{-1}$ are important for GLN. FIGS. 5D, 5E and 5F show the NMR profile along three different NIR wavenumbers: 8312 ($CH_2$), 8655 (aromatic) and 9882 $cm^{-1}$ (amine). Each figure shows which compound is important at that specific wavenumber. FIG. 5D shows that GLN is clearly important because of its positive sign and high magnitude at 8312 $cm^{-1}$.

FIGS. 6A-F show similar results for glucose. FIG. 6A is the combined matrix image where glucose concentration was used as the Y block for the PLS model. In FIGS. 6B and 6D, the NIR profile shows a high correlation for glucose at 3.91 and 3.49 ppm, which are known to be glucose chemical shifts. The NIR profile has a high and positive magnitude, and therefore, shows a high correlation with the NMR chemical shifts, especially at 8,400 and 10,000 $cm^{-1}$ (CH and $CH_2OH$; Workman Jr., J.; Weyer, L. *Practical Guide to Interpretive Near-Infrared Spectroscopy*, $1^{st}$ ed.; CRC Press: Boca Raton, Fla., 2008).

Sequential PLS

The regression vector and VIP were extracted from the 3 LV sequential PLS model resulting from using the NMR and NIR of the Gln, glucose and Phe. The two arrays were unfolded and then multiplied to compute the combination array that was folded and plotted as shown in FIG. 28A. The combination image shows the areas where the NMR chemical shifts correlate with the NIR wavenumbers.

Figure 28:
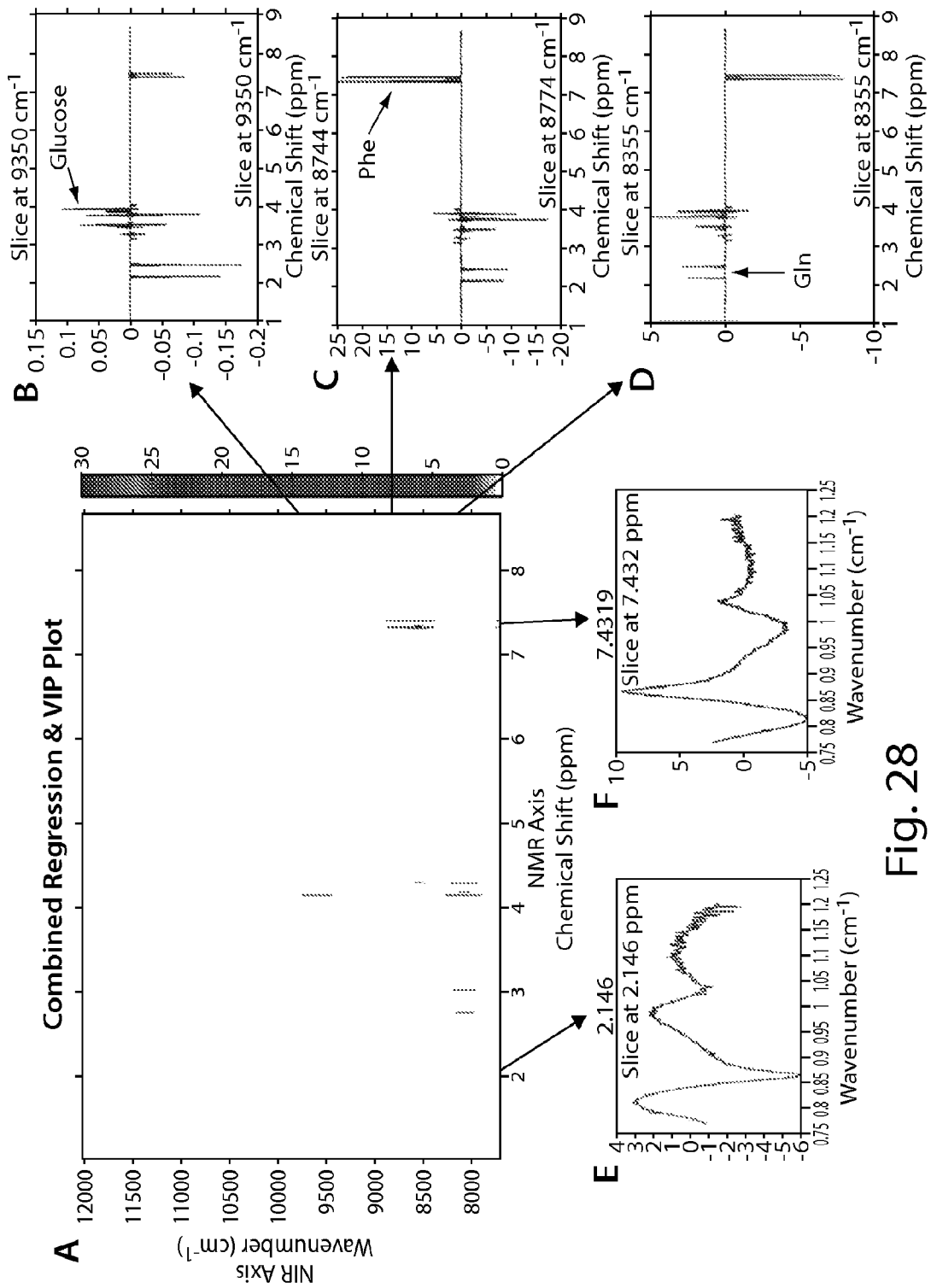
FIG. 28 shows the results of a combination vector using sequential PLS.

FIG. 28-B shows a slice through the NMR axis at 9350 $cm^{-1}$ showing a positive correlation to the glucose chemical shifts. This band is known as the OH with hydrogen bonding band and thus would certainly be correlated to glucose. Similarly, FIG. 28-C shows a slice through the NMR axis at 8744 cm$^{-1}$ indicating a positive correlation with the Phe chemical shifts. This band is also known as the CH aromatic band. Furthermore, FIG. 28-D shows a slice through the NMR axis at 8355 cm$^{-1}$ showing a correlation with the Gln chemical shifts. This band is also known as the C—H$_2$ methylene band and Gln would certainly have absorption at this band. Similarly, FIGS. 28-E and 28-F show the slices through the NIR at 2.14 ppm (Gln peak) and 7.43 ppm (Phe peak) respectively. This furthermore validates the results of the OPA shown in FIG. 4C for Phe and FIG. 5C for Gln. Both the sequential PLS and the OPA highlight the same important areas in the NIR that correlate with the Gln, glucose and Phe NMR spectra.

Figure 35:
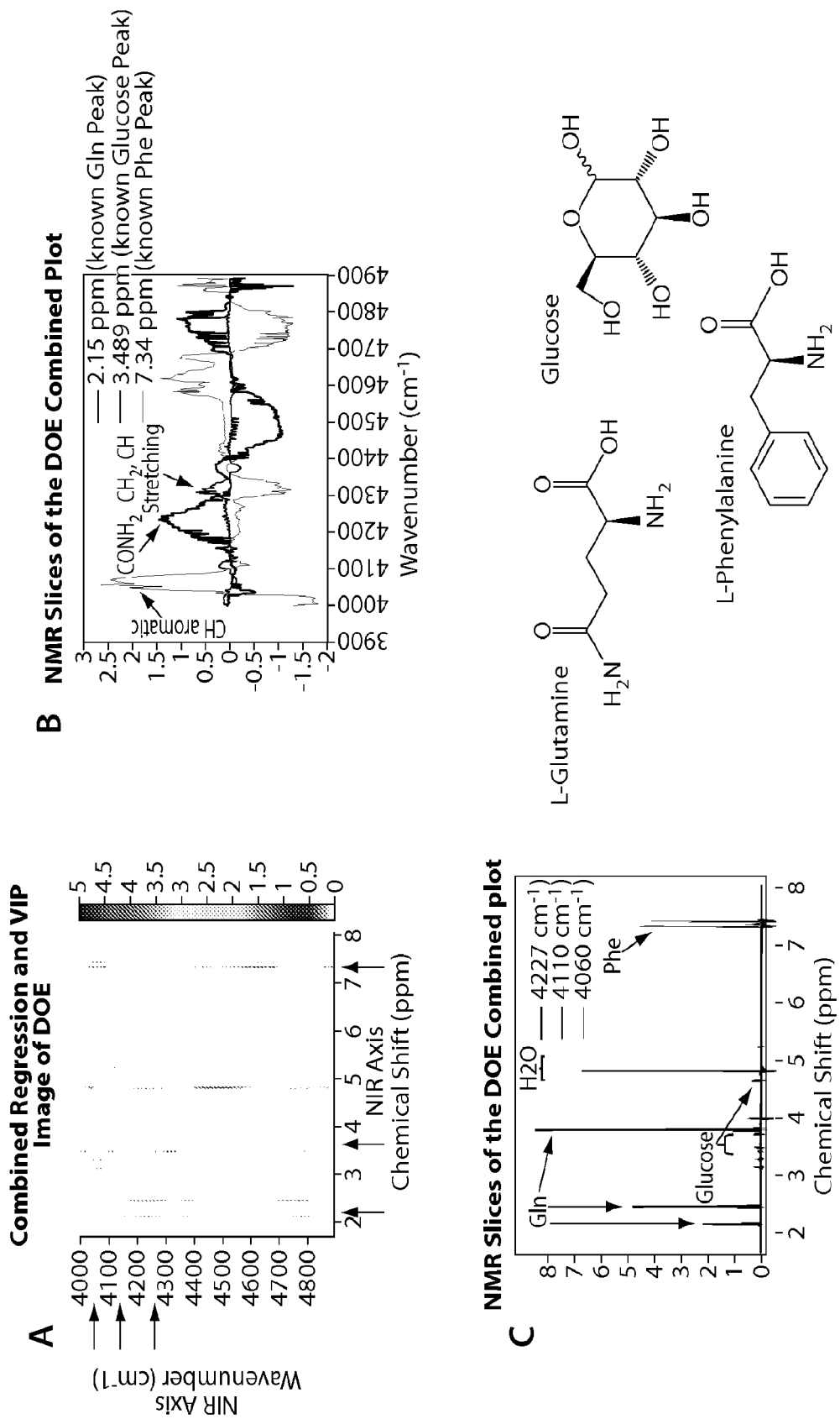
FIG. 35 shows the results of a combination vector using sequential PLS.

Sequential PLS results are also provided in FIG. 35. The regression vector and VIP were extracted from the sequential PLS model resulting from using the NMR and NIR of the gln, glucose and phe mixtures. The two arrays were multiplied to compute the combination array that was plotted and shown in FIG. 35-A. The combination image shows the areas where the NMR chemical shifts correlate with the NIR wavenumbers.

When the combined regression vector-VIP matrix is considered as an image, even more information becomes accessible. FIG. 35-A shows the combined regression and VIP image resulting from the sequential PLS highlighting the chemical shifts of the NMR that correlate with the NIR wavenumbers. Slices of this image were taken and displayed in FIG. 35-B and FIG. 35-C. FIG. 35-B shows slices of the NMR axis. Gln has a signature NMR peak at 2.15 ppm which is shown in blue. Similarly, glucose has a unique NMR chemical shift at 3.49 ppm shown in green. Phe also has a signature chemical shift in the aromatic region at 7.34 ppm shown in red. The gln profile shows a positive correlation at 4376 cm−1 which is the absorbance band for CONH$_2$. From observing the structure of gln, this should be a unique absorbance for the amine group present in the amino acid. Also, the NIR peak present at 4235 cm−1 highlighting a positive correlation to gln is known to be due to the C—H methylene group which is also evident in the gln structure. The glucose profile shown in FIG. 35-B in green also shows similar positive correlations in the CH—CH$_2$ interaction as well as CH—CC region at 4312 cm−1 and 4112 cm−1, respectively. In addition, the phe profile highlighted in red in FIG. 35-B shows positive correlation in the regions 4056 cm−1 and 4623 cm−1 which are known to be the CH-aromatic region which can be seen from the structure of phe. This correlation can also be confirmed when observing the NIR slices in FIG. 35-C showing the absorption bands of gln in blue, glucose in green and phe in red. Gln possesses NMR chemical shifts at 2.15, 2.45 and 3.78 ppm. When analyzing the NIR slice at 4227 cm−1, the gln chemical shifts appear to be positively correlated while all the other chemical shifts are not. The glucose chemical shifts are also highlighted in green with a positive correlation in the NIR absorption of 4110 cm−1 and phe chemical shifts, especially in the aromatic region (7.34 ppm) are shown with a positive correlation at 4060 cm−1. This method, therefore, provides an accurate as well as specific way to highlight which absorption bands correlate with which compound and their respective chemical shifts without further knowledge of the chemical concentrations and compound information.

Figure 7:
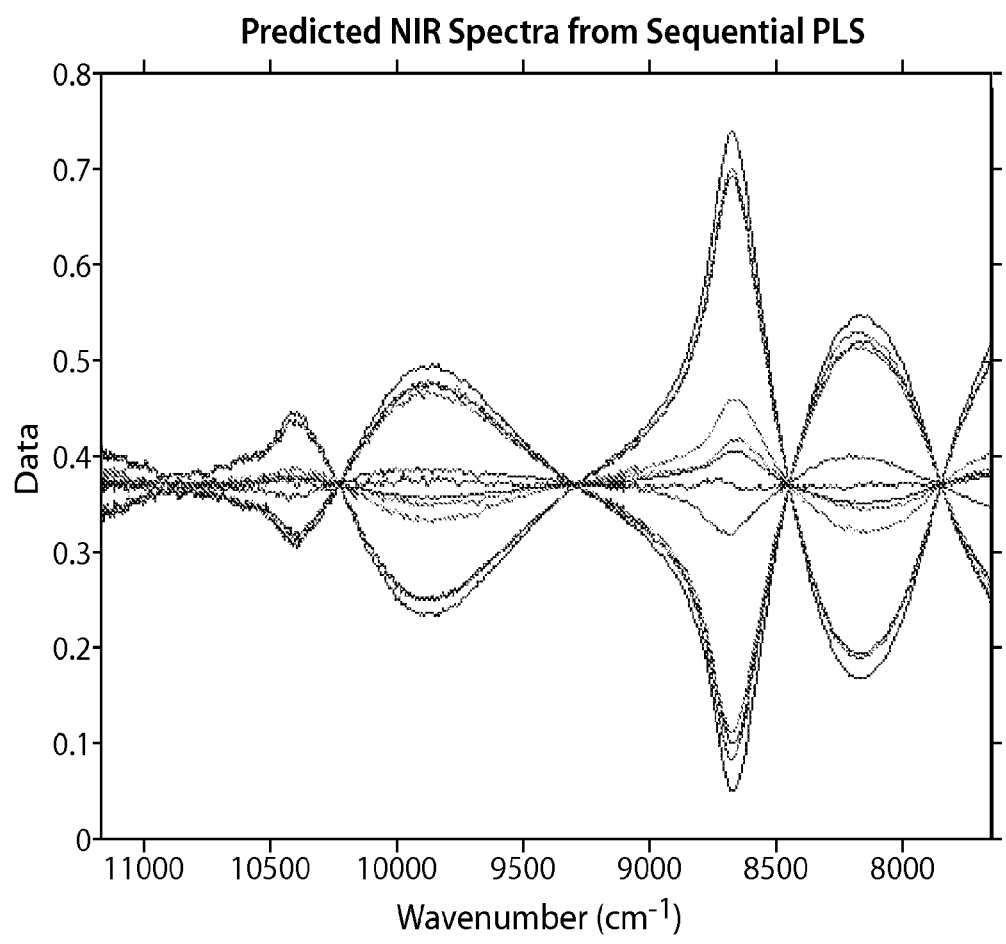
FIG. 7 shows the predicted NIR spectra from sequential PLS models with NMR of the same sample.

The sequential PLS models also produces a predicted NIR spectrum. The average predicted NIR spectra for each wavelength are shown in FIG. 7. Comparison with the original NIR spectra, FIG. 2B, reveals both improved signal-to-noise in the predicted spectra as well as a significant re-organization of the intensity patterns. There is more clustering of predicted NIR intensities at disparate values than found in the original spectra.

The impact of using NMR in combination with NIR to predict NIR spectra is shown in Table 3. Using the predicted NIR spectra instead of the original pre-processed spectra produced PLS models with either better Pearson's correlation coefficients, less over-fitting or both. Table 3 shows the values of the model R$^2$, root mean squared error of calibration (RMSEC), root mean squared error of cross validation (RMSECV) and number of latent variables (LV) included. In the case of all three compounds, the values of the RMSEC and RMSECV are closer together; therefore, showing a higher quality, better fitting model when predicted NIR spectra are used in place of original data. Using the predicted NIR spectra also provided the ability to keep more latent variables (LV); therefore, producing a more comprehensive model with minimum error.

TABLE 3

Comparison of models for GLN, PHE and glucose for predicted versus regularly pre-processed NIR spectra.

| Compound | X-Block | R$^2$ | RMSEC | RMSECV | LV |
|---|---|---|---|---|---|
| PHE | Predicted | 0.96 | 0.341 | 0.556 | 4 |
|  | Original | 0.85 | 0.683 | 1.987 | 2 |
| GLN | Predicted | 0.94 | 0.516 | 0.842 | 4 |
|  | Original | 0.88 | 0.751 | 1.583 | 2 |
| Glucose | Predicted | 0.92 | 3.461 | 4.246 | 2 |
|  | Original | 0.94 | 3.030 | 5.889 | 2 |

DMEM Example

Figure 8:
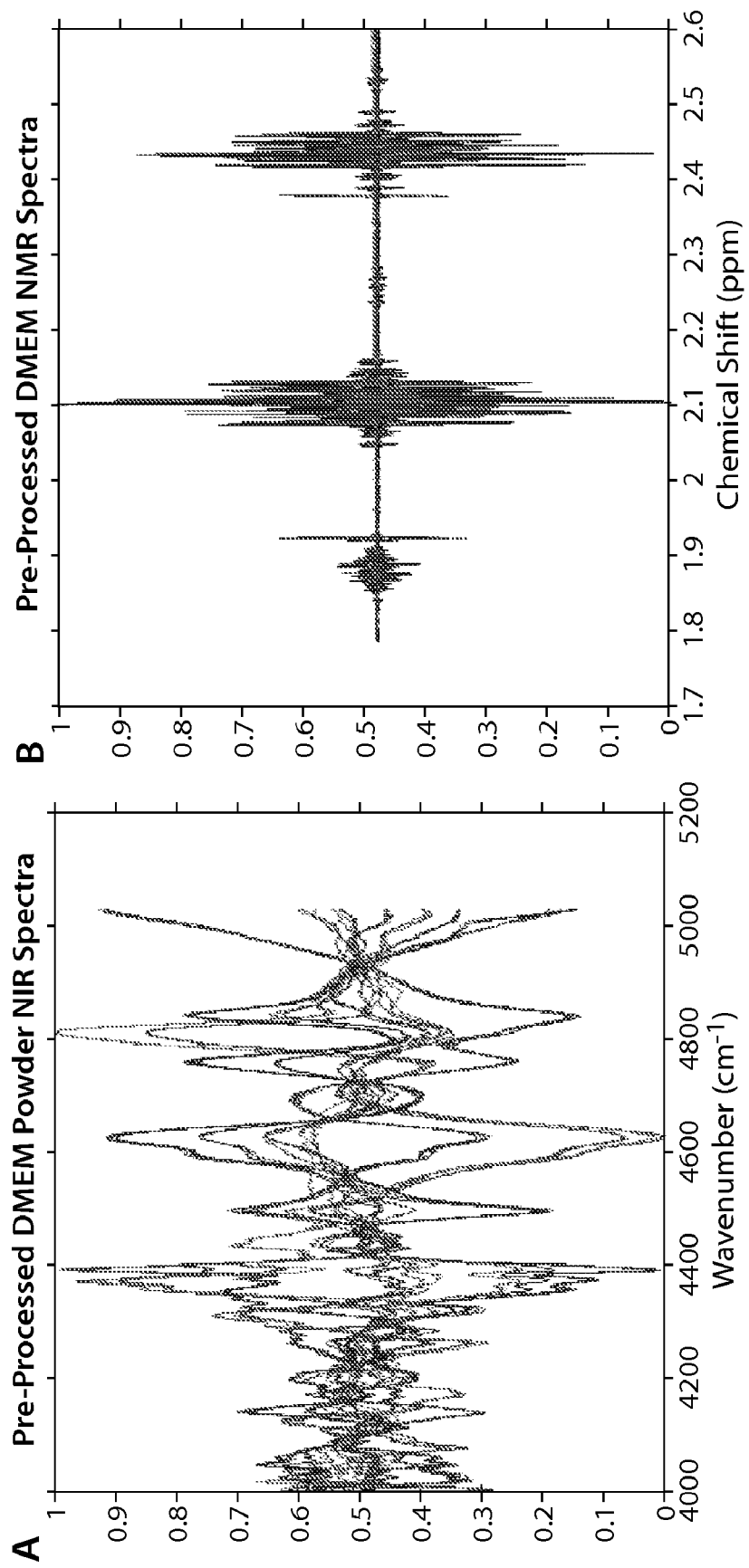
FIG. 8 shows an overlay of triplicate pre-processed (A) NIR spectra and (B) NMR spectra of 12 DMEM vendor lot samples.

FIG. 8 shows a set of DMEM NMR and NIR raw and pre-processed spectra. The NMR region between 1.7 to 2.6 ppm is used in the outer product analysis while the region between 4000 and 5029 cm$^{-1}$ were used for the NIR.

Figure 9:
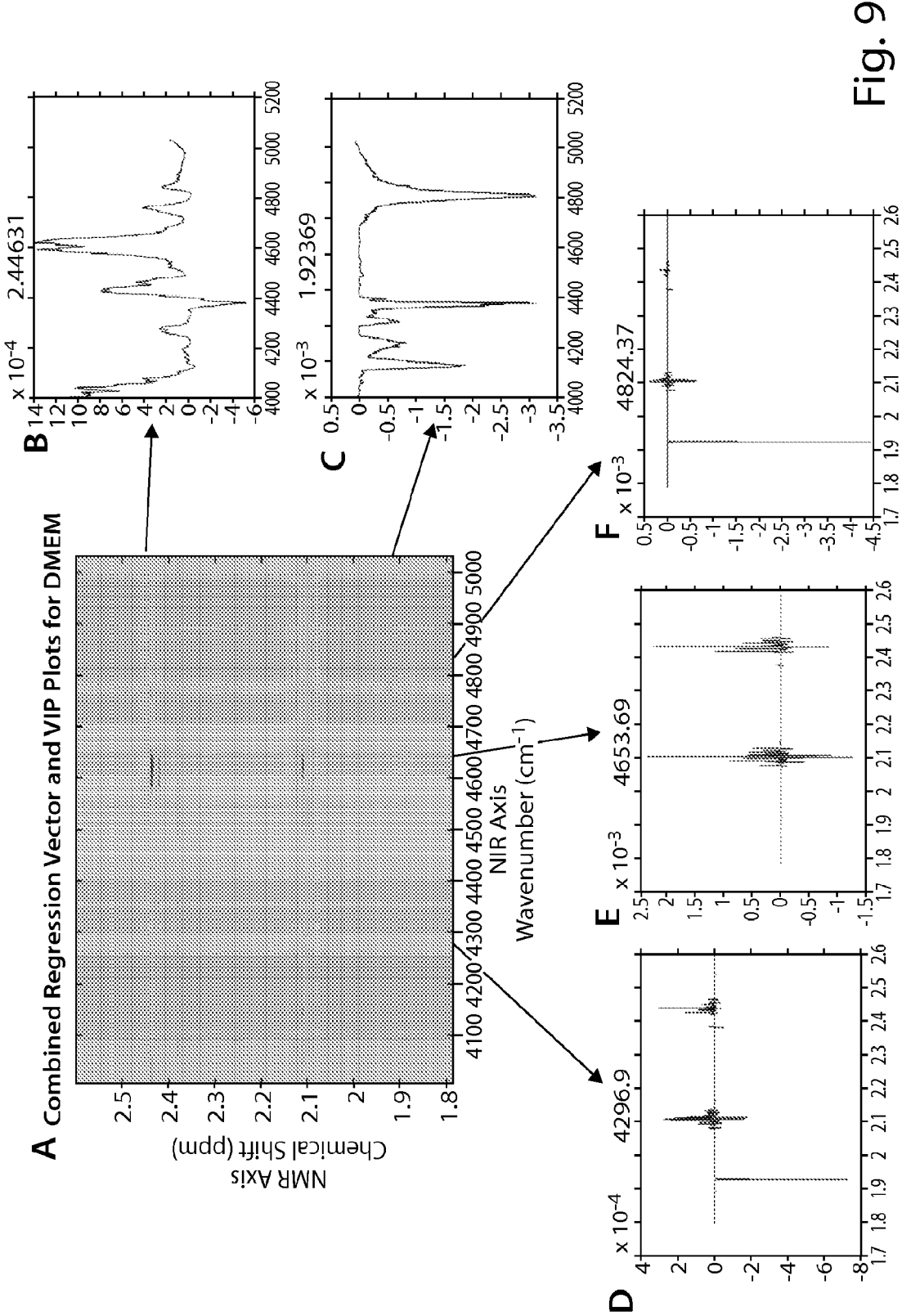
FIG. 9 shows an outer product analysis between the NIR combination band region and aliphatic NMR region for spectra of DMEM vendor lots.

FIG. 9A shows an image of the DMEM combined regression vector and VIP obtained from the PLS of the NIR-NMR outer product results and protein yield. FIG. 9B shows the NMR at 2.44 ppm, which is a known GLN chemical shift showing a high positive correlation in the region of the NIR between 4500 cm$^{-1}$ and 4700 cm$^{-1}$. FIG. 9C shows another NMR slice at 1.92 ppm which has a high negative correlation in the NIR region 4790 cm$^{-1}$ to 4850 cm$^{-1}$. FIGS. 9D and 9F show the NIR slices at 4296.9 cm$^{-1}$ and 4824.4 cm$^{-1}$ respectively, which indicates a high negative correlation with the NMR peak at 1.92 ppm. This indicates that this specific NMR shift negatively correlates with those two NIR absorption regions. Similarly, FIG. 9E shows the NIR slice at 4653.7 cm$^{-1}$ indicating a high positive correlation with the GLN peaks at 2.44 ppm and 2.1 ppm.

Outer Product Analysis (OPA) Results

Figure 29:
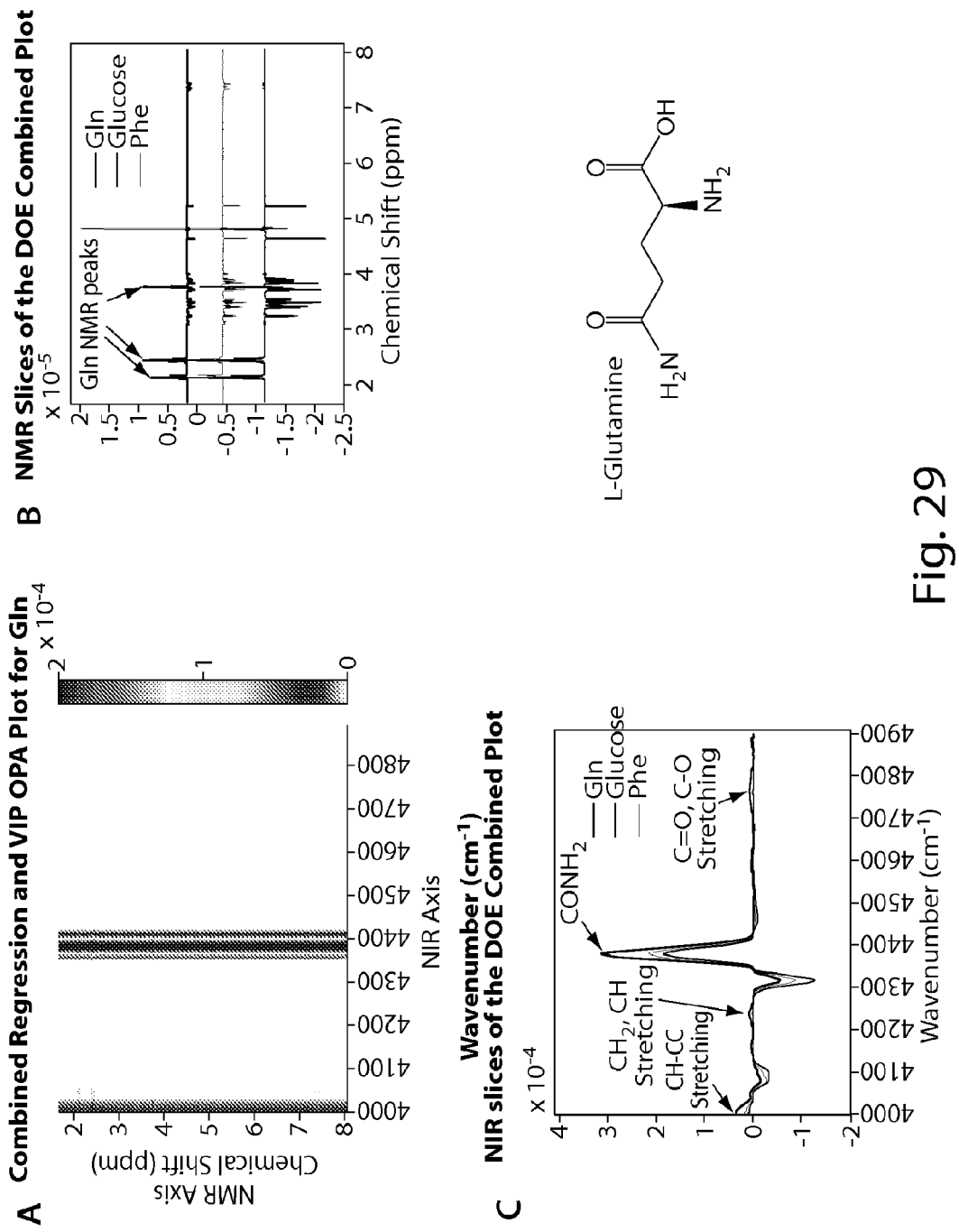
FIG. 29 shows the outer-product results from the PLS with Gln concentration as the Y Block.
Figure 30:
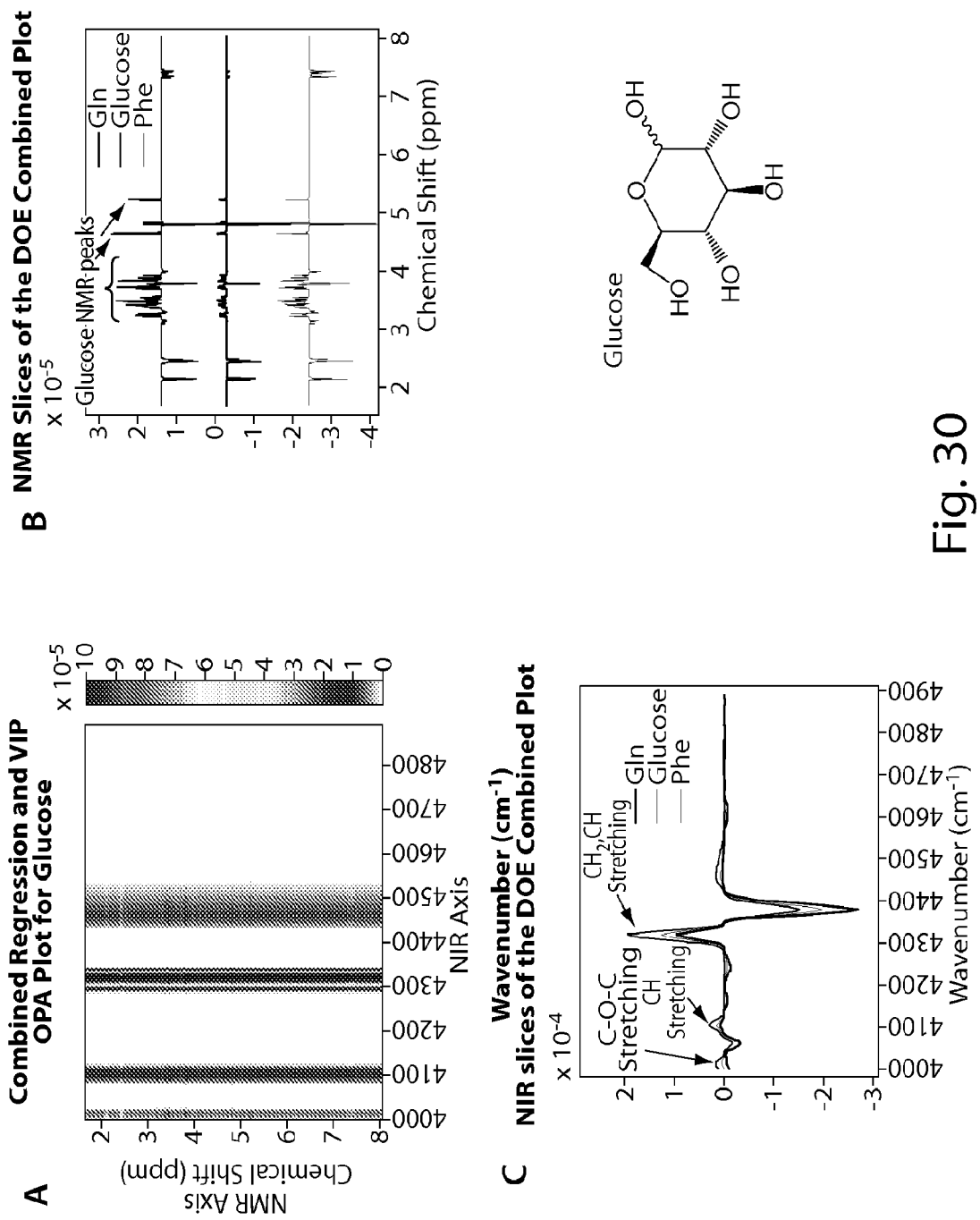
FIG. 30 shows the outer-product results from the PLS with Glucose concentration as the Y Block.
Figure 31:
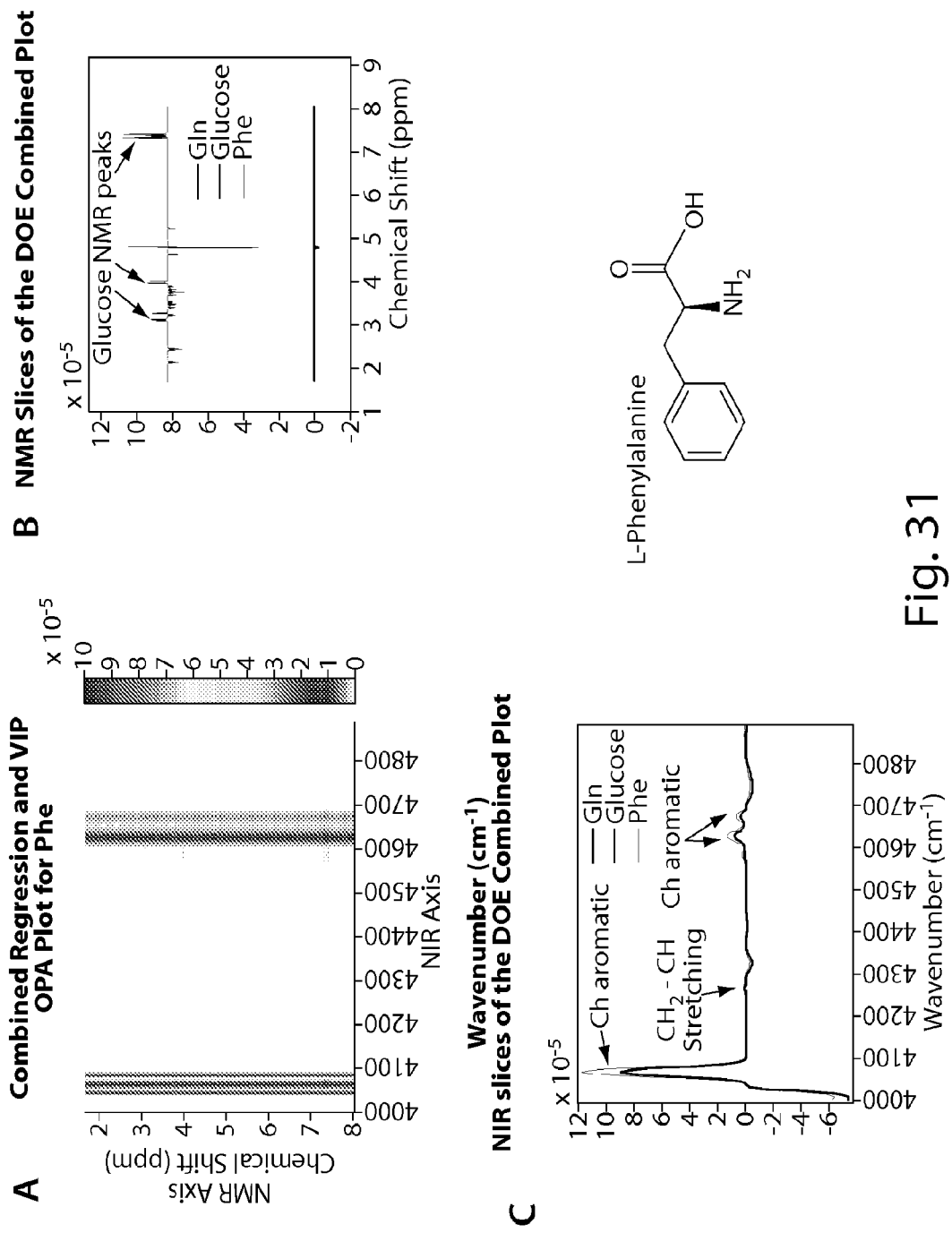
FIG. 31 shows the outer-product results from the PLS with Phe concentration as the Y Block.

FIGS. 29-31 illustrate the use of OPA-PLS models and the combined display to identify the regions of the NMR-NIR correlation for Phe, Gln and glucose.

FIG. 29A shows an image of the combined VIP and regression matrix obtained from multiplying the regression and the variable importance images from a PLS of the outer-product as the X-block and the Gln concentrations as the Y-block. In FIG. 29A, the intensity increases in the areas in the regions 4010, 4325, 4380, and 4762 cm$^{-1}$ in the NIR and 2.15, 2.45 and 3.78 ppm in the NMR. This is also evident when observing the high intensity of the Gln slice in FIG. 29B. All the other slices are of less intensity because they are indicative of glucose and Phe. Similarly, in FIG. 29C, the NIR slice corresponding to the Gln chemical shift (2.15 ppm) has the highest intensity out of all the other slices pertaining to glucose and Phe. Also, specific stretching NIR bands were observed from the NIR which corresponds to the different bonds shown in the structure of Gln (FIG. 29). For example, the absorption at 4380 cm$^{-1}$ which is a signature of CONH$_2$ can be clearly seen with the highest intensity for Gln. This is also unique for Gln because it is the only compound in this mixture that has a CONH$_2$ structure.

FIG. 30A shows the combined plot for the resultant OPA-PLS with the glucose concentration as the Y-block. The intensity of the correlation is highest at the NIR regions 4011, 4108, 4322 and 4469 cm$^{-1}$ as well as the known glucose NMR chemical shifts. From FIG. 30, the NMR slice pertaining to the 4108 cm$^{-1}$ possesses the highest intensity confirming the high correlation between that wavenumber and the glucose chemical shifts. This region on the NIR spectra is known to be the absorption band for CH stretching. FIG. 30C shows the NIR slices of the combined plot. In this plot, the highest correlation is present in the region of the CH2-CH stretching (4322 cm$^{-1}$) as well as the C—O—C region (4011 cm$^{-1}$) which are both evident in the structure of glucose displayed in FIG. 30.

FIG. 31A shows the combined plot resulting from the OPA-PLS with the Phe concentration as the Y-block. The high intensity regions of the NIR are 4065, 4268, 4629 and 4677 cm$^{-1}$ highlighting the Phe NMR chemical shift signals. Phe is known to have a signature NMR peak in the aromatic region (7.15 ppm). This is also reflected in the NIR spectrum that would have specific absorption in the CH aromatic benzene ring. FIG. 31B shows the NMR peaks are highest at the aromatic NIR absorption of 4060 cm$^{-1}$ while significantly less intense in the glucose and Gln regions. FIG. 31C also stresses the fact that these NIR absorptions are related to the Phe NMR chemical shifts because the highest intensity belongs to the NIR slice at 7.15 ppm. This can also be evident in the structure of Phe displayed in FIG. 31 possessing the benzene ring as well as the CH2-CH bond stretching highlighted in the NIR spectra (4268 cm$^{-1}$).

Figure 32:
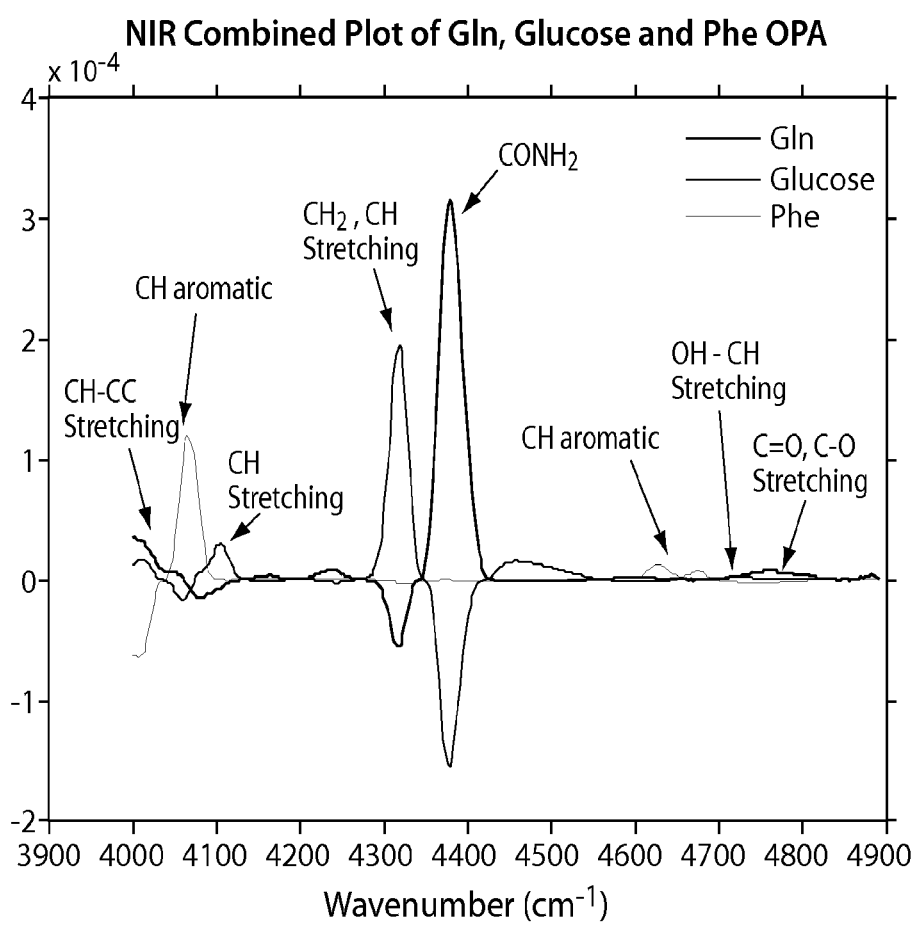
FIG. 32 shows NIR Profiles from OPA results

FIG. 32 shows the profiles resulting from each of the OPA-PLS combined graph. Each NIR profile was taken through an NMR peak that pertains to one of the three compounds. Gln was taken at 2.15 ppm, glucose was taken at 3.49 ppm and Phe was taken at 7.34 ppm. From FIG. 32, the distinction between each of the NIR profiles is apparent. For example, the Gln possesses a high peak at the CONH$_2$ while the glucose has a high peak right next to it at the CH2-CH stretching band. The Phe also has a unique signal at the CH aromatic region which is clear observed in the Figure.

Conclusions

Data fusion using outer-product analysis or sequential PLS is a powerful technique to assign NIR absorbance bands to specific chemical entities in both simple mixtures and complex mixtures of nutrients typically used in biopharmaceutical cell-culture media. By combining the regression and VIP images, better selectivity and intuitive understanding is made possible compared to more typical analysis of these vectors independently.

Sequential PLS between NIR and NMR improves the predictive ability of NIR spectra. Combining the water-suppression in NMR with the powder NIR spectra allows for more forceful models by de-emphasizing the water signal in the NIR.

Example 2

Pluronic F68 Data Fusion

Cell-culture in bioreactors requires oxygen to achieve high productivity. However, the introduction of air and agitation can damage cells as the air bubbles can lyse entrained cells, leading to reduced viable cell counts and lower yield. To reduce the adhesion of cells to air bubbles, surfactants are commonly added to bioreactor processes. However, differences between surfactant structures (e.g., in lot-to-lot variation) can result in differences in the free-energy of association between the surfactant and the air-bubble, thus modifying the ability of the reagent to protect cells.

Table 4 summarizes the average yield from two large-scale manufacturing facilities using production runs spanning approximately 5 years. There appear to be subtle differences in the yield between pluronic F68 lots. Yield data compared with NIR or fused NIR and NMR spectra were assessed to determine what aspect of pluronic F68 lots influenced these differences.

TABLE 4

Pluronic F68 Samples and Average Total Absorbance at 280 nm for Zn Column Eluate

| Vendor lot | Total Absorbance at 280 nm |
|---|---|
| 090M0059V | 9.61 |
| 091M0289V | 8.95 |
| 020M0029_1 | 10.57 |
| 060M0016 | 12.65 |
| 020M0029_2 | 10.57 |
| 069K1647 | 9.44 |
| 070M0117 | 12.98 |
| 018K0029 | 11.97 |

Figure 37:
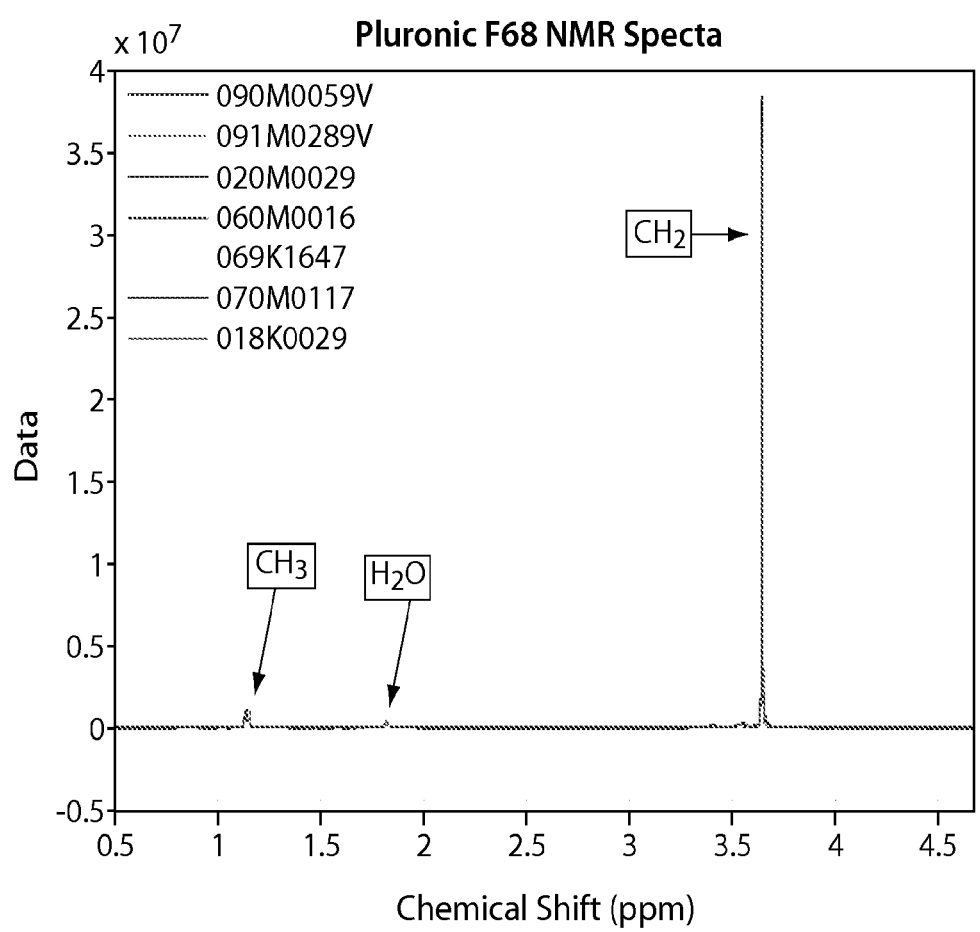
FIG. 37 shows Pluronic F68 NMR Spectra.
Figure 38:
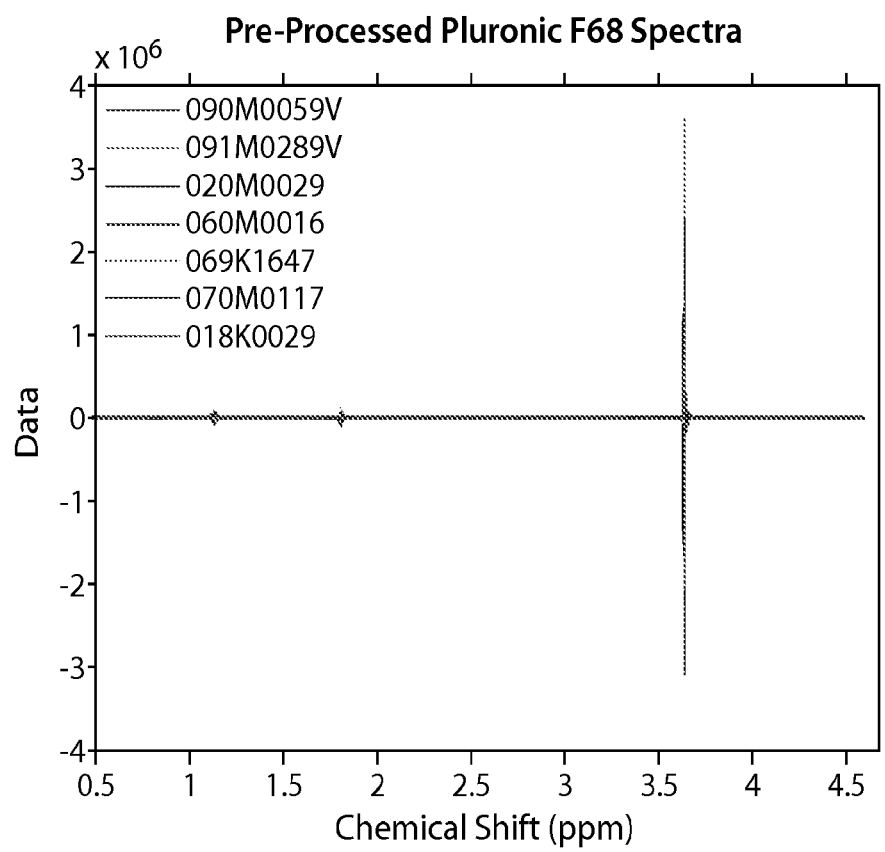
FIG. 38 shows Pre-processed Pluronic F68 NMR Spectra.
Figure 39:
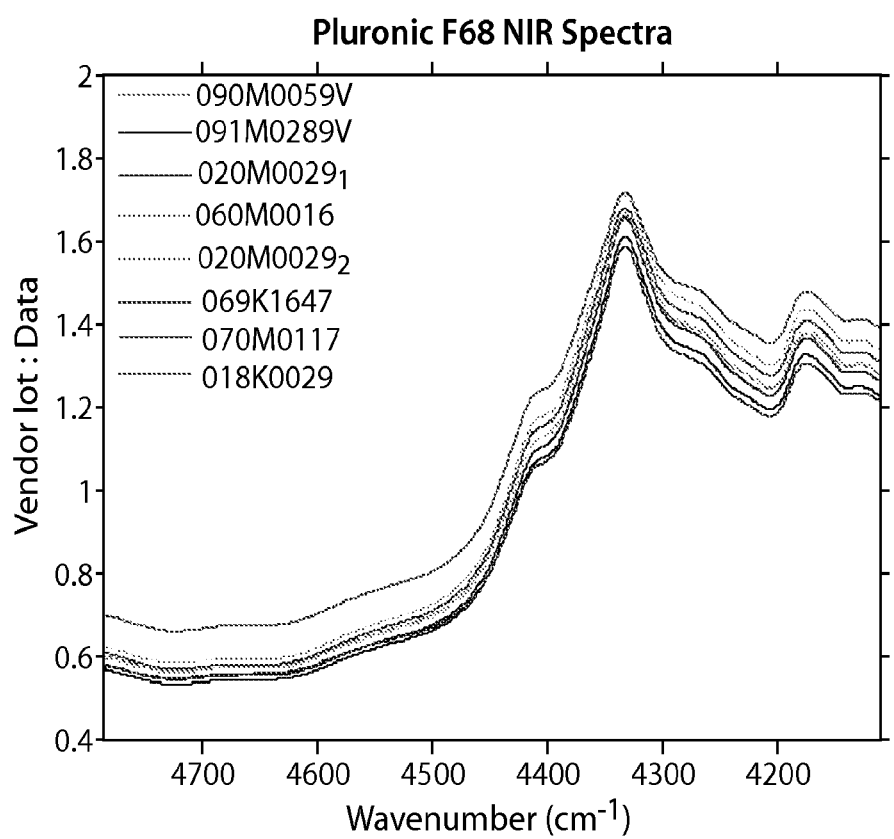
FIG. 39 shows Pluronic F68 NIR Spectra.
Figure 40:
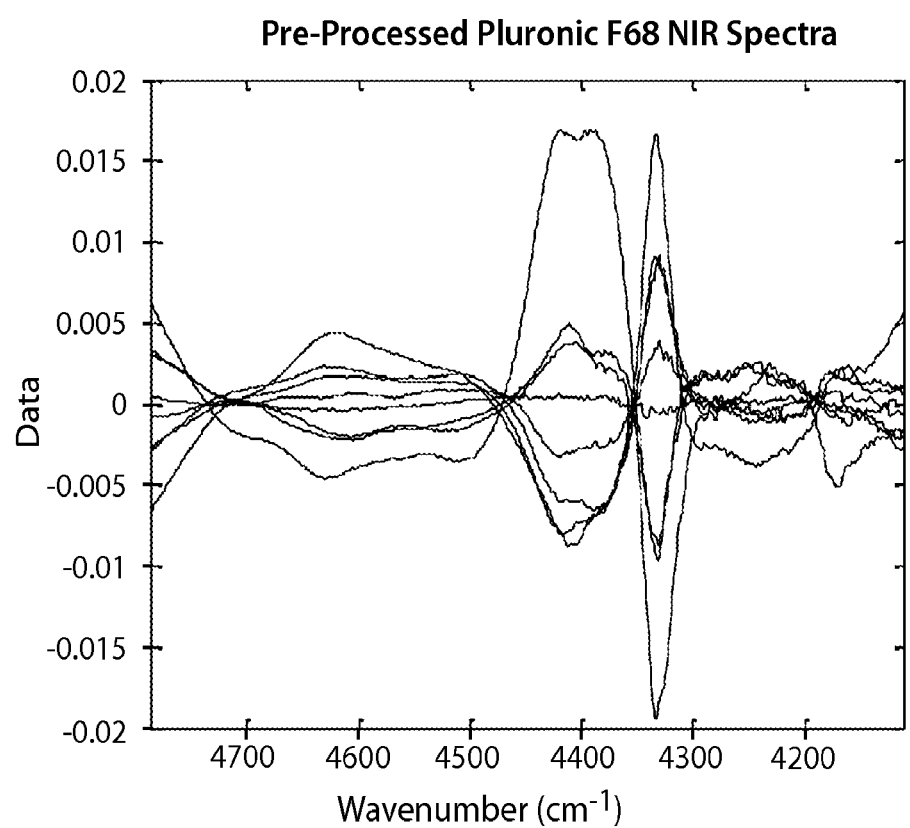
FIG. 40 shows Pre-processed Pluronic F68 NIR Spectra.

Methods:

A portion of each pluronic F68 (BASF) lot was dissolved in deuterated chloroform (CDCl$_3$) that contained 1% tetramethylsilane (TMS). The final concentration of pluronic in CDCl$_3$ was 5 mg/ml. The region of interest in the NMR was selected between 0.5-5 ppm as shown in FIG. 37. The NMR spectra were pre-processed using Lineup to align the chemical shifts. Furthermore, the spectra were baseline corrected using weighted least squares (WLS) and then mean centered as shown in FIG. 38. NIR spectra were also acquired on the powder pluronic F68 samples using 2 cm$^{-1}$ resolution and 128 scans. Only the combination band was selected (4000-4800 cm$^{-1}$) as shown in FIG. 39. The spectra were preprocessed using an extended multiplicative scatter correction algorithm (EMSC) and then mean centered as shown in FIG. 40.

Sequential PLS Combined Vector Result

Figure 36:
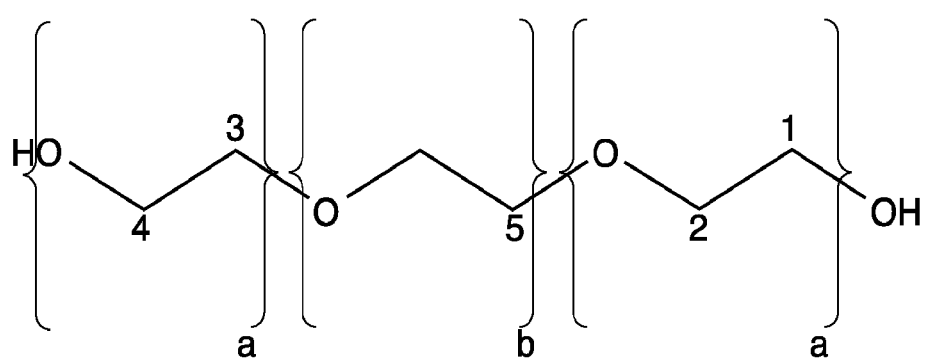
FIG. 36 shows the Pluronic F68 Molecular Structure.
Figure 41:
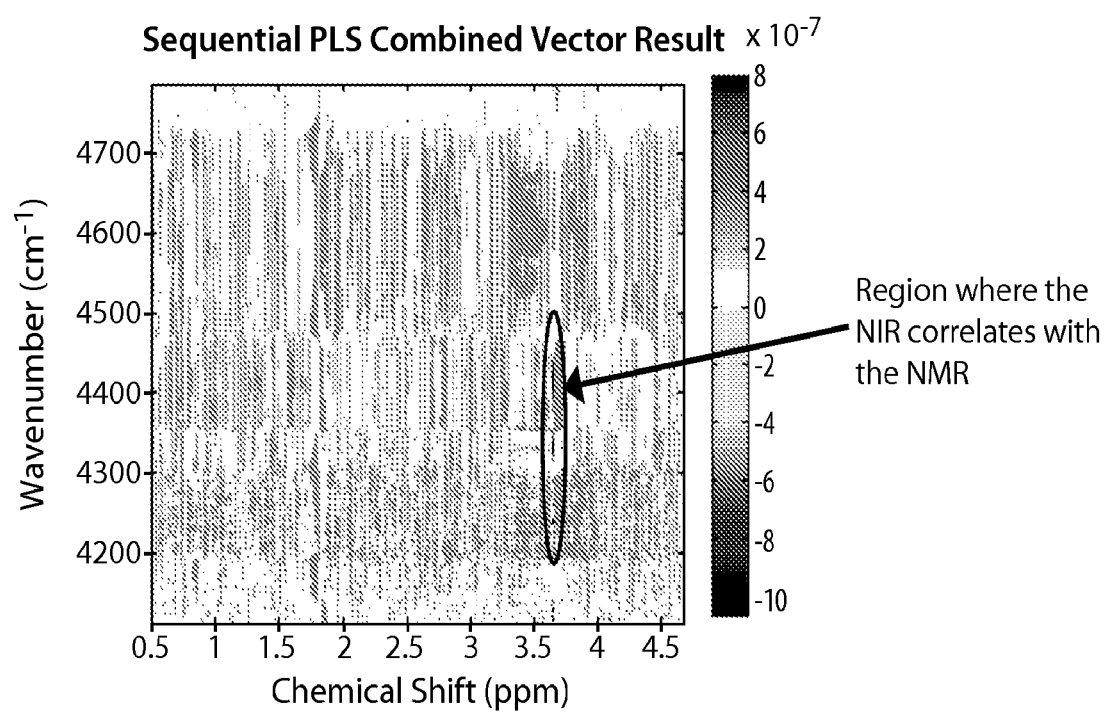
FIG. 41 shows Pluronic F68 Sequential PLS Combined Regression and VIP Plot.

The regression vector and the variable importance plot (VIP) were extracted from the sequential PLS model and shown in FIG. 41. The resulting plot shows a high correlation between the NMR and NIR in the band between 4200-4450 cm−1 and the chemical shift at 3.6 ppm. From the NMR analysis, the chemical shift at 3.6 ppm is due to the methylene group on the backbone of the Pluronic F68 molecule shown in FIG. 36. Therefore, this graph implies that the NIR band between 4200-4450 corresponds to the absorbance of the methylene group in the backbone.

Pluronic F68 Outer Product Analysis

Figure 42:
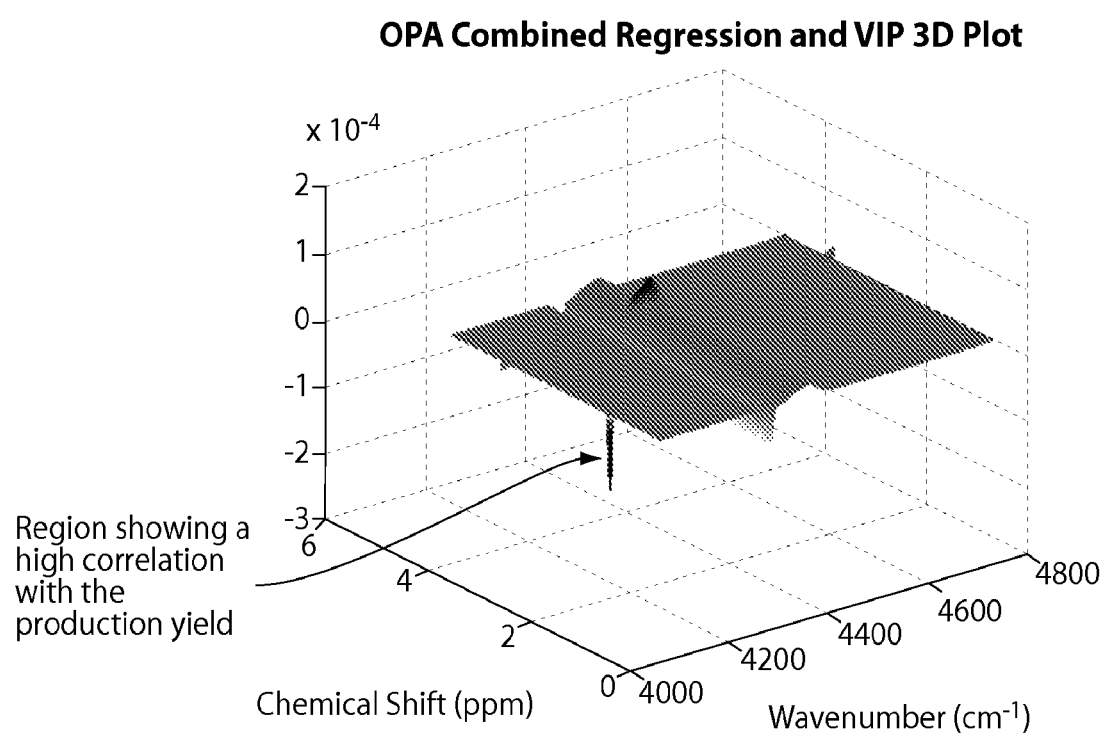
FIG. 42 shows Pluronic F68 Outer Product Analysis Combined Regression and VIP 3D Plot.

Outer product analysis was performed on the pluronic F68 NMR and NIR spectra. The spectra were further processed using the outer product pre-processing algorithm (scaling and shifting). A PLS model was then calculated using the Zn total absorbance at 280 nm as the Y-block and the unfolded pluronic NIR-NMR dataset as the X-block. The resultant regression vector and VIP vectors were then combined together to produce the combination plot displayed in FIG. 42. The combination plot shows that there is a strong correlation with the Y-block at the NMR region of 3.6 ppm and the region of 4200-4450 cm$^{-1}$ in the NIR axis.

Wavelength Selection in the NIR Only Model

The information concerning the high correlation between the NIR absorption bands at 4200-4450 cm$^{-1}$ can be used as a form of wavelength selection in the NIR only model for future use. Now that the important portion of the NIR is highlighted and identified by the NMR to pertain to the methylene group, the NIR model vs. the yield can be reduced to only the region between 4200 and 4450 cm$^{-1}$. Table 5 shows the benefits between using the wavelength selected model. The first model used the entire NIR spectra between 4000 and 9500 cm$^{-1}$ while omitting the water and water vapor regions. The second model only used the region recommended by the outer product results (4200-4450 cm$^{-1}$). Both models used the same pre-processing (EMSC and mean centering).

TABLE 5

Comparison between NIR models before and after wavelength selection

| Model | R^2 | RMSEC | RMSECV | Numbe of Latent Variables | Number of Points |
|---|---|---|---|---|---|
| Without wavelength selection | 0.918 | 0.338 | 0.426 | 3 | 4566 |
| With wavelength selection | 0.92 | 0.334 | 0.4 | 2 | 259 |

Table 5 shows that using the wavelength selection, the new NIR only model contains the same R2 and error but using less latent variables and a 95% reduction in the number of points used. This creates more robust and repeatable models; thus ensuring the usability of the NIR only model in the future without resorting back to the NMR for more routine testing. In the NIR only PLS model, the new validation lots are outside of the model's confidence level and therefore the resulting performance prediction is not as accurate or robust. In FIG. 44, the same set of new pluronic lots are inside the 95% confidence level; therefore, the model is validated and a prediction can be made on the new lots' performance. The number of points used in the model is also reduced by 95% and therefore creating simpler models that do not require much computational power or time while adding more interpretable results.

Example 3

Spectral Data Fusion Before Performing Outer Product Fusion

This Example shows that spectra processing before the multiplication of the two dimensions can be very helpful. A first set relates to the comparison of a dataset that was pre-processed using classical methods but without normalization or scaling. A second set relates to the same spectra with the same classical methods but with the addition of normalization to 1 and scaling the intensity range to be between 0-1.

The spectra data are from an experiment that contains different concentrations of glutamine (Gln), phenylalanine (Phe) and glucose. Proton Nuclear Magnetic Resonance (NMR) was acquired as well as Near Infrared (NIR). The data was then used for fusion and to demonstrate the drastic difference between the two processing methods. The addition of the normalization and scaling step introduces a significant improvement in the modeling of the unfolded dataset from the outer product.

Because the classical methods of pre-processing include a mean centering step, the all positive spectra data start to have negative components. Although this is beneficial in highlighting the major differences in the spectra and decreasing the number of principle components needed for the decomposition, the outer product of the mean-centered spectra introduces noise that decreases the model performance.

Outer product analysis was performed and the resulting 3 dimensional matrix was unfolded to produce a cube with a first dimension being the spectral information and the second dimension being the sample number. Principle Component Analysis (PCA) and Partial Least Squares (PLS) were then performed on the unfolded data as shown[1].

Figure 45:
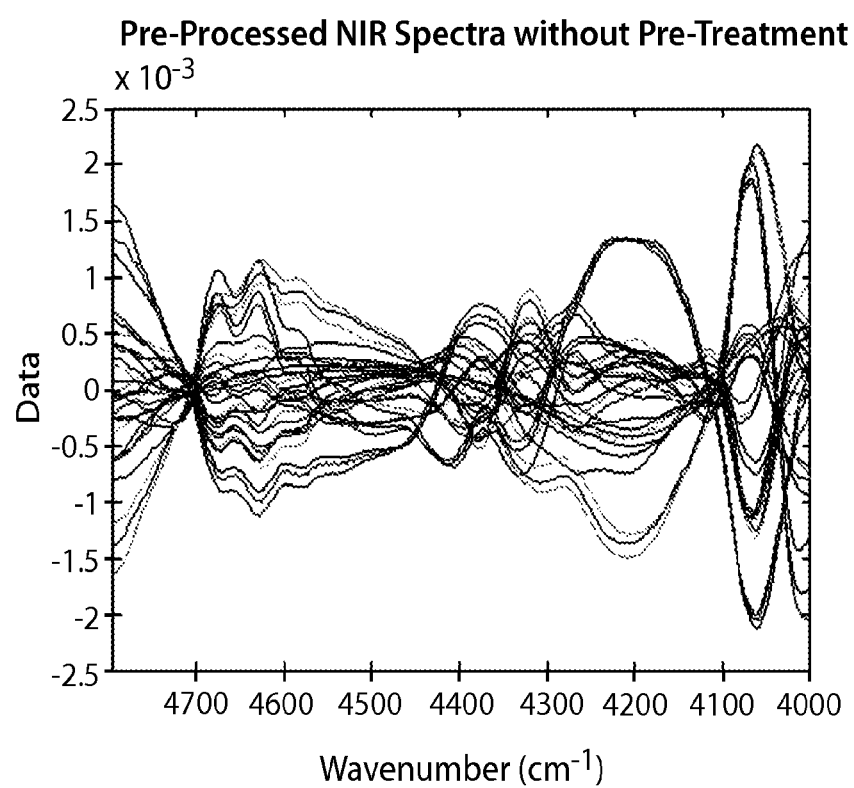
FIG. 45 shows a Pre-Processed NIR Spectra without normalization or scaling.
Figure 46:
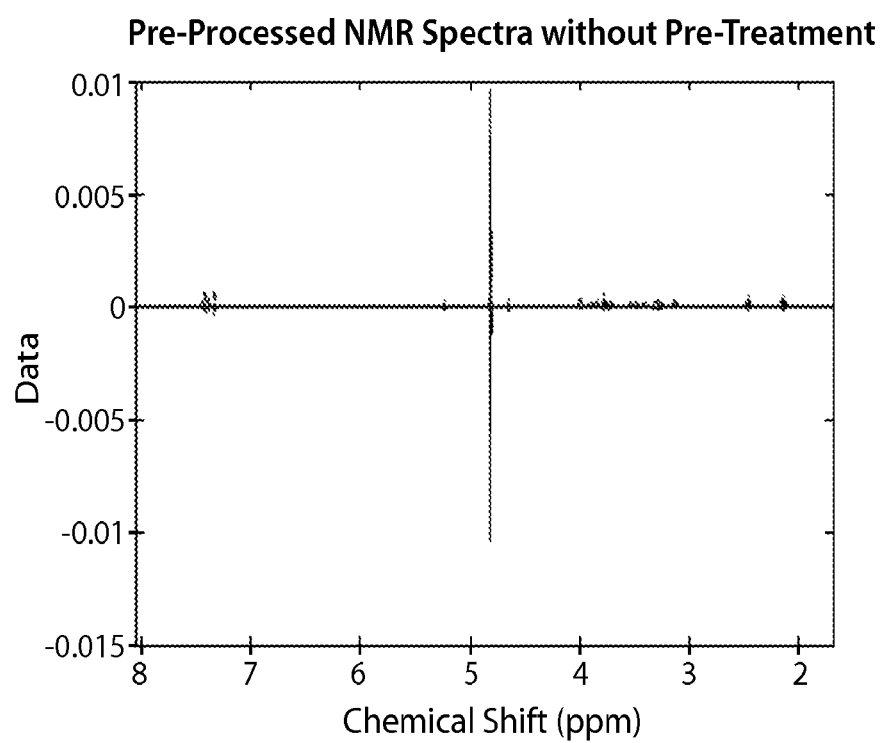
FIG. 46 shows a Pre-Processed NMR Spectra without normalization or scaling.

To assess the extent of the improvement, the outer product matrix with and without normalization and scaling results of the PLS model are displayed. The NIR spectra, after being processed using Extended Multiplicative Scatter Correction (EMSC) and Mean Centering (mncn) and then smoothed using a Savitzky-Golay algorithm with 15 point smoothing, are displayed in FIG. 45. FIG. 46 shows the NMR spectra after baseline correction using Weighted Least Squares (WLS) and mncn as well as a Savitzky-Golay 15 point smoothing.

Figure 47:
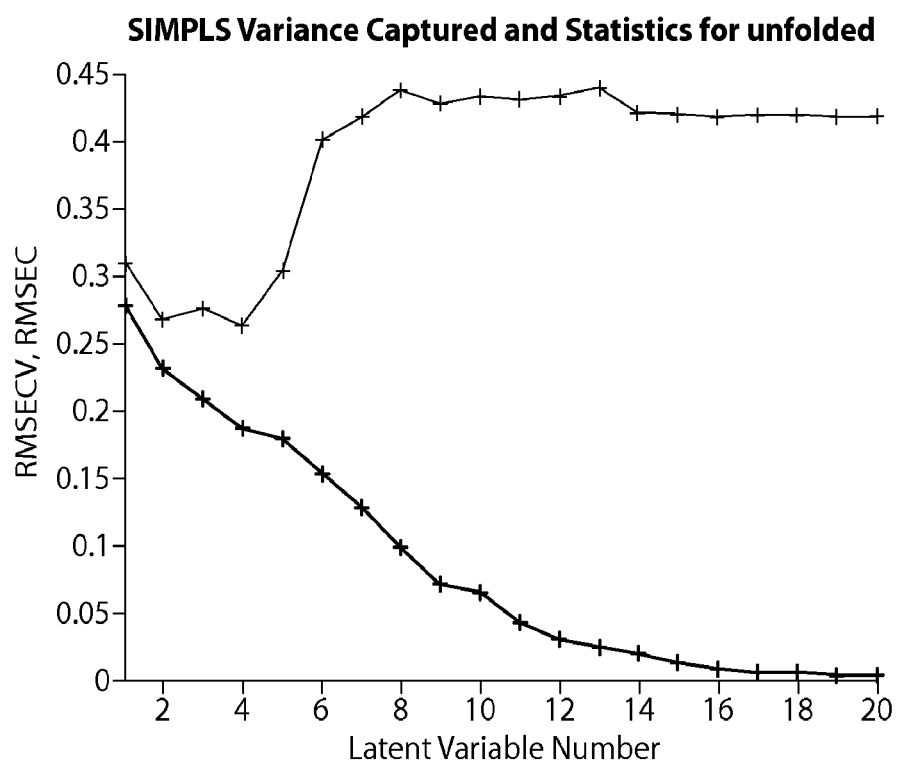
FIG. 47 shows a Cross Validation Press Plot using Venetian Blinds.

After performing the PLS analysis on the outer product unfolded matrix that had first been mean-centered, only 2 latent variables could be used in the model as suggested from the venetian blinds cross validation illustrated below in FIG. 47. The model had an RMSEC of 0.231, an RMSECV of 0.268 and an R$^2$ of 0.47.

Figure 48:
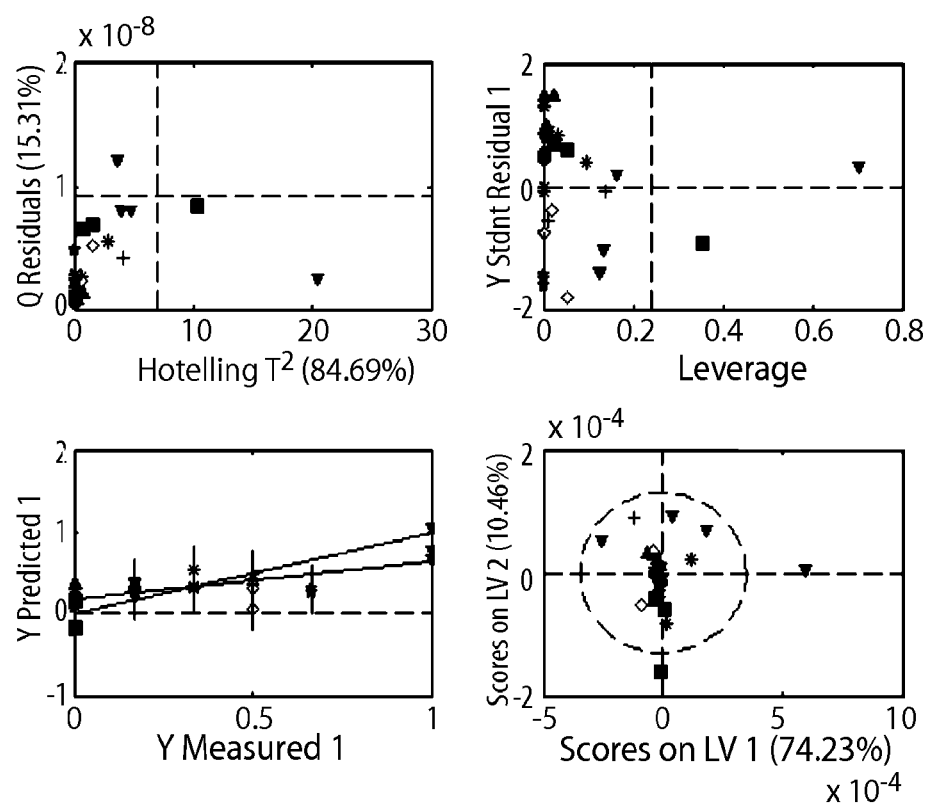
FIG. 48 shows a PLS model detailing the unfolded outer product matrix without normalization and scaling.
Figure 49:
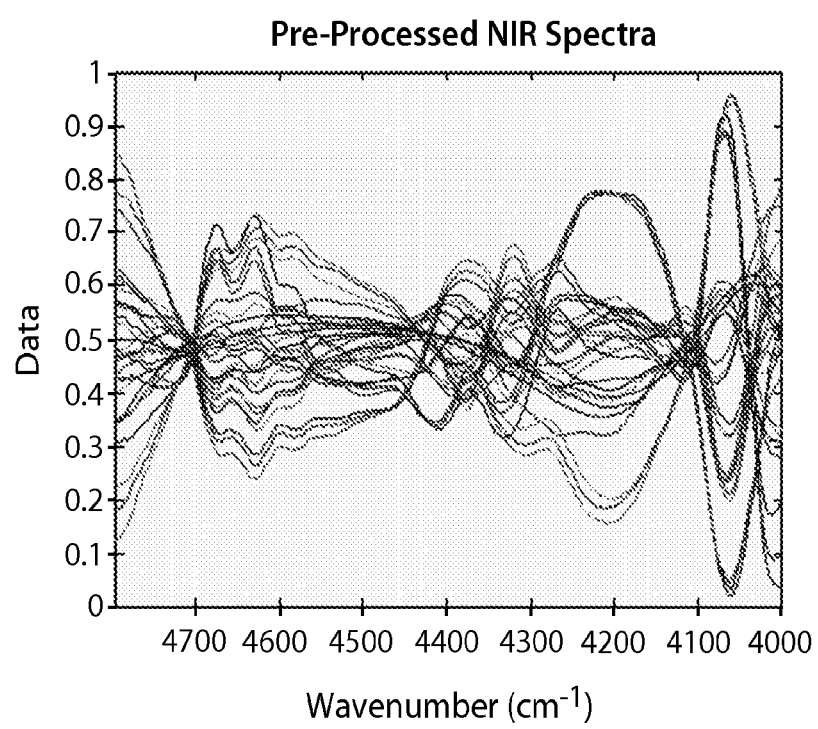
FIG. 49 shows a Pre-Processed NIR Spectra with Normalization and Scaling.
Figure 50:
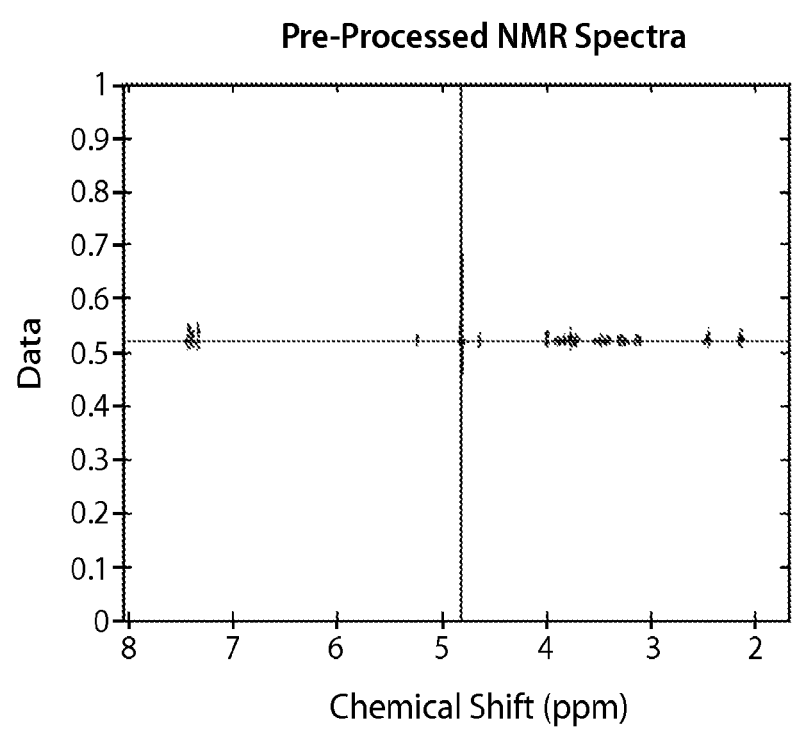
FIG. 50 shows a Pre-Processed NMR Spectra with Normalization and Scaling.

The latent variable scores are not well separated in this model. The prediction plot contains large errors as shown in the latent variable scores and the prediction plot in FIG. 48. In contrast, a PLS model performed on the normalized and scaled spectra of the NIR and NMR are shown in FIGS. 49 and 50, respectively. The spectral intensity were normalized to 1 and scaled so that the intensity value range is between 0 and 1.

Figure 51:
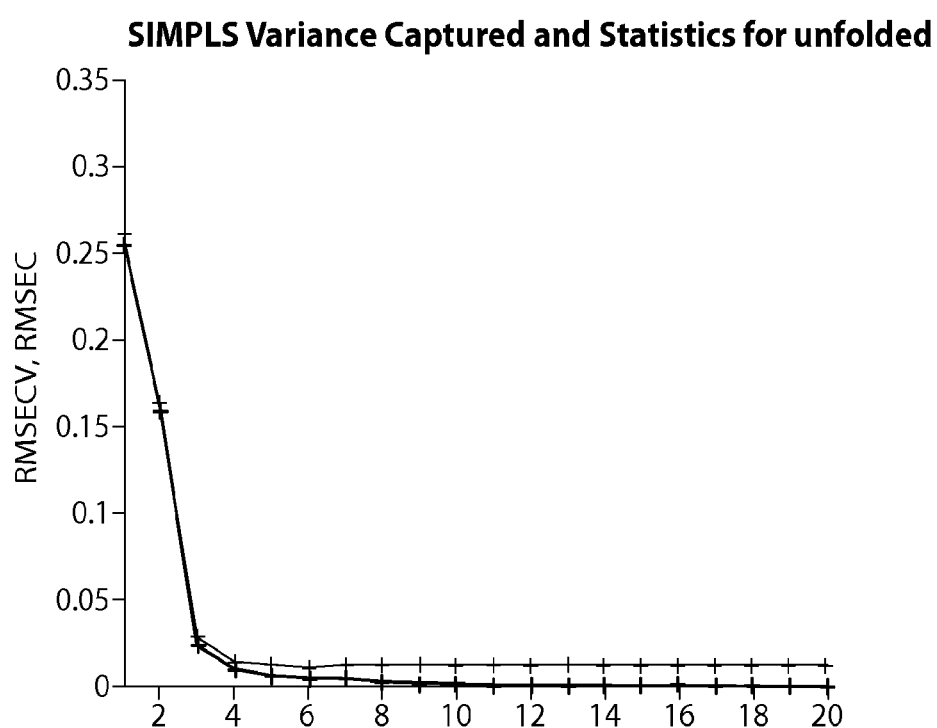
FIG. 51 shows a venetian blinds cross validation PRESS Plot.

The PLS model was calculated using 4 components as justified by the venetian blinds cross validation PRESS plot shown in FIG. 51. The resulting model had an RMSEC of 0.01, an RMSECV of 0.013 and an R$^2$ of 0.999.

Figure 52:
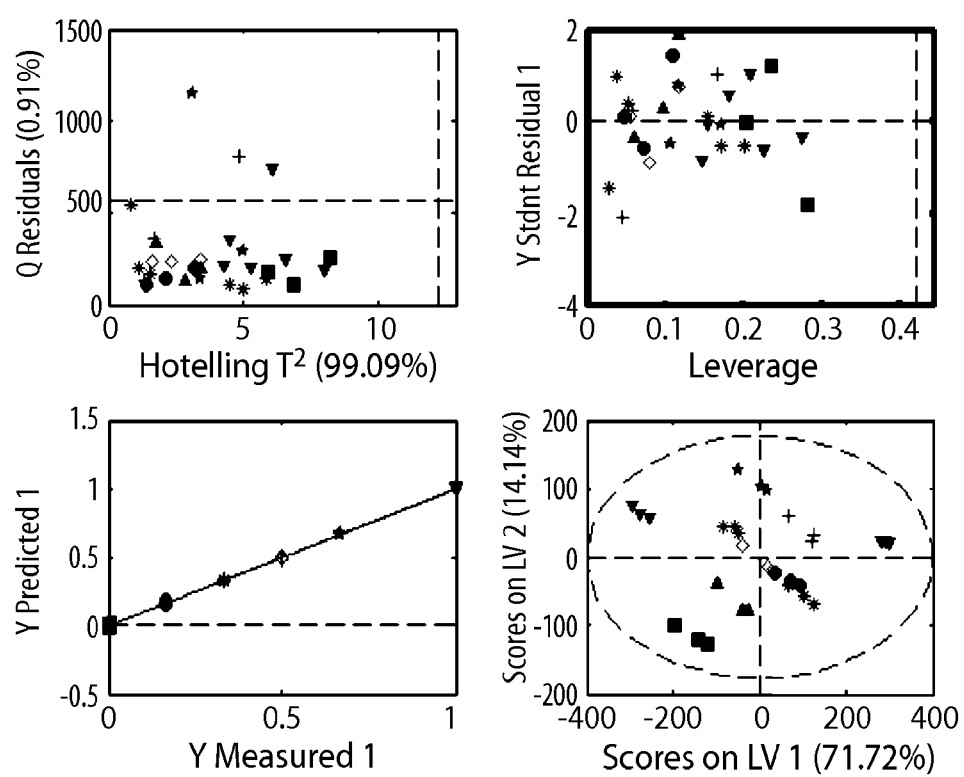
FIG. 52 shows PLS model details for an outer-product PLS using normalized and scaled NIR and NMR spectra.

The model details are highlighted in FIG. 52 showing a good separation between the latent variable scores and a very accurate prediction vs. actual plot are obtained. Table 6 shows the RMSEC, RMSECV and R2 values of the two processes to illustrate further the advantage of the normalization and scaling before performing the outer product.

TABLE 6

Analytical figures of merit for outer-product PLS models prepared with and without normalization and scaling.

| | RMSEC | RMSECV | R$^2$ |
|---|---|---|---|
| Model Without Normalization and Scaling | 0.231 | 0.268 | 0.47 |
| Model With Normalization and Scaling | 0.01 | 0.013 | 0.999 |

REFERENCES (1) Rutledge, D. N.; Banos, A. S.; Giangiacomo, R. *Spec. Publ.—R. Soc. Chem.* FIELD Full Journal Title: Special Publication—Royal Society of Chemistry 2001, 262, 179-192.

(2) Workman Jr., J.; Weyer, L. *Practical Guide to Interpretive Near-Infrared Spectroscopy*, 1 ed.; CRC Press: Boca Raton, Fla., 2008.
(3) Giangiacomo, R.; Pani, P.; Barzaghi, S. *Journal of Near Infrared Spectroscopy* 2009, 17, 329-335.
(4) Wiklund, S.; Johansson, E.; Sjostrom, L.; Mellerowicz, E. J.; Edlund, U.; Shockcor, J. P.; Gottfries, J.; Moritz, T.; Trygg, J. *Analytical Chemistry* 2008, 80, 115-122.
(5) Cloarec, O.; Dumas, M.-E.; Craig, A.; Barton, R. H.; Trygg, J.; Hudson, J.; Blancher, C.; Gauguier, D.; Lindon, J. C.; Holmes, E.; Nicholson, J. *Analytical Chemistry* 2005, 77, 1282-1289.
(6) Crockford, D. J.; Holmes, E.; Lindon, J. C.; Plumb, R. S.; Zirah, S.; Bruce, S. J.; Rainville, P.; Stumpf, C. L.; Nicholson, J. K. *Analytical Chemistry* 2006, 78, 363-371.
(7) Gujral, P.; Amrhein, M.; Ergon, R.; Wise, B. M.; Bonvin, D. *Journal of Chemometrics* 2011, 25, 456-465.
(8) Teofilo, R. F.; Martins, J. P. A.; Ferreira, M. M. C. Journal of Chemometrics 2009, 23, 32-48.
(11) Kemper, M. S.; Luchetta, L. M. Journal of Near Infrared Spectroscopy 2003, 11, 155-174.
(12) Candolfi, A.; De Maesschalck, R.; Massart, D. L.; Hailey, P. A.; Harrington, A. C. E. Journal of Pharmaceutical and Biomedical Analysis 1999, 19, 923-935.
(13) Brimmer, P. J.; Hall, J. W. Canadian Journal of Applied Spectroscopy 1993, 38, 155-162.
(14) Hall, J. W.; McNeil, B.; Rollins, M.; Draper, I.; Thompson, B.; Macaloney, G. Applied Spectroscopy 1996, 50, 102-108.
(15) Tamburini, E.; Vaccari, G.; Tosi, S.; Trilli, A. Applied Spectroscopy 2003, 57, 132-138.
(16) Arnold, S. A.; Crowley, J.; Woods, N.; Harvey, L. M.; McNeil, B. Biotechnology & Bioengineering 2003, 84, 13-19.
(17) Rhiel, M.; Cohen, M. B.; Murhammer, D. W.; Arnold, M. A. Biotechnology & Bioengineering 2002, 77, 73-82.
(18) Chung, H.; Arnold, M. A.; Rhiel, M.; Murhammer, D. W. Applied Biochemistry & Biotechnology 1995, 50, 109-125.
(19) Brookes I K, G. B., Hammond S V. In Near infrared spectroscopy: the future waves; Williams, D., Ed.; NIR publications: Chichester, UK, 1996, pp 259-267.
(20) Yeung, K. S.; Hoare, M.; Thornhill, N. F.; Williams, T.; Vaghjiani, J. D. Biotechnology & Bioengineering. 1999, 63, 684-693.
(21) Lewis, C. B.; McNichols, R. J.; Gowda, A.; Cote, G. L. Appl. Spectrosc. FIELD Full Journal Title: Applied Spectroscopy 2000, 54, 1453-1457.
(22) Macalony, G.; Draper, I.; Preston, J.; Anderson, K. B.; Rollins, M. J. Food Bioprod. Process. 1996, 74, 212-220.
(23) Jorgensen, P.; Pedersen, J. G.; Jensen, E. P.; Ebensen, K. H. Journal of Chemometrics 2004, 18, 81-91.
(24) Luo, Y.; Chen, G. X. Biotechnology And Bioengineering 2007, 97, 1654-1659.
(25) Lanan, M. In Quality by Design for Biopharmaceuticals: Principles and Case Studies, 1 ed.; Rathore, A. S. M., Rohin, Ed.; John Wiley & Son: Hoboken, N.J., 2009, pp 198-210.
(26) Duarte, I. F.; Barros, A.; Almeida, C.; Spraul, M.; Gil, A. M. Journal of Agricultural and Food Chemistry 2004, 52, 1031-1038.
(27) Duarte, I.; Banos, A.; Belton, P. S.; Righelato, R.; Spraul, M.; Humpfer, E.; Gil, A. M. Journal of Agricultural and Food Chemistry 2002, 50, 2475-2481.
(28) Xiaobo, Z.; Jiewen, Z.; Povey, M. J. W.; Holmes, M.; Hanpin, M. Analytica chimica acta, 667, 14-32.
(29) Baianu, I. C.; You, T. In Handbook of Food Analysis Instruments; Otles, S., Ed.; CRC Press: Boca Raton, Fla., 2009 pp 247-279.
(30) Rutledge, D. N.; Banos, A. S.; Giangiacomo, R. Spec. Publ.—R. Soc. Chem. FIELD Full Journal Title: Special Publication—Royal Society of Chemistry 2001, 262, 179-192.
(31) Workman Jr., J.; Weyer, L. Practical Guide to Interpretive Near-Infrared Spectroscopy, 1 ed.; CRC Press: Boca Raton, Fla., 2008.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

The contents of all references, patents and published patent applications cited throughout this application are incorporated herein by reference in their entirety, particularly for the use or subject matter referenced herein.

What is claimed is:

1. A method of identifying one or more informative subsets of frequency ranges of an NIR spectrum for evaluating a biological sample, the method comprising
performing a Nuclear Magnetic Resonance (NMR) analysis on a biological sample to obtain an NMR spectrum,
performing a Near Infrared Spectroscopy (NIR) analysis on the biological sample to obtain an NIR spectrum, and
obtaining one or more informative subsets of NIR frequency ranges of the NIR spectrum by performing a data fusion analysis of the NMR spectrum with the NIR spectrum.

2. The method of claim 1, wherein the data fusion analysis comprises an Outer Product Analysis (OPA).

3. The method of claim 2, wherein the OPA comprises multiplying the NMR spectrum with the NIR spectrum.

4. The method of claim 2, wherein OPA comprises multiplying Regression vectors and Variable Importance in Projection (VIP) vectors.

5. The method of claim 1, wherein the data fusion analysis comprises a partial least square (PLS) analysis.

6. The method of claim 5, wherein the PLS analysis comprises an x-block of NIR and NMR data and a y-block of one or more components of the biological sample.

7. The method of claim 5, wherein the results are displayed using a combination vector.

8. The method of claim 1, wherein the data fusion analysis is a computer-implemented step.

9. The method of claim 1 further comprising:
performing a second NIR analysis on a second biological sample to obtain a second NIR spectrum, and
evaluating the second biological sample by analyzing the one or more informative subsets of NIR frequency ranges of the second NIR spectrum.

10. The method of claim 1, wherein the biological sample is a sample of a biological growth or expression system.

11. The method of claim 1, wherein the biological sample is a starting material for a biological growth or expression system.

12. The method of claim 1, wherein the biological sample comprises more than three different nutrient components.

13. The method of claim 1, wherein the biological sample comprises two or more amino acids, peptides, sugars, carbohydrates, vitamins, growth factors, salts, synthetic material, antibiotics, surfactants, buffers, or any combination thereof.

14. The method of claim 1, wherein the biological sample comprises a surfactant.

15. The method of claim 1, wherein the biological sample comprises Glutamine (Gln), glucose, and/or phenylalanine (Phe).

16. The method of claim 1, wherein the biological sample comprises a mixture of nutrients of a biopharmaceutical cell culture media.

17. A method of evaluating a biological sample, the method comprising
performing a Near Infrared Spectroscopy (NIR) analysis on a biological sample to obtain an NIR spectrum for a subset of NIR wavelengths that is informative for evaluating the biological sample,
wherein the subset was identified in a data fusion analysis of a reference NIR spectrum with a reference NMR spectrum.

18. A method of analyzing a biological sample, the method comprising:
performing a Near Infrared Spectroscopy (NIR) analysis on a biological sample to obtain a NIR spectrum, and
evaluating the biological sample by analyzing one or more informative subsets of NIR frequency ranges of the NIR spectrum, wherein the one or more informative subsets of NIR frequency ranges were identified by performing a data fusion analysis of a reference Nuclear Magnetic Resonance (NMR) spectrum with a reference NIR spectrum.

* * * * *